US006204260B1

(12) United States Patent
Bruns, Jr. et al.

(10) Patent No.: US 6,204,260 B1
(45) Date of Patent: *Mar. 20, 2001

(54) NON-PEPTIDYL VASOPRESSIN $V_{1A}$ ANTAGONISTS

(75) Inventors: Robert F Bruns, Jr., Carmel; Robin DG Cooper; Bruce A Dressman, both of Indianapolis; David C Hunden, Carmel; Stephen W Kaldor, Indianapolis; Gary A Koppel, Indianapolis; John R Rizzo, Indianapolis; Jeffrey J Skelton, Indianapolis; Mitchell I Steinberg, Indianapolis, all of IN (US)

(73) Assignee: Eli Lilly and Company, Indianapolis, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/125,737

(22) PCT Filed: Feb. 20, 1997

(86) PCT No.: PCT/US97/03039

§ 371 Date: Aug. 19, 1999

§ 102(e) Date: Aug. 19, 1999

(87) PCT Pub. No.: WO97/30707

PCT Pub. Date: Aug. 28, 1997

Related U.S. Application Data

(60) Provisional application No. 60/012,149, filed on Feb. 23, 1996, provisional application No. 60/012,188, filed on Feb. 23, 1996, and provisional application No. 60/012,215, filed on Feb. 23, 1996.

(30) Foreign Application Priority Data

Mar. 9, 1996 (GB) .................................................. 9605044
Mar. 9, 1996 (GB) .................................................. 9605045
Mar. 9, 1996 (GB) .................................................. 9605046

(51) Int. Cl.[7] ...................... A61K 31/395; C07D 205/00
(52) U.S. Cl. ........................................ 514/210.1; 540/200
(58) Field of Search ............................ 540/200; 514/210

(56) References Cited

U.S. PATENT DOCUMENTS

| 4,734,498 | 3/1988 | Cooper ................... 540/364 |
| 4,751,299 | 6/1988 | Sugwara et al. ..................... 540/364 |
| 4,772,694 | 9/1988 | Cooper ................... 540/364 |
| 5,373,089 | 12/1994 | Flouret et al. ....................... 530/315 |
| 5,480,987 | 1/1996 | Ziegler, Jr., et al. ................ 540/200 |
| 5,846,966 | * 12/1998 | Rosenblum et al. ................. 514/210 |
| 5,952,321 | * 9/1999 | Doherty et al. ...................... 514/210 |
| 5,986,108 | * 12/1998 | Singh et al. ......................... 540/200 |

FOREIGN PATENT DOCUMENTS

| 0 144 840 A2 | 6/1985 | (EP) . |
| 0 211 540 A1 | 2/1987 | (EP) . |
| 0 215 435 A1 | 3/1987 | (EP) . |
| 0282 895 A2 | 9/1988 | (EP) . |
| 0 362 902 A2 | 4/1990 | (EP) . |
| 0 558 215 A1 | 9/1993 | (EP) . |

OTHER PUBLICATIONS

Richard, et al., *The American Psychological Society*, 71:2, pp. 331–370 (1991).
Argiolas, et al., *Neuroscience & Biobehavioral Reviews*, 15, pp. 217–231 (1991).
Pavo, et al., *J. Med. Chem.*, 37, pp. 465–484 (1991).
Falke, *Progress in Neurobiology*, 36, pp. 465–484 (1991).
Kimura, et al., *Nature*, 365, pp. 526–529 (1992).

* cited by examiner

Primary Examiner—Deborah C. Lambkin
(74) Attorney, Agent, or Firm—Robert D. Titus

(57) ABSTRACT

This invention provides methods and 2-(azetidin-2-on-1-yl) acetic acid derivatives for the antagonism of the vasopressin $V_{1a}$ receptor.

12 Claims, No Drawings

NON-PEPTIDYL VASOPRESSIN V$_{1A}$ ANTAGONISTS

Provisional application Ser. No. 60/012,149 filed Feb. 23, 1996 Provisional application Ser. No. 60/012,188 filed Feb. 23, 1996 Provisional application Ser. No. 60/012,215 filed Feb. 23, 1996.

Vasopressin, a neurohypophyseal neuropeptide produced in the hypothalamus, is involved in water metabolism homeostasis, renal function, mediation of cardiovascular function, non-opioid mediation of tolerance for pain, and regulation of temperature in mammals. In addition to being released into the circulation via the posterior pituitary, vasopressin acts as a neurotransmitter in the brain. Three vasopressin receptor subtypes, designated V$_{1a}$, V$_{1b}$, and V$_2$ have been identified. The human V$_{1a}$ receptor has been cloned (Thibonnier et al., *The Journal of Biological Chemistry*, 269(5), 3304–3310 (1994)), and has been shown by radioligand binding techniques to be present in vascular smooth muscle cells, hepatocytes, blood platelets, lymphocytes and monocytes, type II pneumocytes, adrenal cortex, brain, reproductive organs, retinal epithelium, renal mesangial cells and the A10, A7r5, 3T3 and WRK-1 cell lines (Thibonnier, *Neuroendocrinology of the Concepts in Neurosurgery Series* 5, (Selman, W., ed), 19–30, Williams and Wilkins, Baltimore, (1993)).

Structural modification of vasopressin has provided a number of vasopressin agonists (Sawyer, *Pharmacol. Reviews*, 13, 255 (1961)). In the past decade, several potent and selective vasopressin peptide antagonists have been designed (Lazslo, et al., *Pharmacological Reviews*, 43, 73–108 (1991); Mah and Hofbauer, *Drugs of the Future*, 12, 1055–1070 (1987); Manning and Sawyer, *Trends in Neuroscience*, 7, 8–9 (1984)). Their lack of oral bioavailability and short half-life, however, have severely limited their therapeutic potential. While novel structural classes of non-peptidyl vasopressin V$_{1a}$ antagonists have been discovered (Yamamura, et al., *Science*, 275, 572–574 (1991); Serradiel-Le Gal, et al., *Journal of Clinical Investigation*, 92, 224–231 (1993); Serradiel-Le Gal, et al., *Biochemical Pharmacology*, 47(4), 633–641 (1994)), a clinically useful agent is yet to be identified.

The general structural class of substituted 2-(azetidin-2-on-1-yl)acetic acid esters and amides are well known in the art as synthetic intermediates for the preparation of β-lactam antibiotics (U.S. Pat. No. 4,751,299). While certain compounds within this structural class have been reported as possessing antibiotic activity, their activity at the vasopressin V1a receptor has heretofore not been appreciated.

This invention provides a method for the antagonism of the vasopressin V1a receptor comprising administering to a mammal in need of such antagonism a pharmaceutically effective amount of a 2-(azetidin-2-on-1-yl)acetic acid derivative of Formula I

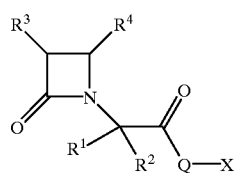

I where
R$^1$ is hydrogen, C$_1$–C$_5$ alkyl, —C(O)NR$^5$X', (C$_1$–C$_4$ alkylene)C(O)NR$^5$X', hydroxy substituted C$_1$–C$_5$ alkyl, C$_1$–C$_5$ acyl optionally substituted as the ethylene glycol ketal, C$_3$–C$_6$ cycloalkylcarbonyl, benzoyl, phenyl, phenyl(C1–C4 alkylene), phenoxyacetyl, phenylacetyl where the phenyl is optionally substituted with halo, C$_1$–C$_4$ alkyl, C$_1$–C$_4$ alkoxy, or trifluoromethyl, or α-hydroxy-α-benzoylbenzyl;

R$^2$ is hydrogen, or hydroxy substituted C$_1$–C$_5$ alkyl;

R$^3$ is phthalimido, azido, phenoxyacetamido, 4,5-diphenyloxazol-2-on-3-yl, or a structure selected from the group consisting of

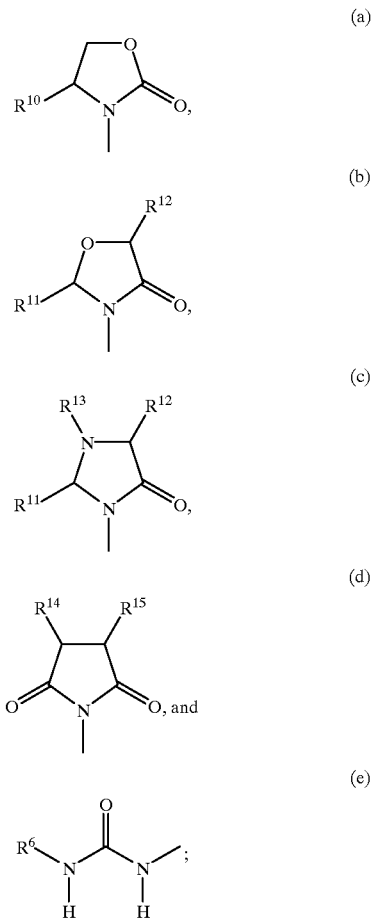

R$^4$ is:
phenethyl, or 2-arylethen-1-yl where aryl is selected from the group consisting of furyl, pyrrolyl, pyridyl, thiazolyl, oxazolyl, isoxazolyl, imidazolyl, pyrazolyl, pyrimidinyl, thiadiazolyl, oxadiazolyl, quinolyl, isoquinolyl, naphthyl, and phenyl optionally substituted with 1 to 3 substituents selected from the group consisting of C$_1$–C$_6$ alkyl, C$_1$–C$_6$ alkoxy, C$_1$–C$_6$ alkylthio, nitro, halo, carboxy, and amido;

Q is —O—, —S—, or —NR$^5$—;

R$^5$ is hydrogen, hydroxy, C$_1$–C$_4$ alkoxycarbonyl, benzyl, or C$_1$–C$_4$ alkyl;

R$^6$ is C$_1$–C$_8$ alkyl, C$_3$–C$_8$ cycloalkyl, phenyl, or phenyl (C1–C4 alkylene) optionally substituted on the alkylene chain with C$_1$–C$_4$ alkoxycarbonyl;

X and X' are independently hydrogen, C$_1$–C$_6$ alkyl, 2-(trimethylsilyl)ethyl, C$_1$–C$_4$ alkyl ω-substituted with C$_1$–C$_4$ alkoxy, Y, (optionally substituted C$_1$–C$_4$ alkylene)-Y, or (optionally substituted C$_2$–C$_4$ alkylene)-NR$^7$R$^8$;

Y is phenyl, optionally substituted phenyl, diphenylmethyl, $C_3-C_6$ cycloalkyl, naphthyl, tetrahydronaphthyl, indanyl, fluorenyl, pyrrolyl, 1-($C_1-C_4$ alkyl)pyrrolyl, imidazolyl, pyrazolyl, pyridinyl, furyl, benzodioxanyl, tetrahydrofuryl, pyrrolidinyl, 1-($C_1-C_4$ alkyl)pyrrolidinyl, 1-benzylpyrrolidinyl, piperidinyl, 1-benzylpiperidin-4-yl, or quinuclidinyl;

$R^7$ is hydrogen, or $C_1-C_4$ alkyl;

$R^8$ is $C_1-C_4$ alkyl, phenyl, or pyridinyl optionally substituted with nitro;

$R^7$ and $R^8$ taken together with the nitrogen atom to which they are attached form morpholinyl, optionally substituted piperazinyl, or pyrrolidinyl;

$R^5$ and X' taken together with the nitrogen to which they are attached form:
  2-(pyrrolidin-1-ylmethyl)pyrrolidin-1-yl;
  piperidinyl optionally substituted at the 4-position with hydroxy, pyrrolidin-1-yl, piperidin-1-yl, benzyl, or piperidin-1-yl(C1–C4 alkylene);
  piperidinyl mono- or disubstituted with methyl;
  piperazinyl optionally substituted at the 4-position with $C_1-C_4$ alkyl, $C_3-C_6$ cycloalkyl, phenyl, phenyl (C1–C4 alkylene), α-methylbenzyl, N-($C_1-C_4$ alkyl)acetamid-2-yl, or $C_1-C_4$ alkoxycarbonyl;
  1,2,3,4-tetrahydroisoquinolin-2-yl; or
  homopiperazinyl substituted in the 4-position with $C_1-C_4$ alkyl;

$R^2$, Q, and X taken together with the bridging carbon atoms to which they are attached form the lactone

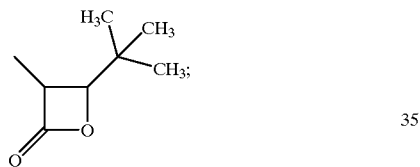

$R^{10}$ is $C_1-C_6$ alkyl, $C_3-C_6$ cycloalkyl, phenyl(C1–C4 alkylene) where the phenyl is optionally substituted with $C_1-C_4$ alkyl, $C_1-C_4$ alkoxy or halo, naphthyl, thienyl, furyl, benzothienyl, benzofuryl, or phenyl optionally monosubstituted with $C_1-C_4$ alkyl, $C_1-C_4$ alkoxy or halo;

$R^{11}$ is $C_1-C_4$ alkyl, $C_3-C_7$ cycloalkyl, phenyl optionally substituted with one or two substituents independently selected from the group consisting of $C_1-C_4$ alkyl, $C_1-C_4$ alkoxy, halogen, hydroxy, cyano, carbamoyl, amino, mono($C_1-C_4$ alkyl)amino, di($C_1-C_4$ alkyl)amino, $C_1-C_4$ alkylsulfonylamino, and nitro, naphthyl optionally substituted with one or two substituents independently selected from the group consisting of $C_1-C_4$ alkyl, $C_1-C_4$ alkoxy, halogen, hydroxy, cyano, carbamoyl, amino, mono($C_1-C_4$ alkyl)amino, di($C_1-C_4$ alkyl)amino, and nitro, or $C_1-C_4$ alkoxycarbonyl;

$R^{12}$ is:
  $C_1-C_4$ alkyl optionally monosubstituted with a substituent selected from the group consisting of hydroxy, protected carboxy, carbamoyl, thiobenzyl and $C_1-C_4$ thioalkyl;
  phenyl optionally substituted with one or two substituents independently selected from the group consisting of $C_1-C_4$ alkyl, $C_1-C_4$ alkoxy, halogen, hydroxy, cyano, carbamoyl, amino, mono($C_1-C_4$ alkyl)amino, di($C_1-C_4$ alkyl)amino, $C_1-C_4$ alkylsulfonylamino, and nitro;

naphthyl optionally substituted with one or two substituents independently selected from the group consisting of $C_1-C_4$ alkyl, $C_1-C_4$ alkoxy, halogen, hydroxy, cyano, carbamoyl, amino, mono($C_1-C_4$ alkyl)amino, di($C_1-C_4$ alkyl)amino, and nitro; or
  $C_1-C_4$ alkoxycarbonyl;

$R^{13}$ is:
  $C_1-C_4$ alkoxycarbonyl;
  benzyloxycarbonyl where the phenyl group is optionally substituted with one or two substituents independently selected from the group consisting of $C_1-C_4$ alkyl, $C_1-C_4$ alkoxy, halogen, cyano, nitro, amino, carbamoyl, hydroxy, mono($C_1-C_4$ alkyl)amino, and di($C_1-C_4$ alkyl)amino;
  benzoyl where the phenyl group is optionally substituted with one or two substituents selected from the group consisting of $C_1-C_4$ alkyl, $C_1-C_4$ alkoxy, halogen, hydroxy, cyano, carbamoyl, amino, mono($C_1-C_4$ alkyl)amino, di($C_1-C_4$ alkyl)amino, $C_1-C_4$ alkylsulfonylamino, and nitro; and $R^{14}$ and $R^{15}$ are:
  $C_1-C_5$ alkanoyloxy;
  benzoyloxy optionally substituted with one or two substituents independently selected from the group consisting of $C_1-C_4$ alkyl, $C_1-C_4$ alkoxy, halogen, cyano, nitro, amino and $C_1-C_4$ alkoxycarbonyl;
  benzyloxy;
  diphenylmethoxy; or
  triphenylmethoxy; or one of $R^{14}$ and $R^{15}$ is hydrogen and the other is:
  $C_1-C_5$ alkanoyloxy;
  benzoyloxy optionally substituted with one or two substituents independently selected from the group consisting of $C_1-C_4$ alkyl, $C_1-C_4$ alkoxy, halogen, cyano, nitro, amino and $C_1-C_4$ alkoxycarbonyl;
  benzyloxy;
  diphenylmethoxy; or
  triphenylmethoxy;

providing that $R^2$ may be other than hydrogen only when $R^1$ is hydroxy substituted $C_1-C_5$ alkyl; and hydrates, solvates and pharmaceutically acceptable acid addition salts thereof.

Certain compounds of Formula I are novel. A further embodiment of this invention are novel substituted 2-(azetidinon-1-yl)acetic acid derivatives of Formula II

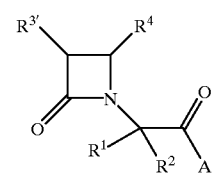

II where

A is —O—$R^9$; —S—X"; or —NR$^5$X";

$R^1$; $R^2$; $R^4$; $R^5$; $R^7$; $R^8$; $R^{10}$; $R^{11}$; $R^{12}$; $R^{13}$; $R^{14}$; $R^{15}$; and Y are as previously defined;

$R^{3'}$ is a structure selected from the group consisting of:

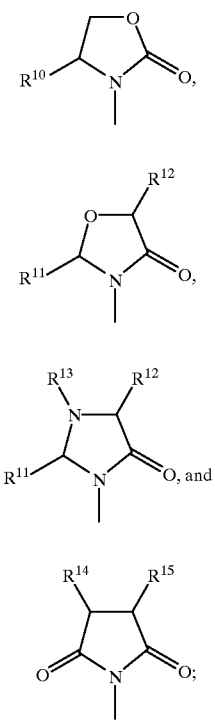

X" is $C_1-C_4$ alkylene ω-substituted with $C_1-C_4$ alkoxy, Y, (optionally substituted $C_1-C_4$ alkylene)-Y, or (optionally substituted $C_2-C_4$ alkylene)-$NR^7R^8$;

$R^5$ and X" taken together with the nitrogen to which they are attached form:
  2-(pyrrolidin-1-ylmethyl)pyrrolidin-1-yl;
  piperidinyl optionally substituted at the 4-position with hydroxy, pyrrolidin-1-yl, piperidin-1-yl, benzyl, or piperidin-1-yl(C1–C4 alkylene);
  piperidinyl mono- or disubstituted with methyl;
  piperazinyl optionally substituted at the 4-position with $C_1-C_4$ alkyl, $C_3-C_6$ cycloalkyl, phenyl, phenyl (C1–C4 alkylene), α-methylbenzyl, N-($C_1-C_4$ alkyl) acetamid-2-yl, or $C_1-C_4$ alkoxycarbonyl;
  1,2,3,4-tetrahydroisoquinolin-2-yl; or
  homopiperazinyl substituted in the 4-position with $C_1-C_4$ alkyl;

$R^9$ is $C_1-C_6$ alkyl, ($C_2-C_4$ alkylene)trimethylsilyl, or benzyl where the phenyl ring of the benzyl moiety may be optionally substituted with 1 to 3 substituents independently selected from halo, $C_1-C_4$ alkyl, $C_1-C_4$ alkoxy, nitro, amino, cyano, hydroxy, or carboxamido; providing that:

a) $R^2$ may be other than hydrogen only when $R^1$ is hydroxy substituted $C_1-C_5$ alkyl; and
b) when A is —$OR^9$, $R^1$ must be selected from the group consisting of —C(O)$NR^5X'$, ($C_1-C_4$ alkylene)C(O)$NR^5X'$, and 2,2-dimethylpropanoyl;

and solvates and pharmaceutically acceptable acid addition salts thereof.

This invention also provides a pharmaceutical formulation which comprises, in association with a pharmaceutically acceptable carrier, diluent or excipient, a compound of Formula II.

The general chemical terms used in the formulae above have their usual meanings. For example, the term "alkyl" includes such groups as methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

The term "alkoxy" includes such groups as methoxy, ethoxy, propoxy, isopropoxy, butoxy, tert-butoxy and the like.

The term "acyl" includes such groups as formyl, acetyl, propanoyl, butanoyl, pentanoyl and the like.

The term "halo" means fluoro, chloro, bromo, and iodo.

The term "cycloalkyl" means cyclopropyl, cyclobutyl, cyclopentyl, cyclohexyl, cycloheptyl, and cyclooctyl.

The term "alkanoyloxy" refers to formyloxy, acetoxy, n-propionoxy, n-butyroxy, pivaloyloxy, and like lower alkanoyloxy groups.

The term "hydroxy substituted alkyl" is taken to mean a linear or branched alkyl radical which bears a hydroxy substituent on the carbon at the point of attachment of the radical to the rest of the molecule. Such groups include hydroxymethyl, 1-hydroxyethyl, 1-hydroxypropyl, 1-hydroxy-2,2-dimethylpropyl, and the like.

The term "phenyl($C_1-C_4$ alkylene)" is taken to mean a linear or branched alkyl chain of from one to four carbons bearing as a substituent a phenyl ring. Examples of such groups include benzyl, phenethyl, phenpropyl, α-methylbenzyl and the like.

The term "optionally substituted phenyl" is taken to mean a phenyl radical optionally substituted with one or two substituents independently selected from $C_1-C_4$ alkyl, $C_1-C_4$ alkoxy, hydroxy, halo, nitro, trifluoromethyl, sulfonamido, and indol-2-yl.

The terms "(optionally substituted $C_1-C_4$ alkylene)" and "(optionally substituted $C_2-C_4$ alkylene)" are taken to mean an alkylene chain which is optionally substituted with up to two methyl groups or a $C_1-C_4$ alkoxycarbonyl group.

The term "protected amino" refers to amine protecting groups used to protect the nitrogen of the β-lactam ring during preparation or subsequent reactions. Examples of such groups are benzyl, 4-methoxybenzyl, 4-methoxyphenyl, or trialkylsilyl, for example trimethylsilyl.

The term "protected carboxy" refer to the carboxy group protected or blocked by a conventional protecting group commonly used for the temporary blocking of the acidic carboxy. Examples of such groups include lower alkyl, for example tert-butyl, halo-substituted lower alkyl, for example 2-iodoethyl and 2,2,2-trichloroethyl, benzyl and substituted benzyl, for example 4-methoxybenzyl and 4-nitrobenzyl, diphenylmethyl, alkenyl, for example allyl, trialkylsilyl, for example trimethylsilyl and tert-butyldiethylsilyl and like carboxy-protecting groups.

The term "antagonist", as it is used in the description of this invention, is taken to mean a full or partial antagonist. A compound which is a partial antagonist at the vasopressin $V_{1a}$ receptor must exhibit sufficient antagonist activity to inhibit the effects of vasopressin or a vasopressin agonist at an acceptable dose. While a partial antagonist of any intrinsic activity may be useful, partial antagonists of at least about 50% antagonist effect are preferred and partial antagonists of at least about 80% antagonist effect are more preferred. Full antagonists of the vasopressin $V_{1a}$ receptor are most preferred.

While all of the compounds of Formula I and Formula II are useful, certain classes are preferred. The following paragraphs describe such preferred classes.

aa) $R^1$ is selected from the group consisting of $C_1-C_4$ alkyl, —C(O)$NR^5X'$, -($C_1-C_4$ alkylene)C(O)$NR^5X'$, hydroxy substituted $C_1-C_5$ alkyl, $C_1-C_5$ acyl optionally substituted as the ethylene glycol ketal, and α-hydroxy-α-benzoylbenzyl;
ab) $R^1$ is $C_1$–$C_4$ alkyl;
ac) $R^1$ is isopropyl;
ad) $R^1$ is isobutyl;
ae) $R^1$ is —C(O)NR$^5$X';
af) $R^1$ is -(C$_1$–C$_4$ alkylene)C(O)NR$^5$X';
ag) $R^1$ is hydroxy substituted $C_1$–$C_5$ alkyl;
ag) $R^1$ is 1-hydroxy-2,2-dimethylpropyl;
ai) $R^1$ is $C_1$–$C_5$ acyl optionally substituted as the ethylene glycol ketal;
aj) $R^1$ is 2,2-dimethylpropanoyl;
ak) $R^1$ is acetyl ethylene glycol ketal;
al) $R^1$ is propanoyl ethylene glycol ketal;
am) $R^1$ is α-hydroxy-α-benzoylbenzyl;
an) $R^2$ is hydrogen;
ao) $R^2$ is 1-hydroxy-2,2-dimethylpropyl;
ap) $R^3$ is 4-substituted oxazolidin-2-on-3-yl;
aq) $R^3$ is 2,5-disubstituted oxazolidin-4-on-3-yl;
ar) $R^3$ is 1,2,5-trisubstituted imidazolidin-4-on-3-yl;
as) $R^3$ is 3,4-disubstituted succinimido;
at) $R^3$ is 3-substituted succinimido;
au) $R^4$ is 2-arylethen-1-yl;
av) $R^4$ is 2-phenylethen-1-yl;
aw) Q is —O—;
ax) Q is —NR$^5$—;
ay) $R^5$ is hydrogen;
az) $R^5$ is benzyl;
ba) X or X' is (optionally substituted $C_1$–$C_4$ alkylene)-Y;
bb) X or X' is —CH$_2$—Y;
bc) Y is phenyl;
bd) Y is substituted phenyl;
be) Y is phenyl monosubstituted in the 3-position;
bf) Y is quinuclidinyl;
bg) Y is tert-butyl;
bh) X or X' is (optionally substituted $C_2$–$C_4$ alkylene)-NR$^7$R$^8$;
bi) $R^7$ is $C_1$–$C_4$ alkyl;
bj) $R^8$ is $C_1$–$C_4$ alkyl;
bk) $R^7$ and $R^8$ are both methyl;
bl) $R^7$ and $R^8$ are both ethyl;
bm) $R^7$ is hydrogen and $R^8$ is 5-nitropyridin-2-yl;
bn) $R^5$ and X' taken together with the nitrogen to which they are attached form a moiety selected from the group consisting of piperidinyl substituted in the 4-position with hydroxy or piperidin-1-yl(C$_1$–C$_4$ alkylene), piperidinyl mono- or disubstituted with methyl, 1,2,3,4-tetrahydroisoquinolin-2-yl, piperazinyl substituted in the 4-position with methyl, α-methylbenzyl, or phenethyl, and homopiperazinyl substituted in the 4-position with methyl;
bo) $R^5$ and X' taken together with the nitrogen to which they are attached form piperidinyl substituted in the 4-position with hydroxy or piperidin-1-yl(C$_1$–C$_4$ alkylene);
bp) $R^5$ and X' taken together with the nitrogen to which they are attached form piperidinyl mono- or disubstituted with methyl;
bq) $R^5$ and X' taken together with the nitrogen to which they are attached form 1,2,3,4-tetrahydroisoquinolin-2-yl;
br) $R^5$ and X' taken together with the nitrogen to which they are attached form piperazinyl substituted in the 4-position with methyl, α-methylbenzyl, or phenethyl;
bs) $R^5$ and X' taken together with the nitrogen to which they are attached form homopiperazinyl substituted in the 4-position with methyl.

It will be understood that the above classes may be combined to form additional preferred classes.

Especially preferred compounds of Formulae I and II are those described by Formula III

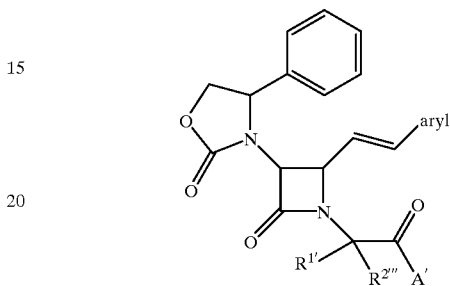

where
aryl is phenyl, 2-furyl, or 3-furyl;
$R^{1'}$ is hydrogen;
$R^{2'''}$ is selected from the group consisting of isopropyl, isobutyl, 1-hydroxy-2,2-dimethylpropyl, acetyl ethylene glycol ketal, propanoyl ethylene glycol ketal, 2,2-dimethylpropanoyl, —C(O)NR$^{5'}$X''', and -(C$_1$–C$_4$ alkylene)C(O)—NR$^{5'}$X''';
A is —O—R$^{9'}$; or —NR$^{5'}$X''';
$R^{5'}$ is hydrogen;
$R^{9'}$ is benzyl;
X''' is —CH$_2$—Y';
Y' is substituted phenyl;
$R^{5'}$ and X''' taken together with the nitrogen to which they are attached form a moiety selected from the group consisting of:
1,2,3,4-tetrahydroisoquinolin-2-yl;
piperidinyl substituted in the 4-position with hydroxy or piperidin-1-yl(C1–C4 alkylene);
piperidinyl mono- or disubstituted with methyl; and
piperazinyl substituted in the 4-position with α-methylbenzyl or phenethyl.

The compounds of the present invention are comprised of an azetidinone nucleus, said nucleus bearing asymmetric carbons at the 3- and 4-positions as illustrated in the following figure:

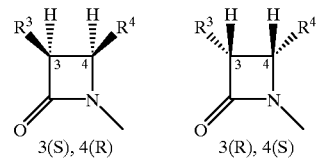

The compounds of the invention may, therefore, exist as single diastereomers, mixtures of diastereomers, or as a racemic mixture, all of which are useful and part of the invention. It is preferred that the azetidinone nucleus of the compounds of the invention exist in a single diastereomeric form. It is most preferred that the azetidinone nucleus exist as the 3(S),4(R)-diastereomer.

The skilled artisan will appreciate that, in most cases, the carbon bearing $R^1$ and $R^2$ is asymmetric. Furthermore, when $R^3$ is 4-substituted oxazolidin-2-on-3-yl, the 4-position of that ring is asymmetric. When $R^3$ is 2,5-disubstituted oxazolidin-4-on-3-yl or 1,2,5-trisubstituted imidazolidin-4-on-3-yl, the 2- and 5-carbons of those rings are asymmetric and, finally, when $R^3$ is succinimido and one of $R^{14}$ and $R^{15}$ is hydrogen, the carbon bearing the non-hydrogen substituent is also asymmetric. While compounds possessing all combinations of stereochemical purity are contemplated, it is preferred that each of these chiral centers be of a single absolute configuration.

The compounds of this invention are useful in methods for antagonism of the vasopressin $V_{1a}$ receptor for treating a variety of disorders which have been linked to this receptor in mammals. It is preferred that the mammal to be treated by the administration of compounds of this invention is human.

Since certain of the compounds of this invention are amines, they are basic in nature and accordingly react with any of a number of inorganic and organic acids to form pharmaceutically acceptable acid addition salts. Since some of the free amines of the compounds of this invention are typically oils at room temperature, it is preferable to convert the free amines to their pharmaceutically acceptable acid addition salts for ease of handling and administration, since the latter are routinely solid at room temperature. Acids commonly employed to form such salts are inorganic acids such as hydrochloric acid, hydrobromic acid, hydroiodic acid, sulfuric acid, phosphoric acid, and the like, and organic acids, such as p-toluene-sulfonic acid, methanesulfonic acid, oxalic acid, p-bromo-phenylsulfonic acid, carbonic acid, succinic acid, citric acid, benzoic acid, acetic acid and the like. Examples of such pharmaceutically acceptable salts thus are the sulfate, pyrosulfate, bisulfate, sulfite, bisulfite, phosphate, monohydrogenphosphate, dihydrogenphosphate, metaphosphate, pyrophosphate, chloride, bromide, iodide, acetate, propionate, decanoate, caprylate, acrylate, formate, isobutyrate, caproate, heptanoate, propiolate, oxalate, malonate, succinate, suberate, sebacate, fumarate, maleate, butyne-1,4-dioate, hexyne-1,6-dioate, benzoate, chlorobenzoate, methylbenzoate, dinitrobenzoate, hydroxybenzoate, methoxybenzoate, phthalate, sulfonate, xylenesulfonate, phenylacetate, phenylpropionate, phenylbutyrate, citrate, lactate, β-hydroxybutyrate, glycollate, tartrate, methanesulfonate, propanesulfonate, naphthalene-1-sulfonate, naphthalene-2-sulfonate, mandelate and the like. Preferred pharmaceutically acceptable salts are those formed with hydrochloric acid, trifluoroacetic acid, maleic acid or fumaric acid.

The following group is illustrative of compounds contemplated within the scope of this invention:

methyl 2(R)-isopropyl-2-[3(S)-(4(S)-(benzofur-7-yl)oxazolidin-2-on-3-yl)-4(R)-(1-(fur-3-yl)ethylen-2-yl)azetidin-2-on-1-yl]acetate ethyl 2(R)-isobutyl-2-[3(S)-(4(R)-(benzofur-2-yl)-oxazolidin-2-on-3-yl)-4(R)-(1-(pyrrol-2-yl)ethylen-2-yl)azetidin-2-on-1-yl]acetate propyl 2(R)-[1-hydroxy-2,2-dimethylpropyl]-2-[3(S)-(4(S)-(benzothien-5-yl)oxazolidin-2-on-3-yl)-4(R)-(1-(pyrrol-3-yl)ethylen-2-yl)azetidin-2-on-1-yl]acetate isopropyl 2(R)-[(1,1-ethyleneketal)propionyl]-2-[3(S)-(4(S)-(benzothien-5-yl)oxazolidin-2-on-3-yl)-4(R)-(1-(pyridin-2-yl)ethylen-2-yl)azetidin-2-on-1-yl]acetate butyl 2(R)-[(1,1-ethyleneketal)acetyl]-2-[3(S)-(4(S)-(benzothien-3-yl)oxazolidin-2-on-3-yl)-4(R)-(1-(pyridin-3-yl)ethylen-2-yl)azetidin-2-on-1-yl]acetate isobutyl 2(R)-[2,2-dimethylpropionyl]-2-[3(S)-(4(S)-(fur-3-yl)oxazolidin-2-on-3-yl)-4(R)-(1-(pyridin-4-yl)ethylen-2-yl)azetidin-2-on-1-yl]acetate sec-butyl 2(R)-[N-benzylcarboxamido]-2-[3(R)-(4(S)-(thien-2-yl)oxazolidin-2-on-3-yl)-4(S)-(1-(thiazol-2-yl)ethylen-2-yl)azetidin-2-on-1-yl]acetate tert-butyl 2(R)-[N-(3-trifluoromethyl)benzylcarboxamido]-2-[3(S)-(naphth-2-yl)-4(R)-(1-(thiazol-4-yl)ethylen-2-yl)azetidin-2-on-1-yl]acetate pentyl 2(R)-[N-(3-amino)benzylacetamido-2-yl]-2-[3(S)-(4(S)-(phenpropyl)oxazolidin-2-on-3-yl)-4(R)-(1-(thiazol-5-yl)ethylen-2-yl)azetidin-2-on-1-yl]acetate hexyl 2(R)-[N-(2-trifluoromethyl)benzylacetamido-2-yl]-2-[3(S)-(4(S)-(phenethyl)oxazolidin-2-on-3-yl)-4(R)-(1-(oxazol-2-yl)ethylen-2-yl)azetidin-2-on-1-yl]acetate benzyl 2(R)-[N-(2-carboxamido)benzylpropionamido-3-yl]-2-[3(S)-(4(S)-(3-isopropylbenzyl)oxazolidin-2-on-3-yl)-4(R)-(1-(oxazol-4-yl)ethylen-2-yl)azetidin-2-on-1-yl]acetate 2-chlorobenzyl 2(R)-[N-(4-trifluoromethyl)benzylpropionamido-3-yl]-2-[3(R)-(4(S)-(4-fluorobenzyl)oxazolidin-2-on-3-yl)-4(S)-(1-(oxazol-5-yl)ethylen-2-yl)azetidin-2-on- 1-yl]acetate 3-fluorobenzyl 2(R)-[N-(4-nitro)benzylbutanamido-4-yl]-2-[3(S)-(4(S)-(benzyl)oxazolidin-2-on-3-yl)-4(R)-(1-(isoxazol-3-yl)ethylen-2-yl)azetidin-2-on-1-yl]acetate 4-iodobenzyl 2(R)-[N-(3-fluoromethyl)benzylbutanamido-4-yl]-2-[3(S)-(4(S)-(4-methoxyphenyl)oxazolidin-2-on-3-yl)-4(R)-(1-(isoxazol-4-yl)ethylen-2-yl)azetidin-2-on-1-yl]acetate 3,4-dibromobenzyl 2(R)-[N-(2-methoxy)benzylpentanamido-5-yl]-2-[3(S)-(4(S)-(3-chlorophenyl)oxazolidin-2-on-3-yl)-4(R)-(1-(isoxazol-5-yl)ethylen-2-yl)azetidin-2-on-1-yl]acetate 2-methylbenzyl 2(R)-[N-(4-methyl)benzylpentanamido-5-yl]-2-[3(S)-(4(S)-(2-ethylphenyl)oxazolidin-2-on-3-yl)-4(R)-(1-(imidazol-2-yl)ethylen-2-yl)azetidin-2-on-1-yl]acetate 3-ethylbenzyl 2(S)-isopropyl-2-[3(S)-(4(R)-phenyloxazolidin-2-on-3-yl)-4(R)-(1-(imidazol-4-yl)ethylen-2-yl)azetidin-2-on-1-yl]acetate 4-isopropylbenzyl 2(S)-isobutyl-2-[3(S)-(4(S)-cyclopropyloxazolidin-2-on-3-yl)-4(R)-(1-(imidazol-5-yl)ethylen-2-yl)azetidin-2-on-1-yl]acetate 3-bromo-4-tert-butylbenzyl 2(S)-[1-hydroxy-2,2-dimethylpropyl]-2-[3(S)-(4(S)-cyclobutyloxazolidin-2-on-3-yl)-4(R)-(1-(pyrazol-3-yl)ethylen-2-yl)azetidin-2-on-1-yl]acetate 4-methoxybenzyl 2(S)-[(1,1-ethylene)ketalpropionyl]-2-[3(R)-(4(S)-cyclopentyloxazolidin-2-on-3-yl)-4(S)-(1-(pyrazol-4-yl)ethylen-2-yl)azetidin-2-on-1-yl]acetate 3-ethoxybenzyl 2(S)-[1,1-ethyleneketal)acetyl-2-[3(S)-(4(S)-cyclohexyloxazolidin-2-on-3-yl)-4(R)-(1-(pyrazol-5-yl)ethylen-2-yl)azetidin-2-on-1-yl]acetate 2-isopropylbenzyl 2(S)-[2,2-dimethylpropionyl]-2-[3(S)-(4(S)-hexyloxazolidin-2-on-3-yl)-4(R)-(1-(pyrimidin-2-yl)ethylen-2-yl)azetidin-2-on-1-yl]acetate 3-tert-butyl-4-chlorobenzyl 2(S)-[N-benzylcarboxamido]-2-[3(R)-(4(S)-methyloxazolidin-2-on-3-yl)-4(S)-(1-(pyrimidin-4-yl)ethylen-2-yl)azetidin-2-on-1-yl]acetate 4-nitrobenzyl 2(S)-[N-(3-trifluoromethyl)benzylcarboxamido]-2-[3(S)-(4(S)-tertbutyloxazolidin-2-on-3-yl)-4(R)-(1-(pyrimidin-5-yl) ethylen-2-yl)azetidin-2-on-1-yl]acetate 3-aminobenzyl 2(S)-[N-(3-methylamino) benzylacetamido-2-yl]-2-[3(S)-(4(S)-isobutyloxazolidin-2-on-3-yl)-4(R)-(1-(pyrimidin-6-yl)ethylen-2-yl)azetidin-2-on-1-yl]acetate 4-methyl-3,5-dichlorobenzyl 2(S)-[N-(3-dimethylamino)-benzylacetamido-2-yl]-2-[3(S)-(4(S)-butyloxazolidin-2-on-3-yl)-4(R)-(1-(thiadiazol-3-yl) ethylen-2-yl)azetidin-2-on-1-yl]acetate 2-cyanobenzyl 2(S)-[N-(2-trifluoromethyl) benzylpropionamido-3-yl]-2-[3(S)-(4(S)-isopropyloxazolidin-2-on-3-yl)-4(R)-(1-(oxadiazol-3-yl)ethylen-2-yl)azetidin-2-on-1-yl]acetate 4-hydroxybenzyl 2(S)-[N-(3-carboxamido) benzylpropionamido-3-yl]-2-[3(S)-(4(S)-propyloxazolidin-2-on-3-yl)-4(R)-(1-(quinolin-2-yl) ethylen-2-yl)azetidin-2-on-1-yl]acetate 3-carboxamidobenzyl 2(S)-[N-(4-trifluoromethyl) benzylbutanamido-4-yl]-2-[3(S)-(4(S)-ethyloxazolidin-2-on-3-yl)- 4(R)-(1-(quinolin-3-yl) ethylen-2-yl)azetidin-2-on-1-yl]acetate 2,4,5-trichlorobenzyl 2(S)-[N-(2-nitro) benzylbutanamido-4-yl]-2-[3(S)-(4(S)-methyloxazolidin-2-on-3-yl)-4(R)-(1-(quinolin-4-yl) ethylen-2-yl)azetidin-2-on-1-yl]acetate N-[phenyl]-2(S)-[N-(2-fluoro-3-methyl) benzylbutanamido-4-yl]-2-[3(S)-(2-(6-nitronaphth-2-yl)-5-(methyl)-oxazolidin-4-on-3-yl)-4(R)-(1-(quinolin-5-yl)ethylen-2-yl)azetidin-2-on-1-yl] acetamide N-[3-trifluoromethylbenzyl]-2(S)-[N-(4-methoxy) benzylpentanamido-5-yl]-2-[3(S)-(2-(6-cyanonaphth-2-yl)-5-(hydroxymethyl)oxazolidin-4-on-3-yl)-4(R)-(1-(quinolin-6-yl)ethylen-2-yl)azetidin-2-on-1-yl] acetamide N-[cyclopropyl)-2(S)-[N-(4-isopropyl) benzylpentanamido-5-yl]-2-[3(S)-(2-(4-methylnaphth-2-yl)-5-ethyloxazolidin-4-on-3-yl)-4(R)-(1-(quinolin-7-yl)ethylen-2-yl)azetidin-2-on-1-yl]acetamide N-[cyclobutylethyl]-2(R,S)-isopropyl-2-[3(S)-2-(naphth-2-yl)-5-(2-(methoxycarbonyl)ethyl)oxazolidin-4-on-3-yl)-4(R)-(1-(quinolin-8-yl)ethylen-2-yl)azetidin-2-on-1-yl]acetamide N-[cyclopentyl]-2(R,S)-isobutyl-2-[3(S)-(5-methoxynaphth-1-yl)-5-(2-(benzyloxycarbonyl) ethyloxazolidin-4-on-3-yl)-4(R)-(1-(isoquinolin-1-yl) ethylen-2-yl)azetidin-2-on-1-yl]acetamide N-[phenethyl]-2(R,S)-[1-hydroxy-2,2-dimethylpropyl]-2-[3(S)-(2-(3-chloro-1-naphthyl)-5-((phenoxycarbonyl)ethyl)-oxazolidin-4-on-3-yl)-4 (R)-(1-(isoquinolin-3-yl)ethylen-2-yl)azetidin-2-on-1-yl] acetamide N-[phenpropyl]-2(R,S)-[(1,1-ethyleneketal)propionyl]-2-[3(S)-(2-(naphth-1-yl)-5-(propyl)oxazolidin-4-on-3-yl)-4(R)-(1-(isoquinolin-4-yl)ethylen-2-yl)azetidin-2-on-1-yl]acetamide N-[3-trifluoromethylbenzyl]-2(R,S)-[(1,1-ethyleneketal)-acetyl]-2-[3(S)-(2-(3-nitrophenyl)-5-((3-thiobenzyl)-propyl)oxazolidin-4-on-3-yl)-4(R)-(1-(isoquinolin-5-yl)-ethylen-2-yl)azetidin-2-on-1-yl]acetamide N-[4-chlorobenzyl]-2(R,S)-[2,2-dimethylpropionyl]-2-[3(S)-(2-(3-nitrophenyl)-5-((3-thiobenzyl)propyl)oxazolidin-4-on-3-yl)-4(R)-(1-(isoquinolin-6-yl)ethylen-2-yl) azetidin-2-on-1-yl]acetamide N-[2-bromobenzyl]-2(R,S)-[N-benzylcarboxamido]-2-[3 (S)-(2-(4-methanesulfonylphenyl)-5-(isopropyl) oxazolidin-4-on-3-yl)-4(R)-(1-(isoquinolin-7-yl) ethylen-2-yl)azetidin-2-on-1-yl]acetamide N-[3-fluorobenzyl]-2(R,S)-[N-(3-trifluoromethyl) benzylcarboxamido]-2-[3(S)-(2-(3-aminophenyl)-5-(butyl)oxazolidin-4-on-3-yl)-4(R)-(1-(isoquinolin-8-yl)ethylen-2-yl)azetidin-2-on-1-yl]acetamide N-[2-methylbenzyl]-2(R,S)-[N-phenylcarboxamido]-2-[3 (S)-(2-(2-cyanophenyl)-5-((3-thiomethyl)butyl) oxazolidin-4-on-3-yl)-4(R)-(1-(naphth-1-yl)ethylen-2-yl)azetidin-2-on-1-yl]acetamide N-[3-chloro-4-isopropylbenzyl]-2(R,S)-[N-(2-chlorophenyl)carboxamido]-2-[3(S)-(2-(4-hydroxyphenyl)-5-(isobutyl)oxazolidin-4-on-3-yl)-4(R)-(1-(naphth-2-yl)ethylen-2-yl)azetidin-2-on-1-yl] acetamide N-[2,4-dimethoxybenzyl]-2(R,S)-[N-(4-methylphenyl) carboxamido]-2-[3(S)-(2-(2-fluoro-4-methoxyphenyl)-5-(phenyl)-oxazolidin-4-on-3-yl)-4(R)-(1-(2-fluorophenyl)ethylen-2-yl)azetidin-2-on-1-yl] acetamide N-[3-isopropoxybenzyl]-2(R,S)-[N-(3-isopropylphenyl) carboxamido]-2-[3(S)-(2-(3-ethoxyphenyl)-5-(2-methylphenyl)oxazolidin-4-on-3-yl)-4(R)-(1-(3-chlorophenyl)ethylen-2-yl)azetidin-2-on-1-yl] acetamide N-[4-sulfonamidobenzyl]-2(R,S)-[N-(4-trifluoromethylphenyl)carboxamido]-2-[3(S)-(2-(2-methoxyphenyl)-5-(3-ethoxyphenyl)oxazolidin-4-on-3-yl)-4(R)-(1-(4-bromophenyl)-ethylen-2-yl)azetidin-2-on-1-yl]acetamide N-[quinuclidin-2-yl]-2(R,S)-[N-(4-methylphenyl) carboxamido]-2-[3(S)-(2-(3-isopropylphenyl)-5-(4-chlorophenyl)-oxazolidin-4-on-3-yl)-4(R)-(1-(3-iodophenyl)ethylen-2-yl)azetidin-2-on-1-yl]acetamide 1-{2(R,S)-[N-(3-trifluoromethylbenzyl)acetamido-2-yl]-2-[3(S)-(2-(2-chloro-4-bromophenyl)-5-(2-ethyl-3-bromophenyl)-oxazolidin-4-on-3-yl)-4(R)-(1-(2-methylphenyl)ethylen-2-yl)azetidin-2-on-1-yl]}-1,2,3,4-tetrahydronaphthalene 1-{2(R,S)-[N-(benzyl)acetamido-2-yl]-2-[3(S)-(2-(2-chloro-4-bromophenyl)-5-(2-ethyl-3-bromophenyl) oxazolidin-4-on-3-yl)-4(R)-(1-(3-isopropylphenyl) ethylen-2-yl)azetidin-2-on-1-yl]}-4-hydroxypiperidine 1-{2(R,S)-[N-(4-chlorophenyl)acetamido-2-yl]-2-[3(S)-(2-(3-iodophenyl)-5-(3-hydroxyphenyl)oxazolidin-4-on-3-yl)-4(R)-(1-(4-pentylphenyl)ethylen-2-yl) azetidin-2-on-1-yl]}4-(piperidin-1-yl)piperidine 1-{2(R,S)-[N-(2-cyanophenyl)acetamido-2-yl]-2-3(R)-(2-(4-fluorophenyl)-5-(4-cyanophenyl)oxazolidin-4-on-3-yl)-4(S)-(1-(2-propoxyphenyl)ethylen-2-yl) azetidin-2-on-1-yl]}-4-benzylpiperidine 1-{2(R,S)-[N-(phenylethyl)acetamido-2-yl]-2-[3(S)-(2-(phenyl)-5-(3-dimethylaminophenyl)oxazolidin-4-on-3-yl)-4(R)-(1-(3-methoxyphenyl)ethylen-2-yl) azetidin-2-on-1-yl]}-4-((piperidin-1-yl)methyl) piperidine 1-{2(R,S)-[N-(benzyl)propionamido-3-yl]-2-[3(S)-(2-(methoxycarbonyl)-5-(4-ethylaminophenyl) oxazolidin-4-on-3-yl)-4(R)-(1-(4-isobutoxyphenyl) ethylen-2-yl)azetidin-2-on-1-yl]}-4-(2-(piperidin-1-yl) ethyl)piperidine 1-{2(R,S)-[N-(3-trifluoromethylbenzyl)propionamido-3-yl]-2-[3(R)-(2-(isobutoxycarbonyl)-5-(2- methanesulfonylaminophenyl)oxazolidin-4-on-3-yl)-4 (S)-(1-(2-ethylthiophenyl)-ethylen-2-yl)azetidin-2-on-1-yl]}-4-(3-(piperidin-1-yl)propyl)piperidine 1-{2(R,S)-[N-(3-fluorophenyl)propionamido-3-yl]-2-[3 (S)-(2-(cyclohexyl)-5-(3-nitrophenyl)oxazolidin-4-on-3-yl)-4(R)-(1-(3-hexylthiophenyl)ethylen-2-yl) azetidin-2-on-1-yl]}-4-(4-(piperidin-1-yl)butyl) piperidine 1-{2(R,S)-[N-(3-aminophenyl)propionamido-3-yl]-2-[3 (S)-(2-(cyclopentyl)-5-(methoxycarbonyl)oxazolidin-4-on-3-yl)-4(R)-(1-(4-methylthiophenyl)ethylen-2-yl) azetidin-2-on-1-yl]}-2,4-dimethylpiperidine 1-{2(R,S)-[N-(benzyl)propionamido-3-yl]-2-[3(S)-(2-(cyclopropyl)-5-(ethoxycarbonyl)oxazolidin-4-on-3-yl)-4(R)-(1-(2-nitrophenyl)ethylen-2-yl)azetidin-2-on-1-yl]}- 3,5-dimethylpiperidine 1-{2(R,S)-[N-(3-methylbenzyl)propionamido-3-yl]-2-[3 (S)-(2-(sec-butyl)-5-(tert-butoxycarbonyl)oxazolidin-4-on-3-yl)-4(R)-(1-(3-nitrophenyl)ethylen-2-yl) azetidin-2-on-1-yl]}-4-methylpiperidine 1-{2(R,S)-[N-(4-isopropoxybenzyl)propionamido-3-yl]-2-[3(S)-(2-(butyl)-5-(naphth-1-yl)oxazolidin-4-on-3-yl)-4(R)-(1-(4-nitrophenyl)ethylen-2-yl)azetidin-2-on-1-yl]}-4-isopropylpiperazine 1-{2(R,S)-[N-(3-iodobenzyl)propionamido-3-yl]-2-[3 (S)-(2-(isopropyl)-5-(naphth-2-yl)oxazolidin-4-on-3-yl)-4(R)-(1-(2-carboxyphenyl)ethylen-2-yl)azetidin-2-on-1-yl]}-4-phenethylpiperazine 1-{2(R,S)-[N-(phenethyl)propionamido-3-yl]-2-[3(S)-(2-(propyl)-5-(3-chloronaphth-1-yl)oxazolidin-4-on-3-yl)-4(R)-(1-(3-carboxamidophenyl)ethylen-2-yl) azetidin-2-on-1-yl]}-4-cyclohexylpiperazine 1-{2(R,S)-[N-(benzyl)butanamido-4-yl]-2-[3(S)-(2-(ethyl)-5-(6-methoxynaphth-2-yl)oxazolidin-4-on-3-yl)-4(R)-(1-(2,3-difluorophenyl)ethylen-2-yl)azetidin-2-on-1-yl]}-4-cyclopropylpiperazine 1-{2(R,S)-[N-(3-trifluoromethylbenzyl)butanamido-4-yl]-2-[3(S)-(2-(methyl)-5-(5-aminonaphth-1-yl) oxazolidin-4-on-3-yl)-4(R)-(1-(3,5-dichlorophenyl) ethylen-2-yl)azetidin-2-on-1-yl]}-4-benzylpiperazine 1-{2(R,S)-[N-(2-bromobenzyl)butanamido-4-yl]-2-[3(S)-(2-(isobutoxycarbonyl)-3-(methoxycarbonyl)-4-(3-dimethylaminophenyl)imidazolidin-5-on-1-yl)-4(R)-(1-(3-chloro- 4-bromophenyl)ethylen-2-yl)azetidin-2-on-1-yl]}-4-phenpropylpiperazine 1-{2(R,S)-[N-(phenyl)butanamido-4-yl]-2-[3(S)-(2-(cyclohexyl)-3-(ethoxycarbonyl)-4-(4-ethylaminophenyl)-imidazolidin-5-on-1-yl)-4(R)-(1-(5,6-dichloro-3-iodophenyl)-ethylen-2-yl)azetidin-2-on-1-yl]}-4-phenylpiperazine 1-{2(R,S)-[N-(phenethyl)butanamido-4-yl]-2-[3(S)-(2-(cyclopentyl)-3-(propoxycarbonyl)-4-(2-methanesulfonylaminophenyl)imidazolidin-5-on-1-yl)-4(R)-(1-(2,4-dimethyl-phenyl)ethylen-2-yl) azetidin-2-on-1-yl]}-4-methoxycarbonylpiperazine 1-{2(R,S)-[N-(benzyl)pentanamido-5-yl]-2-[3(S)-(2-(cyclopropyl)-3-(isopropoxycarbonyl)-4-(3-nitrophenyl)-imidazolidin-5-on-1-yl)-4(R)-(1-(3-methyl-4-isopropylphenyl)-ethylen-2-yl)azetidin-2-on-1-yl]56 }-4-(2-(piperidin-1-yl)ethyl)piperidine naphthalenesulfonate 1-{2(R,S)-[N-(3-trifluoromethylbenzyl)pentanamido-5-yl]-2-[3(S)-(2-(sec-butyl)-3-(butoxycarbonyl)-4-(methoxycarbonyl)imidazolidin-5-on-1-yl)-4(R)-(1-(2-chloro-4-pentylphenyl)ethylen-2-yl)azetidin-2-on-1-yl]}-4-(2-(piperidin-1-yl)ethyl)piperidine oxalate 1-{2(R,S)-[N-(4-carboxamidobenzyl)pentanamido-5-yl]-2-[3(S)-(2-(butyl)-3-(isobutoxycarbonyl)-4-(ethoxycarbonyl)-imidazolidin-5-on-1-yl)-4(R)-(1-(2-methyl-3-propoxyphenyl)-ethylen-2-yl)azetidin-2-on-1-yl]}-4-(2-(piperidin-1-yl)ethyl)piperidine maleate 1-{2(R,S)-[N-(3-methoxybenzyl)pentanamido-5-yl]-2-[3 (S)-(2-(isopropyl)-3-(tert-butoxycarbonyl)-4-(tert-butoxycarbonyl)imidazolidin- 5-on-1-yl)-4(R)-(1-(3,4-dimethoxyphenyl)ethylen-2-yl)azetidin-2-on-1-yl]}-4-(2-(piperidin-1-yl)ethyl)piperidine citrate 1-{2(R,S)-[N-(phenyl)pentanamido-5-yl]-2-[3(S)-(2-(propyl)-3-(benzyloxycarbonyl)-4-(naphth-1-yl) imidazolidin-5-on-1-yl)-4(R)-(1-(2,3-dibromo-4-isobutoxyphenyl)ethylen-2-yl)azetidin-2-on-1-yl]}-4-(2-(piperidin-1-yl)ethyl)piperidine phosphate 1-{2(R,S)-[N-phenethyl)pentanamido-5-yl]-2-[3(S)-(2-(ethyl)-3-(2-methylbenzyloxycarbonyl)-4-(naphth-2-yl)imidazolidin-5-on-1-yl)-4(R)-(2-ethylthio-4-methylphenyl)ethylen-2-yl)azetidin-2-on-1-yl]}-4-(2-(piperidin-1-yl)ethyl)piperidine acetate 1-{2(R,S)-[N-(2,4-dichlorophenyl)pentanamido-5-yl]-2-[3(S)-(2-(methyl)-3-(4-isopropylbenzyloxycarbonyl)-4-(3-chloronaphth-1-yl)imidazolidin-5-on-1-yl)-4(R)-(1-(2-chloro-5-isopropyl-3-hexylthiophenyl)ethylen-2-yl)azetidin-2-on-1-yl]}-4-(2-(piperidin-1-yl)ethyl) piperidine trifluoroacetate 1-{2(R,S)-[N-methyl-N-(benzyl)pentanamido-5-yl]-2-[3 (R)-(2-(tert-butyl)-3-(3-methoxybenzyloxycarbonyl)-4-(6-methoxynaphth-2-yl)imidazolidin-5-on-1-yl)-4 (S)-(1-(3,4-dimethylthiophenyl)ethylen-2-yl)azetidin-2-on-1-yl]}-4-(2-(piperidin-1-yl)ethyl)piperidine benzoate 1-{2(R,S)-[N-hydroxy-N-(benzyl)pentanamido-5-yl]-2-[3(R)-(2-(isobutyl)-3-(2-butoxybenzyloxycarbonyl)-4-(5-aminonaphth-1-yl)imidazolidin-5-on-1-yl)-4(S)-(1-(2-nitro-4-methoxyphenyl)ethylen-2-yl)azetidin-2-on-1-yl]}-4-(2-(piperidin-1-yl)ethyl)piperidine 4-toluenesulfonate 1-{2(R,S)-[N-(2-chlorophenyl)pentanamido-5-yl]-2-[3 (S)-(2-(6-nitronaphth-2-yl)-3-(3-chlorobenzyloxycarbonyl)-4-(methyl)imidazolidin-5-on-1-yl)-4(R)-(1-(3-nitro-5-chlorophenyl)ethylen-2-yl) azetidin-2-on-1-yl]}-4-(2-(piperidin-1-yl)ethyl) piperidine trifluoromethanesulfonate 1-{2(R,S)-[N-(3-chloro-4-methoxyphenyl)pentanamido-5-yl]-2-[3(S)-(2-(7-cyanonaphth-2-yl)-3-(3-fluoro-5-methoxybenzyloxycarbonyl)-4-(hydroxymethyl) imidazolidin-5-on-1-yl)-4(R)-(1-(4-nitro-3-methylphenyl)ethylen-2-yl)azetidin-2-on-1-yl]}-4-(2-(piperidin-1-yl)ethyl)piperidine methanesulfonate 1-{2(R,S)-[N-(4-aminobenzyl)pentanamido-5-yl]-2-[3 (S)-(2-(4-methylnaphth-2-yl)-3-(3-cyanobenzyloxycarbonyl)-4-(ethyl)imidazolidin-5-on-1-yl)-4(R)-(1-(3-methoxy-4-carboxyphenyl)ethylen-2-yl)azetidin-2-on-1-yl]}-4-(2-(piperidin-1-yl)ethyl) piperidine 1-{2(R,S)-[N-(2-hydroxybenzyl)pentanamido-5-yl]-2-[3 (S)-(2-(naphth-2-yl)-3-(4-nitrobenzyoxycarbonyl)-4-(2-(methoxycarbonyl)ethyl)imidazolidin-5-on-1-yl)-4 (R)-(1-(3-carboxamido-4-isopropylphenyl)ethylen-2-yl)azetidin-2-on-1-yl]}-4-(2-(piperidin-1-yl) piperidine hydrochloride methyl 2(R)-isopropyl-2-[3(S)-(2-(5-methoxynaphth-1-yl)-3-(3-aminobenzyloxycarbonyl)-4-(2-(benzyloxycarbonyl)ethyl)-imidazolidin-5-on-1-yl)-4 (R)-(1-(fur-3-yl)ethylen-2-yl)azetidin-2-on-1-yl] acetate ethyl 2(R)-isobutyl-2-[3(S)-(2-(3-chloronaphth-1-yl)-3-(2-hydroxybenzyloxycarbonyl)-4-(3-(tert-butoxycarbonyl)-propyl)imidazolidin-5-on-1-yl)-4(R)-(1-(pyrrol-2-yl)ethylen-2-yl)azetidin-2-on-1-yl]acetate propyl 2(R)-[1-hydroxy-2,2-dimethylpropyl]-2-[3(S)-(2-(naphth-1-yl)-3-(3-ethylaminobenzyloxycarbonyl)-4-(2-(isobutoxycarbonyl)propyl)imidazolidin-5-on-1-yl)-4(R)-(1-(pyrrol-3-yl)ethylen-2-yl)azetidin-2-on-1-yl]acetate isopropyl 2(R)-[(1,1-ethyleneketal)propionyl]-2-[3(S)-(2-(3-nitrophenyl)-3-(4-dimethylaminobenzyloxycarbonyl)-4-(2-(phenoxycarbonyl)ethyl)imidazolidin-5-on-1-yl)-4(R)-(1-(pyridin-2-yl)ethylen-2-yl)azetidin-2-on-1-yl]acetate butyl 2(R)-[(1,1-ethyleneketal)acetyl]-2-[3(S)-(2-(4-methanesulfonylaminophenyl)-3-(benzoyl)-4-(propyl)imidazolidin-5-on-1-yl)-4(R)-(1-(pyridin-3-yl)ethylen-2-yl)azetidin-2-on-1-yl]acetate isobutyl 2(R)-[2,2-dimethylpropionyl]-2-[3(S)-(2-(3-aminophenyl)-3-(3-methylbenzoyl)-4-(thiobenzyl)propyl)-imidazolidin-5-on-1-yl)-4(R)-(1-(pyridin-4-yl)ethylen-2-yl)azetidin-2-on-1-yl]acetate sec-butyl 2(R)-[N-benzylcarboxamido]-2-[3(R)-(2-(2-cyanophenyl)-3-(4-tert-butylbenzoyl)-4-(isopropyl)imidazolidin-5-on-1-yl)-4(S)-(1-(thiazol-2-yl)ethylen-2-yl)azetidin-2-on-1-yl]acetate tert-butyl 2(R)-[N-(3-trifluoromethyl)benzylcarboxamido]-2-[3(S)-(2-(4-hydroxyphenyl)-3-(2-isopropoxybenzoyl)-4-(butyl)imidazolidin-5-on-1-yl)-4(R)-(1-(thiazol-4-yl)ethylen-2-yl)azetidin-2-on-1-yl]acetate pentyl 2(R)-[N-(3-amino)benzylacetamido-2-yl]-2-[3(S)-(2-(2-fluoro-4-methoxyphenyl)-3-(5-fluoro-3-ethoxyphenyl)-4-(3-(thiomethyl)butyl)imidazolidin-5-on-1-yl)-4(R)-(1-(thiazol-5-yl)ethylen-2-yl)azetidin-2-on-1-yl]acetate hexyl 2(R)-[N-(2-trifluoromethyl)benzylacetamido-2-yl]-2-[3(S)-(2-(3-ethoxyphenyl)-3-(4-chlorobenzoyl)-4-(isobutyl)imidazolidin-5-on-1-yl)-4(R)-(1-(oxazol-2-yl)ethylen-2-yl)azetidin-2-on-1-yl]acetate benzyl 2(R)-[N-(2-carboxamido)benzylpropionamido-3-yl]-2-[3(S)-(2-(3-methoxyphenyl)-3-(2,4-dibromobenzoyl)-4-(phenyl)imidazolidin-5-on-1-yl)-4(R)-(1-(oxazol-4-yl)ethylen-2-yl)azetidin-2-on-1-yl]acetate 2-chlorobenzyl 2(R)-[N-(4-trifluoromethyl)benzylpropionamido-3-yl]-2-[3(R)-(2-(3isopropxyphenyl)-3-(4-cyanobenzoyl)-4-(2-nitrophenyl)imidazolidin-5-on-1-yl)-4(S)-(1-(oxazol-5-yl)ethylen-2-yl)azetidin-2-on-1-yl]acetate 3-fluorobenzyl 2(R)-[N-(4-nitro)benzylbutanamido-4-yl]-2-[3(S)-(2-(2-chloro-4-bromophenyl)-3-(3-nitrobenzoyl)-4-(3-ethoxyphenyl)imidazolidin-5-on-1-yl)-4(R)-(1-(isoxazol-3-yl)ethylen-2-yl)azetidin-2-on-1-yl]acetate 4-iodobenzyl 2(R)-[N-(3-fluoromethyl)benzylbutanamido-4-yl]-2-[3(S)-(2-(3-iodophenyl)-3-(2-aminobenzoyl)-4-(4-chlorophenyl)imidazolidin-5-on-1-yl)-4(R)-(1-(isoxazol-5-yl)ethylen-2-yl)azetidin-2-on-1-yl]acetate 3,4-dibromobenzyl 2(R)-[N-(2-methoxy)benzylpentanamido-5-yl]-2-[3(S)-(2-(4-fluorophenyl)-3-(3-hydroxybenzoyl)-4-(2-ethyl-3-bromophenyl)imidazolidin-5-on-1-yl)-4(R)-(1-(isoxazol-5-yl)ethylen-2-yl)azetidin-2-on-1-yl]acetate 2-methylbenzyl 2(R)-[N-(4-methyl)benzylpentanamido-5-yl]-2-[3(S)-(2-(phenyl)-3-(4-dimethylaminobenzoyl)-4-(3-hydroxyphenyl)imidazolidin-5-on-1-yl)-4(R)-(1-(imidazol-2-yl)ethylen-2-yl)azetidin-2-on-1-yl]acetate 3-ethylbenzyl 2(S)-isopropyl-2-[3(S)-(2-(methoxycarbonyl)-3-(3-methanesulfonylaminobenzoyl)-4-(4-cyanophenyl)-imidazolidin-5-on-1-yl)-4(R)-(1-(imidazol-4-yl)ethylen-2-yl)azetidin-2-on-1-yl]acetate 4-isopropylbenzyl 2(S)-isobutyl-2-[3(S)-(3,4-di(acetyloxy)succinimido)-4(R)-(1-(imidazol-5-yl)ethylen-2-yl)azetidin-2-on-1-yl]acetate 3-bromo-4-tert-butylbenzyl 2(S)-[1-hydroxy-2,2-dimethylpropyl]-2-[3(S)-(3,4-di(isopropionyloxyl)succinimido)-4(R)-(1-(pyrazol-3-yl)ethylen-2-yl)azetidin-2-on-1-yl]acetate 4-methoxybenzyl 2(S)-[(1,1-ethylene)ketalpropionyl]-2-[3(R)-(3,4-di(tert-butanoyloxy)succinimido)-4(S)-(1-(pyrazol-4-yl)ethylen-2-yl)azetidin-2-on-1-yl]acetate 3-ethoxybenzyl 2(S)-[1,1-ethyleneketal)acetyl-2-[3(S)-4(R)-(1-(pyrazol-5-yl)ethylen-2-yl)azetidin-2-on-1-yl]acetate 2-isopropylbenzyl 2(S)-[2,2-dimethylpropionyl]-2-[3(S)-(3,4-di(pentanoyloxy)succinimido)-4(R)-(1-(pyrimidin-2-yl)ethylen-2-yl)azetidin-2-on-1-yl]acetate 3-tert-butyl-4-chlorobenzyl 2(S)-[N-benzylcarboxamido]-2-[3(R)-(3,4-di(benzoyloxy)succinimido)-4(S)-(1-(pyrimidin-4-yl)ethylen-2-yl)azetidin-2-on-1-yl]acetate 4-nitrobenzyl 2(S)-[N-(3-trifluoromethyl)benzylcarboxamido]-2-[3(S)-(3,4-di(2-methylbenzoyloxy)succinimido)-4(R)-(1-(pyrimidin-5-yl)ethylen-2-yl)azetidin-2-on-1-yl]acetate 3-aminobenzyl 2(S)-[N-(3-methylamino)benzylacetamido-2-yl]-2-[3(S)-(3,4-di(3-ethylbenzoyloxy)succinimido)-4(R)-(1-(pyrimidin-6-yl)ethylen-2-yl)azetidin-2-on-1-yl]acetate 4-methyl-3,5-dichlorobenzyl 2(S)-[N-(3-dimethylamino)-benzylacetamido-2-yl]-2-[3(S)-(3,4-di(4-isobutylbenzoyloxy)-succinimido)-4(R)-(1-(thiadiazol-3-yl)ethylen-2-yl)azetidin-2-on-1-yl]acetate 2-cyanobenzyl 2(S)-[N-(2-trifluoromethyl)benzylpropionamido-3-yl]-2-[3(S)-(3,4-di(3,5-dimethylbenzoyloxy)-succinimido)-4(R)-(1-(oxadiazol-3-yl)ethylen-2-yl)azetidin-2-on-1-yl]acetate 4-hydroxybenzyl 2(S)-[N-(3-carboxamido)benzylpropionamido-3-yl]-2-[3(S)-(3,4-di(2-methoxybenzoyloxy)succinimido)-4(R)-(1-(quinolin-2-yl)ethylen-2-yl)azetidin-2-on-1-yl]acetate 3-carboxamidobenzyl 2(S)-[N-(4-trifluoromethyl)benzylbutanamido-4-yl]-2-[3(S)-(3,4-di(3-tert-butoxybenzoyloxy)succinimido)-4(R)-(1-(quinolin-3-yl)ethylen-2-yl)azetidin-2-on-1-yl]acetate 2,4,5-trichlorobenzyl 2(S)-[N-(2-nitro)benzylbutanamido-4-yl]-2-[3(S)-(3,4-di(3,4-diethoxybenzoyloxy)succinimido)-4(R)-(1-(quinolin-4-yl)ethylen-2-yl)azetidin-2-on-1-yl]acetate N-[phenyl]-2(S)-[N-(2-fluoro-3-methyl)benzylbutanamido-4-yl]-2-[3(S)-(3,4-di(4-fluorobenzoyloxy)succinimido)-4(R)-(1-(quinolin-5-yl)ethylen-2-yl)azetidin-2-on-1-yl]acetamide N-[3-trifluoromethylbenzyl]-2(S)-[N-(4-methoxy)benzylpentanamido-5-yl]-2-[3(S)-(3,4-di(2-chlorobenzoyloxy)succinimido)-4(R)-(1-(quinolin-6-yl)ethylen-2-yl)azetidin-2-one-1-yl]acetamide N-[cyclopropyl]-2(S)-[N-(4-isopropyl)benzylpentanamido-5-yl]-2-[3(S)-(3,4-di(3,4-dibenzoyloxy)succinimido)-4(R)-(1-(quinolin-7-yl)ethylen-2-yl)azetidin-2-on-1-yl]acetamide N-[cyclobutylethyl]-2(R,S)-isopropyl-2-[3(S)-(3,4-di(3-methoxy-4-chlorobenzoyloxy)succinimido)-4(R)-(1-(quinolin-8-yl)ethylen-2-yl)azetidin-2-on-1-yl]acetamide N-[cyclopentyl]-2(R,S)-isobutyl-2-[3(S)-(3,4-di(4-cyanobenzoyloxy)succinimido)-4(R)-(1-(isoquinolin-1-yl)-ethylen-2-yl)azetidin-2-on-1-yl]acetamide N-[phenethyl]-2(R,S)-[1-hydroxy-2,2-dimethylpropyl]-2-[3(S)-(3,4-di(3-nitrobenzoyloxy)succinimido)-4(R)-(1-(isoquinolin-3-yl)ethylen-2-yl)azetidin-2-on-1-yl]acetamide N-[phenpropyl]-2(R,S)-[(1,1-ethyleneketal)propionyl]-2-[3(S)-(3,4-di(2-aminobenzoyloxy)succinimido)-4(R)-(1-(isoquinolin-4-yl)ethylen-2-yl)azetidin-2-on-1-yl]acetamide N-[3-trifluoromethylbenzyl]-2(R,S)-[(1,1-ethyleneketal)-acetyl]-2-[3(S)-(3,4-di(4-methoxycarbonylbenzoyloxy)-succinimido)-4(R)-(1-(isoquinolin-5-yl)ethylen-2-yl)azetidin-2-on-1-yl]acetamide N-[4-chlorobenzyl]-2(R,S)-[2,2-dimethylpropionyl]-2-[3(S)-(3,4-di(benzyloxy)succinimido)-4(R)-(1-(isoquinolin-6-yl)ethylen-2-yl)azetidin-2-on-1-yl]acetamide N-[2-bromobenzyl]-2(R,S)-[N-benzylcarboxamido]-2-[3(S)-(3,4-di(diphenylmethoxy)succinimido)-4(R)-(1-(isoquinolin-7-yl)ethylen-2-yl)azetidin-2-on-1-yl]acetamide N-[3-fluorobenzyl]-2(R,S)-[N-(3-trifluoromethyl)benzylcarboxamido]-2-[3(S)-(3,4-di(triphenylmethoxy)succinimido)-4(R)-(1-(isoquinolin-8-yl)ethylen-2-yl)azetidin-2-on- 1-yl]acetamide N-[2-methylbenzyl]-2(R,S)-[N-phenylcarboxamido]-1-2-[3(S)-(3-acetyloxysuccinimido)-4(R)-(1-(naphth-1-yl)ethylen-2-yl)azetidin-2-on-1-yl]acetamide N-[3-chloro-4-isopropylbenzyl]-2(R,S)-[N-(2-chlorophenyl)carboxamido]-2-[3(S)-(3-isopropionyloxysuccinimido)-4(R)-(1-(naphth-2-yl)ethylen-2-yl)azetidin-2-on-1-yl]acetamide N-[2,4-dimethoxybenzyl]-2(R,S)-[N-(4-methylphenyl)carboxamido]-2-[3(S)-(3-tert-butanoyloxysuccinimido)-4(R)-(1-(2-fluorophenyl)ethylen-2-yl)azetidin-2-on-1-yl]acetamide N-[3-isopropoxybenzyl]-2(R,S)-[N-(3-isopropylphenyl)-carboxamido]-2-[3(S)-(3-pentanoyloxysuccinimido)-4(R)-(1-(3-chlorophenyl)ethylen-2-yl)azetidin-2-on-1-yl]acetamide N-[4-sulfonamidobenzyl]-2(R,S)-[N-(4-trifluoromethylphenyl)carboxamido]-2-[3(S)-(3-(2-methylbenzoyloxy)succinimido)-4(R)-(1-(4-bromophenyl)ethylen-2-yl)azetidin-2-on-1-yl]acetamide N-[quinuclidin-2-yl]-2(R,S)-[N-(4-methylphenyl)carboxamido]-2-[3(S)-(3-ethylbenzoyloxy)-4(R)-(1-(3-iodophenyl)-ethylen-2-yl)azetidin-2-on-1-yl]acetamide 1-{2(R,S)-[N-(3-trifluoromethylbenzyl)acetamido-2-yl]-2-[3(S)-(3-(4-isobutylbenzoyloxy)succinimido)-4(R)-(1-(2-methylphenyl)ethylen-2-yl)azetidin-2-on-1-yl]}-1,2,3,4-tetrahydronaphthalene 1-{2(R,S)-[N-(benzyl)acetamido-2-yl]-2-[3(S)-(3-(3,5-dimethylbenzoyloxy)succinimido)-4(R)-(1-(3-isopropylphenyl)-ethylen-2-yl)azetidin-2-on-1-yl]}-4-hydroxypiperidine 1-{2(R,S)-[N-(4-chlorophenyl)acetamido-2-yl]-2-[3(S)-(3-(2-methoxybenzoyloxy)succinimido)-4(R)-(1-(4-pentylphenyl)ethylen-2-yl)azetidin-2-on-1-yl]}4-(piperidin-1-yl)piperidine 1-{2(R,S)-[N-(2-cyanophenyl)acetamido-2-yl]-2-[3(R)-(3-tert-butoxybenzoyloxysuccinimido)-4(S)-(1-(2-propoxyphenyl)ethylen-2-yl)azetidin-2-on-1-yl]}-4-benzylpiperidine 1-{2(R,S)-[N-(phenylethyl)acetamido-2-yl]-2-[3(S)-(3-(3,4-diethoxybenzoyloxy)succinimido)-4(R)-(1-(3-methoxyphenyl)ethylen-2-yl)azetidin-2-on-1-yl]}-4-((piperidin-1-yl)methyl)piperidine 1-{2(R,S)-[N-(benzyl)propionamido-3-yl]-2-[3(S)-(3-(4-fluorobenzoyloxy)succinimido)-4(R)-(1-(4-isobutoxyphenyl)ethylen-2-yl)azetidin-2-on-1-yl]}-4-(2-(piperidin-1-yl)ethyl)piperidine 1-{2(R,S)-[N-(3-trifluoromethylbenzyl)propionamido-3-yl]-2-[3(R)-(3-(2-chlorobenzoyloxy)succinimido)-4(S)-(1-(2-ethylthiophenyl)ethylen-2-yl)azetidin-2-on-1-yl]}-4-(3-(piperidin-1-yl)propyl)piperidine 1-{2(R,S)-[N-(3-fluorophenyl)propionamido-3-yl]-2-[3(S)-(3-(3,4-dibromobenzoyloxy)succinimido)-4(R)-(1-(3-hexylthiophenyl)ethylen-2-yl)azetidin-2-on-1-yl]}-4-(4-(piperidin-1-yl)butyl)piperidine 1-{2(R,S)-[N-(3-aminophenyl)propionamido-3-yl]-2-[3(S)-(3-(3-methoxy-4-iodobenzoyloxy)succinimido)-4(R)-(1-(4-methylthiophenyl)ethylen-2-yl)azetidin-2-on-1-yl]}-2,4-dimethylpiperidine 1-{2(R,S)-[N-(benzyl)propionamido-3-yl]-2-[3(S)-(3-(4-cyanobenzoyloxy)succinimido)-4(R)-(1-(2-nitrophenyl)ethylen-2-yl)azetidin-2-on-1-yl])-3,5-dimethylpiperidine 1-{2(R,S)-[N-(3-methylbenzyl)propionamido-3-yl]-2-[3(S)-(3-(3-nitrobenzoyloxy)succinimido)-4(R)-(1-(3-nitrophenyl)ethylen-2-yl)azetidin-2-on-1-yl]}-4-methylpiperidine 1-(2(R,S)-[N-(4-isopropoxybenzyl)propionamido-3-yl]-2-[3(S)-(3-(2-aminobenzoyloxy)succinimido)-4(R)-(1-(4-nitrophenyl)ethylen-2-yl)azetidin-2-on-1-yl]}-4-isopropylpiperazine 1-{2(R,S)-[N-(3-iodobenzyl)propionamido-3-yl]-2-[3(S)-(3-(4-methoxycarbonylbenzoyloxy)succinimido)-4(R)-(1-(2-carboxyphenyl)ethylen-2-yl)azetidin-2-on-1-yl]}-4-phenethylpiperazine 1-{2(R,S)-[N-(phenethyl)propionamido-3-yl]-2-[3(S)-(3-(benzyl)oxysuccinimido)-4(R)-(1-(3-carboxamidophenyl)-ethylen-2-yl)azetidin-2-on-1-yl]}-4-cyclohexylpiperazine 1-{2(R,S)-[N-(benzyl)butanamido-4-yl]-2-[3(S)-(3-(diphenylmethoxy)succinimido)-4(R)-(1-(2,3-difluorophenyl)-ethylen-2-yl)azetidin-2-on-1-yl]}-4-cyclopropylpiperazine 1-{2(R,S)-[N-(3-trifluoromethylbenzyl)butanamido-4-yl]-2-[3(S)-(3-(triphenylmethoxy)succinimido)-4(R)-(1-(3,5-dichlorophenyl)ethylen-2-yl)azetidin-2-on-1-yl]}-4-benzylpiperazine.

The 2-(azetidinon-1-yl)acetic acid esters and amides of Formula I are prepared by methods well known in the art. The 2-(azetidinon-1-yl)acetic acid esters are obtainable by the 2+2 cycloaddition of an appropriately substituted acetic acid derivative (i), and an imine ester (ii) as described in Synthetic Scheme I. Z is halo, acyloxy or benzoyloxy, and $R^1$, $R^2$, $R^3$, $R^4$, and $R^9$ are as previously described. While the chemistry described in Synthetic Scheme I is applicable to imines (ii) bearing ester, thioester or amide moieties, only the esters are illustrated.

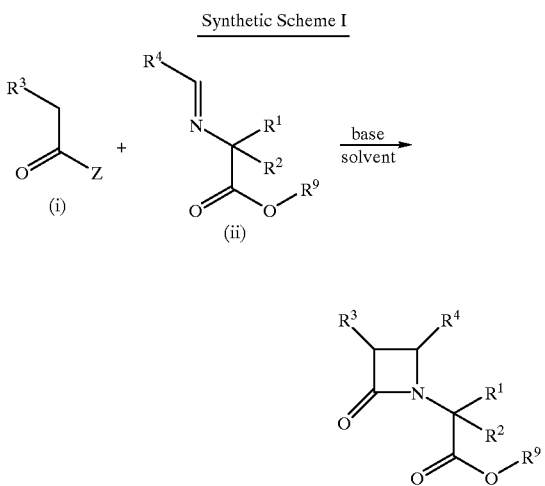

The preparation of the appropriate imines (ii) and most of the required acetyl halides or anhydrides (i), as well as the cycloaddition procedure, are generally described in U.S. Pat. Nos. 4,665,171 and 4,751,299, hereby incorporated by reference.

Those compounds of the invention requiring $R^3$ to be 4-substituted oxazolidin-2-on-3-yl are prepared from the corresponding (4-substituted oxazolidin-2-on-3-yl)acetyl halide or anhydride. The acid halide or anhydride is available from an appropriately substituted glycine. The glycine is first converted to the carbamate and then reduced to provide the corresponding alcohol. The alcohol is then cyclized to the 4-substituted oxazolidin-2-one, which is subsequently N-alkylated with a haloacetic acid ester, the ester deesterified, and the acid converted to the acetyl halide or anhydride (i).

Those compounds of the invention requiring $R^3$ to be 2,5-disubstituted oxazolidin-4-on-3-yl or 1,2,5-trisubstituted imidazolidin-4-on-3-yl are prepared from the corresponding (2,5-disubstituted oxazolidin-4-on-3-yl)- or (1,2,5-trisubstituted imidazolidin-4-on-3-yl)acetyl chlorides or anhydrides respectively. The chemistry to prepare these reagents is described in U.S. Pat. No. 4,772,694, hereby incorporated by reference. Briefly, the required oxazolidinone or imidazolidinone is obtained with an α-hydroxyacid or an α-aminoacid, respectively. The imidazolones are prepared by converting the α-aminoacid, $(R^{12})$—CH(NH$_2$)CO$_2$H, to an amino-protected amide and then condensing the amide with an aldehyde, $(R^{11})$—CHO, in the presence of an acid to form the 3-protected imidazolidin-4-one. The 1-position may be functionalized with an appropriate reagent to introduce $R^{13}$ and the 3-position deprotected. The imidazolidin-4-one ring is then alkylated with a haloacetic acid ester, the ester deesterified, and the resulting acetic acid converted to the desired acid halide or anhydride (i). The required oxazolidinones are prepared in an analogous manner from the corresponding α-hydroxyacid, $(R^{12})$—CH(OH)CO$_2$H.

Those compounds of the invention requiring $R^3$ to be succinimido are prepared from the corresponding 2-(succinimido)acetyl halide or anhydride. The chemistry to prepare these reagents is described in U.S. Pat. No. 4,734,498, hereby incorporated by reference. Briefly, these reagents are obtained from tartaric acid or, when one of $R^{14}$ and $R^{15}$ is hydrogen, from malic acid. Tartaric acid is acylated or O-alkylated, the corresponding diacyl or di-O-alkyl tartaric acid treated with an acid anhydride to form the succinic anhydride, and reaction of this succinic anhydride with an ester of glycine to form first the noncyclic half amide ester which is then cyclized to the 3,4-disubstituted succinimidoacetic acid ester. The ester group is deesterified and the resulting acid converted to the corresponding acid halide or anhydride (i). The mono-substituted succinimidoacetyl halide or anhydride is obtained with malic acid via succinic anhydride formation followed by succinimide formation as described above.

As discussed supra, the compounds prepared as described in Synthetic Scheme I may be pure diastereomers, mixtures of diastereomers, or racemates. The actual stereochemical composition of the compound will be dictated by the specific reaction conditions, combination of substituents, and stereochemistry of the reactants employed in Synthetic Scheme I. The skilled artisan will appreciate that diasteromeric mixtures may be separated by chromatography or fractional crystallization to provide single diastereomers if desired.

The bases to be used in Synthetic Scheme I include, among others, aliphatic tertiary amines, such as trimethylamine and triethylamine, cyclic tertiary amines, such as N-methylpiperidine and N-methylmorpholine, aromatic amines, such as pyridine and lutidine, and other organic bases such as 1,8-diazabicyclo[5,4,0]undec-7-ene (DBU).

The solvents useful for reactions described in Synthetic Scheme I include, among others, dioxane, tetrahydrofuran, diethyl ether, ethyl acetate, dichloromethane, chloroform, carbon tetrachloride, benzene, toluene, acetonitrile, di-methyl sulfoxide and N,N-dimethylformamide.

Compounds of Formula I where $R^1$ and $R^2$ are hydrogen, while useful vasopressin $V_{1a}$ agents in their own right, are also useful synthetic intermediates for the preparation of compounds where $R^1$ is $C_1$–$C_5$ acyl, $C_3$–$C_6$ cycloalkylcarbonyl-($C_1$–$C_4$ alkylene)C(O)NR$^5$X, benzoyl, phenoxyacetyl, phenylacetyl where the phenyl is optionally substituted with halo, $C_1$–$C_4$ alkyl, $C_1$–$C_4$ alkoxy, or trifluoromethyl, or α-hydroxy-α-benzoylbenzyl, as well as compounds where $R^1$ is hydroxy substituted $C_1$–$C_5$ alkyl and $R^2$ is hydrogen, or compounds where both $R^1$ and $R^2$ are hydroxy substituted $C_1$–$C_5$ alkyl. The preparation of these compounds is described in Synthetic Scheme II.

Synthetic Scheme II

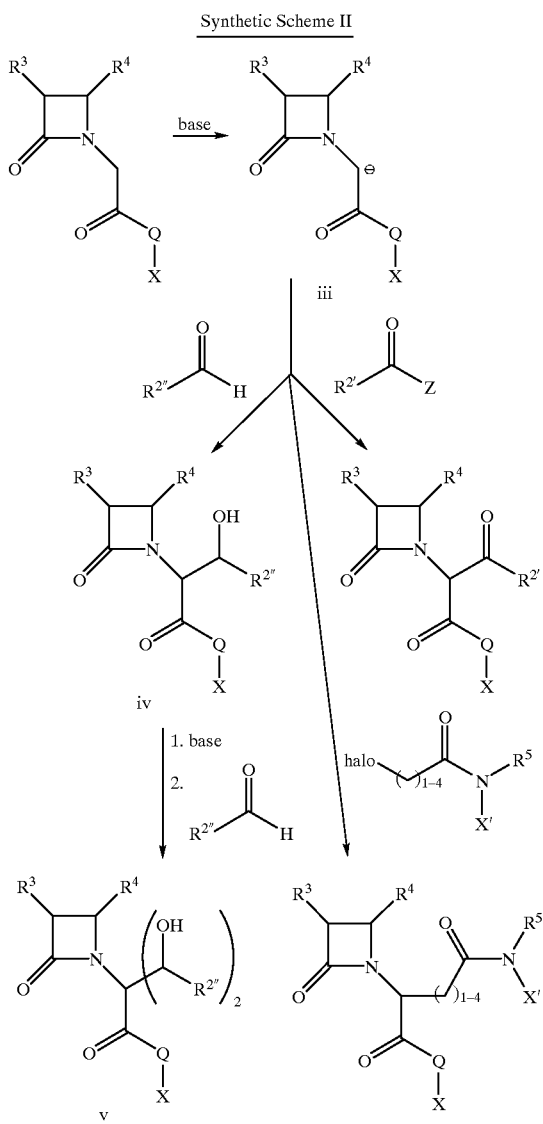

$R^{2'}$ represents hydrogen; $C_1$–$C_4$ alkyl; $C_3$–$C_6$ cycloalkyl; phenyl; phenoxymethyl; or benzyl where the phenyl group is optionally substituted with halo, $C_1$–$C_4$ alkyl, $C_1$–$C_4$ alkoxy or trifluoromethyl; $R^{2''}$ represents $C_1$–$C_5$ alkyl; Z represents halo; $C_1$–$C_4$ alkoxy; or $R^{2'}C(O)$—; and $R^3$, $R^4$, $R^5$, Q, X, and X' are as previously defined. The reaction described in Synthetic Scheme II creates a chiral center at the carbon bearing $R^1$ and $R^2$. The skilled artisan will appreciate that the racemic mixture may be separated into separate stereoisomers by fractional crystallization or chromatography if desired.

A solution of the 2-(3,4-disubstituted azetidin-2-on-1-yl) acetic acid derivative in an appropriate solvent, such as tetrahydrofuran, dioxane or diethyl ether, is treated with a non-nucleophilic base to generate the anion (iii). Suitable bases for this transformation include lithium diisopropylamide, lithium 2,2,6,6-tetramethylpiperidinamide, or lithium bis(trimethylsilyl) amide. The anion is then quenched with an appropriate electrophile to provide the desired compounds. Electrophiles of formula $R^{2'}C(O)Z$, representing esters, acid halides and anhydrides, provide the corresponding carbonyl containing derivatives. Electrophiles of formula $R^{2''}C(O)H$ provide the corresponding alcohols. Electrophiles of formula halo-$(CH_2)_{1-4}$—$C(O)NR^5X'$ provide the corresponding ($C_1$–$C_4$ alkylene)carboxamides. The skilled artisan will appreciate that reaction of the anion (iii) with benzil provides compounds of the invention where $R^2$ is α-hydroxy-α-benzoylbenzyl. The skilled artisan furthermore will appreciate that treatment of alcohol (iv) with a second equivalent of base and additional electrophile of formula $R^{2''}C(O)H$ provides the disubstituted compounds of the invention (v).

Compounds of Formula I which are 2-(3,4-disubstituted azetidin-2-on-1-yl)acetate esters, while useful vasopressin $V_{1a}$ agents in their own right, may also be converted to the corresponding carboxylic acid to provide intermediates useful for the preparation of other compounds of the invention as illustrated in Synthetic Scheme III. $R^1$, $R^2$, $R^3$, $R^4$, $R^5$, $R^9$, and X' are as previously defined.

Synthetic Scheme III

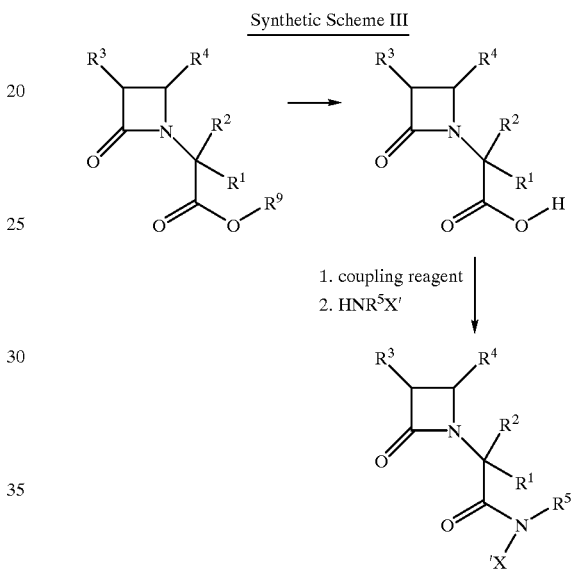

The requisite carboxylic acid may be prepared from the corresponding ester by saponification under standard conditions by treatment with hydroxide followed by protonation of the resultant carboxylate anion. Where $R^9$ is tert-butyl, the ester may be dealkylated by treatment with trifluoroacetic acid. Where $R^9$ is benzyl, the ester may be dealkylated either by subjection to mild hydrogenolysis conditions, or by reaction with elemental sodium or lithium in liquid ammonia. Finally, where $R^9$ is 2-(trimethylsilyl)ethyl, the ester is deprotected by treatment with a source of fluoride ion, such as tetrabutylammonium fluoride. The choice of conditions is dependent upon the nature of the $R^9$ moiety and compatability of other functionality in the molecule to the reaction conditions.

The carboxylic acid is converted to the corresponding amide under standard conditions well recognized in the art. The acid may be first converted to the corresponding acid halide, preferably the chloride or fluoride, followed by treatment with an appropriate primary or secondary amine to provide the corresponding amide. Alternatively, the acid may be converted under standard conditions to a mixed anhydride. This is typically accomplished by first treating the carboxylic acid with an amine, such as triethylamine, to provide the corresponding carboxylate anion. This carboxylate is then reacted with a suitable haloformate, for example benzyl chloroformate, ethyl chloroformate or isobutylchloroformate, to provide the corresponding mixed anhydride. This anhydride may then be treated with an appropriate primary or secondary amine to provide the desired amide. Finally, the carboxylic acid may be treated with a typical peptide coupling reagent such as N,N'-carbonyldiimidazole (CDI), N,N'-dicyclohexylcarbodiimide (DCC) and 1-(3-dimethylaminopropyl)-3-ethylcarbodiimide hydrochloride (EDC), followed by the appropriate amine of formula $HNR^5X$. A polymer supported form of EDC has been described (*Tetrahedron Letters*, 34(48), 7685 (1993)) and is very useful for the preparation of the compounds of the present invention. The skilled artisan will appreciate that substituting an appropriate amine with an appropriate alcohol will provide the esters of the invention. The skilled artisan will furthermore appreciate that, for those compounds where the $R^1$ moiety is —$C(O)NR^5X'$ or -$(C_1$–$C_4$ alkylene)$C(O)NR^5X'$, the variables $R^5$ and $X'$ of the amine, $HNR^5X'$, used for the preparation of the amide described supra, may be the same or different as those selected for the moiety $R^1$.

Compounds of Formula I where $R^4$ is 2-arylethen-1-yl may be converted into the corresponding arylethyl derivatives by subjecting the substrate to standard hydrogenation conditions as described in Synthetic Scheme IV. $R^1$, $R^2$, $R^3$, Q, and X are as previously defined.

Synthetic Scheme IV

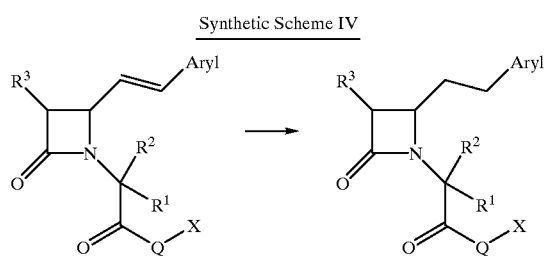

The hydrogenation of the double bond proceeds readily over a precious metal catalyst, such as palladium on carbon. The hydrogenation solvent may consist of a lower alkanol, such as methanol or ethanol, tetrahydrofuran, or a mixed solvent system of tetrahydrofuran and ethyl acetate. The hydrogenation may be performed at an initial hydrogen pressure of 20–80 p.s.i., preferably from 50–60 p.s.i., at 0–60° C., preferably at ambient temperature to 40° C., for 1 hour to 3 days. Additional charges of hydrogen may be required to drive the reaction to completion depending on the specific substrate.

Compounds of Formula I where $R^3$ is phthalimido are conveniently treated with hydrazine or a hydrazine derivative, for example methylhydrazine, to prepare the corresponding 2-(3-amino-4-substituted azetidin-2-on-1-yl) acetic acid derivative. This compound may then be treated with an appropriate isocyanate to prepare the corresponding ureas as illustrated in Synthetic Scheme V. $R^1$, $R^2$, $R^4$, $R^6$, Q, and X are as previously defined.

Synthetic Scheme V

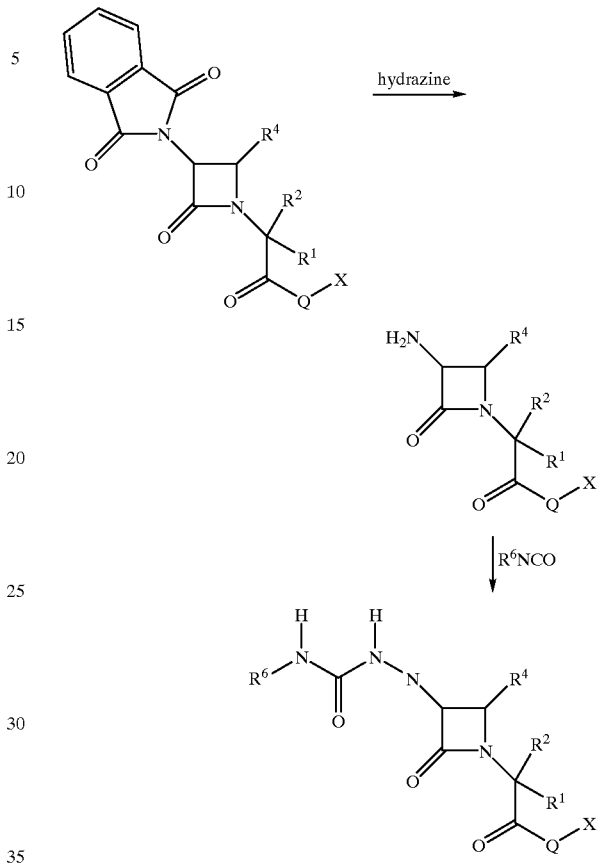

The ureas are prepared by treating a solution of the appropriate amine in a suitable solvent, such as chloroform or dichloromethane, with an appropriate isocyanate. If necessary, an excess of the isocyanate is employed to ensure complete reaction of the starting amine. The reactions are performed at about ambient to about 45° C., for from about three hours to about three days. Typically, the product may be isolated by washing the reaction with water and concentrating the remaining organics under reduced pressure. When an excess of isocyanate has been used, however, a polymer bound primary or secondary amine, such as an aminomethylated polystyrene, may be conveniently added to react with the excess reagent. Isolation of products from reactions where a polymer bound reagent has been used is greatly simplified, requiring only filtration of the reaction mixture and then concentration of the filtrate under reduced pressure.

The skilled artisan will appreciate that, in many cases, the order of the steps described above is not critical. For example, an appropriate α-amino acid may be suitably substituted by chemistry generally described in Synthetic Schemes II and III prior to subjecting it to the 2+2 cycloaddition described in Synthetic Scheme I to provide a compound of the invention.

The following preparations and examples further illustrate the synthesis of the compounds of this invention and are not intended to limit the scope of the invention in any way. The compounds described below were identified by various standard analytical techniques as stated in the individual preparations and examples.

PREPARATION I (4(S)-phenyloxazolidin-2-on-3-yl)acetyl chloride

To a solution of 1.31 gm (5.93 mMol) (4(S)-phenyloxazolidin-2-on-3-yl)acetic acid (Evans, U.S. Pat. No. 4,665,171) in 200 mL dichloromethane was added 0.67 mL (7.71 mMol) oxalyl chloride. To this solution was then added 0.5 mL anhydrous dimethylformamide which resulted in vigorous gas evolution. After 45 minutes all gas evolution had ceased and the reaction mixture was concentrated under reduced pressure. The title compound, recovered as an off-white solid, was dried at 0.5 mm Hg for 10 minutes before use in subsequent reactions.

PREPARATION II 2-(trimethylsilyl)ethyl 2-amino-3,3-(ethyleneketal) acetoacetate 2-(trimethylsilyl)ethyl acetoacetate 10.66 gm (91.8 mMol) methyl acetoacetate and excess 2-(trimethylsilyl)ethanol were heated together at reflux. Methanol was distilled (68° C.) from the reaction mixture and heating was continued until the head temperature dropped below 65° C. The reaction mixture was then concentrated under reduced pressure at 40° C. to provide 18.24 gm (98%) of the desired compound as a pale yellow oil.

2-(trimethylsilyl)ethyl 2-(oximino)acetoacetate

To a solution of 18.24 gm (90.3 mMol) 2-(trimethylsilyl) ethyl acetoacetate in 10 mL acetic acid at −4° C. was added a solution of 6.85 gm (99.3 mMol) sodium nitrite in 30 mL of water dropwise over 15 minutes. The reaction mixture was allowed to warm to room temperature while stirring. After 2 hours the reaction mixture was diluted with 100 mL ethyl acetate and washed twice with 50 mL portions of saturated aqueous sodium chloride. The organic phase was dried over sodium sulfate and concentrated under reduced pressure. The residual was dissolved in toluene and concentrated under reduced pressure twice to azeotropically remove any remaining acetic acid. The residual oil was finally subjected to flash silica gel chromatography, eluting with hexane containing 30% ethyl acetate. Fractions shown to contain product were combined and concentrated under reduced pressure to provide 12.04 gm (58%) of the desired compound as a colorless oil.

2-(trimethylsilyl)ethyl 2-oximino-3.3-ethyleneketal acetoacetate

To a solution of 12.04 gm (52.1 mMol) 2-(trimethylsilyl) ethyl 2-(oximino)acetoacetate in 100 mL toluene were added 0.10 gm p-toluenesulfonic acid and 6.8 mL (121.8 mMol) ethylene glycol. The reaction mixture was heated at reflux with constant water removal (Dean-Stark Trap). After 4 hours the reaction mixture was cooled to room temperature, washed well with water, dried over magnesium sulfate and concentrated under reduced pressure to provide 14.04 gm (98%) of the desired compound as a yellow oil which solidified upon standing.

Reduction

Granular (40 mesh) aluminum (1.5 gm, 55.5 mMol) was washed sequentially with 0.1 N sodium hydroxide, water, 0.5% aqueous mercury(I) chloride, ethanol, and diethyl ether. The wash sequence was then repeated. A slurry of the resulting amalgam in 100 mL diethyl ether was then cooled to 0° C. and then 3 mL water were added. To this stirring mixture was added a solution of 3.0 gm (10.9 mMol) 2-(trimethylsilyl)-ethyl 2-oximino-3,3-ethyleneketal acetoacetate in 30 mL diethyl ether dropwise. The exothermic reaction was controlled with an ice bath. After the addition was complete, the reaction mixture was stirred for 2 hours at room temperature. The reaction mixture was then filtered through CELITE™ and the filtrate concentrated under reduced pressure to give 2.5 gm (88%) of the title compound as a colorless oil.

NMR(CDCl$_3$): δ4.2 (t, 2H), 3.95 (m, 4H), 3.5 (s, 1H), 1.7 (s, 2H), 1.35 (s, 3H), 1.01 (t, 2H), 0.04 (s, 9H).

PREPARATION III 2-(trimethylsilyl)ethyl 2-amino-3,3-(ethyleneketal) propionylacetate Following the procedure described in Preparation II, 11.74 gm (90.2 mMol) methyl propionylacetate were used to prepare the title compound which was recovered as a colorless oil.

PREPARATION IV 4-methyl-(L)-leucine tert-butyl ester

To a pressure bottle were added 1.5 gm (10.3 mMol) 4-methyl-(L)-leucine, 25 mL dioxane, 1.5 mL concentrated sulfuric acid and 25 mL isobutylene. The pressure bottle was stoppered and the reactants were shaken together for 18 hours. The reaction mixture was then treated with 60 mL cold 1N sodium hydroxide and 100 mL ethyl acetate. To this mixture was added sufficient 1N sodium hydroxide until the pH of the mixture was 8.5. The layers were separated and the aqueous phase was extracted well with ethyl acetate. The combined ethyl acetate phases were dried over sodium sulfate and concentrated under reduced pressure to provide an oil which gradually crystallized to provide 1.05 gm (50.5%) of the title compound.

General Procedure for the Preparation of Imines (METHOD A)

To a solution of one equivalent of an α-amino acid ester or amide in dichloromethane are added one equivalent of an appropriate aldehyde. To the resulting solution is added a dessicating agent, typically magnesium sulfate or silica gel, in the amount of 2 grams of dessicating agent per gram of starting α-amino acid ester or amide. The reaction is stirred at room temperature until all of the reactants are consumed as measured by thin layer chromatography. The reactions are typically complete within an hour. The reaction mixture is then filtered, the filter cake washed with dichloromethane, and the filtrate concentrated under reduced pressure to provide the desired imine which is used as is in the subsequent step.

General Procedure for the 2+2 Cycloaddition (METHOD B)

A dichloromethane solution of the imine (10 mL dichloromethane/1 gram imine) is cooled to 0° C. To this cooled solution is added 1.5 equivalents of an appropriate amine, typically triethylamine, followed by the dropwise addition of a dichloromethane solution of 1.1 equivalents of an appropriate acetyl chloride, such as that described in Procedure I (10 mL dichloromethane/1 gm appropriate acetyl chloride). The reaction mixture is allowed to warm to room temperature over one hour and is then quenched by the addition of saturated aqueous ammonium chloride. The resulting mixture is partitioned between water and dichloromethane. The phases are separated and the organic phase is washed successively with IN hydrochloric acid, saturated aqueous sodium bicarbonate and saturated aqueous sodium chloride. The remaining organics are dried over magnesium sulfate and concentrated under reduced pressure. The residue may be used directly for further reactions, or purified chromatographically or by crystallization from an appropriate solvent system if desired.

EXAMPLE 1

Methyl 2-[3(S)-(4(S)-phenyloxazolidin-2-on-3-yl)-4 (R)-(2-styryl)azetidin-2-on-1-yl]acetate Beginning with 26.7 gm (0.3 mole) glycine methyl ester and one equivalent of cinnamaldehyde, the corresponding imine was prepared by the procedure described above (METHOD A). This imine and 1.1 equivalents of 2-(4(S)-phenyloxazolidin-2-on-3-yl)acetyl chloride were subjected to the 2+2 cycloaddition conditions described above (METHOD B) to provide 81 gm (66%) of the title compound as an orange foam. This foam was purified by crystallization from ethyl acetate/ethanol to provide colorless crystals.

m.p.=169–170° C.; MS (FD): m/e=407 (M+1).

The compounds of Examples 2–13 were prepared by the methodology described in Example 1.

EXAMPLE 2 tert-Butyl 2-[3(S)-(4(S)-phenyloxazolidin-2-on-3-yl)-4(R)-(2-styryl)azetidin-2-on-1-yl]acetate Beginning with 4.53 gm (34.5 mMol) glycine tert-butyl ester, 5.5 gm (30%) of the title compound were recovered as colorless crystals from n-chlorobutane.

m.p.=194–195° C.; MS(FD): m/e=448 ($M^+$).

EXAMPLE 3

Benzyl 2-[3(S)-(4(S)-phenyloxazolidin-2-on-3-yl)-4 (R)-(2-styryl)azetidin-2-on-1-yl]acetate Beginning with 20 gm (121 mMol) glycine benzyl ester, 13.8 gm (20%) of the title compound were recovered as colorless crystals from ethyl acetate.

m.p.=143–145° C.; MS(FD): m/e=482 ($M^+$).

EXAMPLE 4

4-Nitrobenzyl 2-[3 (S)-(4(S)-phenyloxazolidin-2-on-3-yl)-4(R)-(2-styryl)azetidin-2-on-1-yl]acetate Beginning with 5 gm (23.8 mMol) glycine 4-nitrobenzyl ester, 2.21 gm (18%) of the title compound were recovered.

EXAMPLE 5

Methyl 2-(R,S)-isopropyl-2-[3 (S)-(4(S)-phenyloxazolidin-2-on-3-yl)-4(R)-(2-styryl)azetidin-2-on-1-yl]acetate Beginning with 2.59 gm (19.8 mMol) (D,L)-valine methyl ester, 4.25 gm (48%) of the title compound were recovered as colorless crystals from 95:5 ethyl acetate:acetonitrile.

m.p.=182–185° C.; MS(FD): m/e 448 ($M^+$).

EXAMPLE 6

Methyl 2-(S)-isobutyl-2-[3 (S)-(4(S)-phenyloxazolidin-2-on-3-yl)-4(R)-(2-styryl)azetidin-2-on-1-yl]acetate Beginning with 8.73 gm (60.1 mMol) (L)-leucine methyl ester, 12.0 gm (64%) of the title compound were recovered as a colorless powder from 3:1 n-chlorobutane:acetonitrile.

m.p.=170–172° C.; MS(FD): m/e=463 ($M^+$).

EXAMPLE 7

Benzyl 2-(S)-isobutyl-2-[3(S)-(4(S)-phenyloxazolidin-2-on-3-yl)-4(R)-(2-styryl)azetidin-2-on-1-yl]acetate Beginning with 1.68 gm (7.6 mMol) (L)-leucine benzyl ester, 2.0 gm (57%) of the title compound were recovered as colorless crystals from n-chlorobutane.

m.p.=178° C.; MS(FD): m/e=538 ($M^+$).

EXAMPLE 8

Benzyl 2-(R)-isobutyl-2-[3(S)-(4(S)-phenyloxazolidin-2-on-3-yl)-4(R)-(2-styryl)azetidin-2-on-1-yl]acetate Beginning with 2.29 gm (9.05 mMol) (D)-leucine benzyl ester, 0.11 gm (2.2%) of the title compound were recovered as colorless crystals from ethyl acetate.

m.p.=134° C.; MS(FD): m/e=538 ($M^+$).

EXAMPLE 9 tert-Butyl 2-(S)-(2,2-dimethylpropyl)-2-[3(S)-(4(S)-phenyloxazolidin-2-on-3-yl)-4(R)-(2-styryl)azetidin-2-on-1-yl]acetate Beginning with 1.05 gm (5.2 mMol) 4-methyl-(L)-leucine tert-butyl ester, the title compound was recovered as colorless crystals from n-chlorobutane:hexane.

m.p.=185–186° C.; MS(FD): m/e=518 ($M^+$).

EXAMPLE 10

Benzyl 2-phenyl-2-[3(S)-(4(S)-phenyloxazolidin-2-on-3-yl)-4(R)-(2-styryl)azetidin-2-on-1-yl]acetate Beginning with 1.0 gm (4.14 mMol) (D,L)-phenylglycine benzyl ester, the title compound was recovered as a tan oil. A portion of this material was subjected to silica gel chromatograpy, eluting with 2:1 hexane: ethyl acetate to provide 0.20 gm of the title compound as a colorless solid.

MS(FD): m/e=558 ($M^+$); EA: Calculated for: $C_{35}H_{30}N_2O_5$. Theory: C, 75.25; H, 5.41; N, 5.02. Found: C, 75.91; H, 5.91; N, 4.84.

EXAMPLE 11

Methyl 2-(R)-benzyl-2-[3(S)-(4(S)-phenyloxazolidin-2-on-3-yl)-4(R)-(2-styryl)azetidin-2-on-1-yl]acetate Beginning with 1.71 gm (9.55 mMol) (D)-phenylalanine methyl ester, 1.01 gm (25%) of the title compound were recovered as colorless crystals from 95:5 n-chlorobutane: acetonitrile.

m.p.=204–205° C.; MS(FD): m/e=497 (M+1).

EXAMPLE 12

2-(Trimethylsilyl)ethyl 2-[(1,1-ethyleneketal)acetyl]-2-[3(S)-(4(S)-phenyloxazolidin-2-on-3-yl)-4(R)-(2-styryl)azetidin-2-on-1-yl]acetate Beginning with 2.5 gm (9.58 mMol) 2-(trimethylsilyl)-ethyl 2-amino-3,3-(ethyleneketal)acetoacetate, 3.0 gm (54%) of the title compound were recovered as a colorless solid after silica gel chromatography, eluting with 2:3 ethyl acetate:hexane.

MS(FD): m/e=578 (M$^+$); EA: Calculated for: $C_{31}H_{38}N_2O_7Si$. Theory: C, 64.34; H, 6.62; N, 4.84. Found: C, 64.48; H, 6.47; N, 4.91.

EXAMPLE 13

2-(Trimethylsilyl)ethyl 2-[(1,1-ethyleneketal) propionyl]-2-[3(S)-(4(S)-phenyloxazolidin-2-on-3-yl)-4(R)-(2-styryl)azetidin-2-on-1-yl]acetate Beginning with 2.07 gm (7.53 mMol) 2-(trimethylsilyl)-ethyl 2-amino-3,3-(ethyleneketal)propionylacetate, 3.45 gm (77%) of the title compound were recovered as a colorless solid after silica gel chromatography, eluting with 2:3 ethyl acetate:hexane.

MS(FD): m/e=593 (M+1); EA: Calculated for: $C_{32}H_{40}N_2O_7Si$. Theory: C, 64.84; H, 6.80; N, 4.73. Found: C, 64.84; H, 6.87; N, 4.72.

EXAMPLE 14

Benzyl 2-(S)-isobutyl-2-[3(R)-(4(R)-phenyloxazolidin-2-on-3-yl)-4(S)-(2-styryl)azetidin-2-on-1-yl]acetate Beginning with 3.80 gm (17.2 mMol) (L)-leucine benzyl ester and one equivalent of cinnamaldehyde, the corresponding imine was prepared by Method A. This imine and 1.1 equivalents of 2-(4(R)-phenyloxazolidin-2-on-3-yl)acetyl chloride were subjected to the 2+2 cycloaddition conditions (Method B) to provide 6.05 gm (66%) of the title compound as colorless crystals from n-chlorobutane.

m.p.=130–132° C.; MS(FD): m/e=538 (M$^+$).

EXAMPLE 15

Methyl 2-[3(R)-(4(R)-phenyloxazolidin-2-on-3-yl)-4 (S)-(1-(fur-2-yl)ethylen-2-yl)azetidin-2-on-1-yl] acetate Beginning with 3.75 gm (42 mMol) glycine methyl ester and one equivalent of 3-(2-furyl)acrolein, the corresponding imine was prepared by Method A. This imine and 1.1 equivalents of 2-(4(R)-phenyloxazolidin-2-on-3-yl)acetyl chloride were subjected to the 2+2 cycloaddition conditions (Method B) to provide 7.0 gm (42%) of the title compound as off-white crystals from n-chlorobutane.

MS(FD): m/e=396 (M$^+$); EA: Calculated for: $C_{21}H_{20}N_2O_6$. Theory: C, 63.63; H, 5.09; N, 7.07. Found: C, 63.45; H, 5.18; N, 6.80.

The compounds of Examples 16 and 17 were prepared by the methodology described in Example 15.

EXAMPLE 16

Benzyl 2(S)-isobutyl-2-[3(R)-(4(R)-phenyloxazolidin-2-on-3-yl)-4(S)-(1-(fur-2-yl) ethylen-2-yl)azetidin-2-on-1-yl]acetate Beginning with 5.0 gm (22.6 mMol) (L)-leucine benzyl ester, the title compound was recovered as an off-white solid from n-chlorobutane.

MS(FD): m/e=528 (M$^+$); EA: Calculated for: $C_{31}H_{32}N_2O_6$. Theory: C, 70.44; H, 6.10; N, 5.30. Found: C, 70.68; H, 6.04; N, 5.44.

EXAMPLE 17

Methyl 2(S)-(2,2-dimethyl)propyl-2-[3(R)-(4(R)-phenyloxazolidin-2-on-3-yl)-4(S)-(1-(fur-2-yl) ethylen-2-yl)azetidin-2-on-1-yl]acetate Beginning with 0.542 gm (3.4 mMol) 4-methyl-(L)-leucine methyl ester, 0.995 gm (63%) of the title compound were recovered.

MS(FD): m/e=466 (M$^+$).

EXAMPLE 18

2-(Trimethylsilyl)ethyl 2-[(1,1-ethyleneketal) propionyl]-2-[3(S)-azido-4(R)-(2-styryl)azetidin-2-on-1-yl]acetate and 2-(Trimethylsilyl)ethyl 2-[(1,1-ethyleneketal)propionyl]-2-[3(R)-azido-4(S)-(2-styryl)azetidin-2-on-1-yl]acetate Beginning with 1.5 gm (5.45 mMol) 2-(trimethylsilyl)-ethyl 2-amino-3,3-(ethyleneketal)propionylacetate and one equivalent of cinnamaldehyde, the corresponding imine was prepared by Method A. This imine and 1.1 equivalents of 2-azidoacetyl chloride were subjected to the 2+2 cycloaddition conditions (Method B) to provide a mixture of the title compounds. This mixture was subjected to silica gel chromatography, eluting with 2:3 ethyl acetate:hexane to provide each of the title diasteromeric mixtures. The earlier eluting fractions provided, upon evaporation, 0.75 gm (31%) of one diasteromeric mixture.

MS(FD): m/e=448 (M$^+$).

The later eluting fractions provided, upon evaporation, 0.615 gm (25%) of the other diastereomeric mixture.

MS(FD): m/e=448 (M$^+$).

EXAMPLE 19

Benzyl 2-[3-(4,5-diphenyloxazol-2-on-1-yl)-4-(2-styryl)azetidin-2-on-1-yl]acetate Beginning with 1.0 gm (6.1 mMol) glycine benzyl ester and one equivalent of cinnamaldehyde, the corresponding imine was prepared by Method A. This imine and 1.1 equivalents of 2-(4,5-diphenyloxazol-2-on-1-yl)acetyl chloride (Miller, M. J., *Journal of Organic Chemistry*, 58, 618–625, (1993)) were subjected to the 2+2 cycloaddition conditions (Method B) to provide 0.32 gm (9.4%) of the title compound.

EXAMPLE 20

Benzyl 2-[3-(N-(phenoxyacetyl)amino)-4-(2-styryl) azetidin-2-on-1-yl]acetate

A slurry of 2.18 gm (6.77 mMol) 3-(N-(phenoxyacetyl)-amino)-4-(2-styryl)azetidinone (Branch and Pearson, *J. Chem. Soc., Perkin Trans. I*, 2123–2129 (1982)), 0.93 gm (6.77 mMol) potassium carbonate and 2.2 gm (6.77 mMol) cesium carbonate in 20 mL acetonitrile was prepared. To this slurry was added a solution of 1.87 gm (6.77 mMol) benzyl iodoacetate in 25 mL dimethylformamide and the resultant mixture was heated at 60° C. for 1.5 hours. The reaction mixture was then diluted with 200 mL ethyl acetate and was then washed sequentially with water, 1N hydrochloric acid, and saturated aqueous sodium chloride. The remaining organics were dried over magnesium sulfate and concentrated under reduced pressure. The residue after concentration was subjected to silica gel chromatography, eluting with 1:1 hexane:ethyl acetate. Fractions shown to contain product were combined and concentrated under reduced pressure to provide an orange foam which was recrystallized from n-chlorobutane to yield the title compound as a light yellow solid.

MS(FD): m/e=470 (M$^+$); EA: Calculated for: $C_{28}H_{26}N_2O_5$. Theory: C, 71.48; H, 5.57; N, 5.95. Found: C, 71.65; H, 5.69; N, 5.97.

EXAMPLE 21

2-[3(S)-(4(S)-phenyloxazolidin-2-on-3-yl)-4(R)-(2-styryl)azetidin-2-on-1-yl]acetic acid To a solution of 1.0 gm (2.23 mMol) tert-butyl 2-[3(S)-(4(S)-phenyloxazolidin-2-on-3-yl)-4(R)-(2-styryl)azetidin-2-on-1-yl]acetate (Example 2) in 5 mL dichloromethane was added 2 mL trifluoroacetic acid. The reaction mixture was stirred at room temperature for one hour at which point it was concentrated under reduced pressure. The residue after evaporation was crystallized from acetonitrile to provide 0.691 gm (80%) of the title compound as a colorless solid.

m.p.=215° C. (dec.); MS(FD): m/e=393 (M+1).

EXAMPLE 22

2-(S)-isobutyl-2-[3(S)-(4(S)-phenyloxazolidin-2-on-3-yl)-4(R)-(2-styryl)azetidin-2-on-1-yl]acetic acid To a slurry of 5.46 gm (11.8 mMol) methyl 2-(S)-isobutyl-2-[3(S)-(4(S)-phenyloxazolidin-2-on-3-yl)-4(R)-(2-styryl)-azetidin-2-on-1-yl]acetate (Example 6) in 100 mL tetrahydrofuran and 30 mL water was added 2.36 gm (59 mMol) sodium hydroxide. After stirring for 1.5 hour at room temperature, the reaction mixture was partitioned between 100 mL water and 100 mL ethyl acetate. The pH of the mixture was adjusted to less than 2 with hydrochloric acid and the phases were separated. The organic phase was washed sequentially with water and saturated aqueous sodium chloride, dried over magnesium sulfate and concentrated under reduced pressure to provide 4.6 gm (86%) of the title compound as a colorless solid.

m.p.=202–204° C.; MS(FD): m/e=449 (M+1).

EXAMPLE 23

2-[(1,1-ethyleneketal)propionyl]-2-[3(S)-(4(S)-phenyloxazolidin-2-on-3-yl)-4(R)-(2-styryl)azetidin-2-on-1-yl]acetic acid To a solution of 0.510 gm (0.86 mMol) 2-(trimethylsilyl)ethyl 2-[(1,1-ethyleneketal)propionyl]-2-[3(S)-(4(S)-phenyloxazolidin-2-on-3-yl)-4(R)-(2-styryl)azetidin-2-on-1-yl]acetate (Example 13) in 2 mL anhydrous dimethylformamide were added 0.67 gm (2.6 mMol) tetrabutylammonium fluoride and the reaction mixture was stirred for 15 minutes at room temperature. The reaction mixture was then diluted with ethyl acetate and the pH adjusted to 1 with 1N hydrochloric acid. The mixture was washed well with water, dried over magnesium sulfate and concentrated under reduced pressure to give 0.425 gm (100%) of the title compound as a colorless solid. This material was recrystallized from n-chlorobutane containing a small amount of acetonitrile for analysis, providing a colorless solid.

m.p.=187–192° C.; MS(FD): m/e=492 (M$^+$).

EXAMPLE 24

2-[(1,1-ethyleneketal)acetyl]-2-[3(S)-(4(S)-phenyloxazolidin-2-on-3-yl)-4(R)-(2-styryl)azetidin-2-on-1-yl]acetic acid Beginning with 1.42 gm (2.46 mMol) 2-(trimethylsilyl)ethyl 2-[(1,1-ethyleneketal)acetyl]-2-[3(S)-(4(S)-phenyloxazolidin-2-on-3-yl)-4(R)-(2-styryl)azetidin-2-on-1-yl]acetate (Example 12), 1.18 gm (98%) of the title compound were prepared by the procedure described in Example 23.

m.p.=194–195° C.; EA: Calculated for: $C_{26}H_{26}N_2O_7$. Theory: C, 65.26; H, 5.48; N, 5.85. Found: C, 64.99; H, 5.51; N, 5.92.

EXAMPLE 25

2-(S)-(2,2-dimethylpropyl)-2-[3(S)-(4(S)-phenyloxazolidin-2-on-3-yl)-4(R)-(2-styryl)azetidin-2-on-1-yl]acetic acid A mixture of 0.50 gm (0.96 mMol) tert-butyl 2-(S)-(2,2-dimethylpropyl)-2-[3(S)-(4(S)-phenyloxazolidin-2-on-3-yl)-4(R)-(2-styryl)azetidin-2-on-1-yl]acetate (Example 9), 7 mL trifluoroacetic acid, and 3.5 mL triethylsilane at 0° C. was allowed to warm to room temperature over 1 hour. The reaction mixture was concentrated under reduced pressure and the residue crystallized from n-chlorobutane to provide the title compound as a crystalline solid.

m.p.=208–209° C.; MS(FD): m/e=462 (M$^+$).

EXAMPLE 26

Benzyl 2-(R,S)-isopropyl-2-[3(S)-(4(S)-phenyloxazolidin-2-on-3-yl)-4(R)-(2-styryl)azetidin-2-on-1-yl]acetate Hydrolysis to Carboxylic Acid A solution of 0.10 gm (0.22 mMol) methyl 2-(R,S)-isopropyl-2-[3(S)-(4(S)-phenyloxazolidin-2-on-3-yl)-4(R)-(2-styryl)azetidin-2-on-1-yl]acetate (Example 6) was treated with 0.56 mL 1N sodium hydroxide and the resulting mixture was stirred at room temperature for 2 hours. The pH of the reaction mixture was then adjusted to less than 2 by the addition of 1N hydrochloric acid and it was then extracted with ethyl acetate. The phases were separated, the organics dried over magnesium sulfate, and then concentrated under reduced pressure to provide 2-(R,S)-isopropyl-2-[3(S)-(4(S)-phenyloxazolidin-2-on-3-yl)-4(R)-(2-styryl)azetidin-2-on-1-yl]acetic acid.

Benzyl Ester Formation Via Acid Chloride

The 2-(R,S)-isopropyl-2-[3(S)-(4(S)-phenyloxazolidin-2-on-3-yl)-4(R)-(2-styryl)azetidin-2-on-1-yl]acetic acid prepared in the previous paragraph was dissolved in 2 mL dichloromethane and to this solution was added 0.019 mL (0.28 mMol) oxalyl chloride followed by 0.1 mL dimethylformamide. The reaction mixture was stirred for 30 minutes at room temperature and was then concentrated under reduced pressure. The residual acid chloride was dissolved in 2 mL tetrahydrofuran and to the solution was added 28.5 mg (0.26 mMol) benzyl alcohol. The reaction mixture was stirred for 30 minutes at room temperature and was then concentrated under reduced pressure. The residue was purified by thin layer chromatography (2 mm silica gel plate), eluting with 2:1 hexane:ethyl acetate, providing 30 mg (26%) of the title compound as an off-white solid.

m.p.=175–179° C.; MS(FD): m/e=523 (M$^+$).

EXAMPLE 27

Benzyl 2(S)-(2,2-dimethyl)propyl-2-[3(R)-(4(R)-phenyloxazolidin-2-on-3-yl)-4(S)-(1-(fur-2-yl)ethylen-2-yl)azetidin-2-on-1-yl]acetate Hydrolysis of Methyl Ester To a solution of 0.64 gm (1.37 mMol) methyl 2(S)-(2,2-dimethyl)propyl-2-[3(R)-(4(R)-phenyloxazolidin-2-on-3-yl)- 4(S)-(1-(fur-2-yl)ethylen-2-yl)azetidin-2-on-1-yl]acetate (Example 17) in 25 mL tetrahydrofuran at 10° C. was added 1.37 mL 1N sodium hydroxide. The reaction mixture was allowed to warm to room temperature over 2 hours. The reaction mixture was concentrated under reduced pressure and the residue partitioned between ethyl acetate and water. The phases were separated and the organic phase washed with saturated aqueous sodium bicarbonate. The aqueous phases were combined and the pH of the solution adjusted to less than 2 with hydrochloric acid. The aqueous phase was then extracted well with ethyl acetate. These organic extracts were combined, dried over magnesium sulfate and concentrated under reduced pressure to provide 2(S)-(2,2-dimethyl)propyl-2-[3(R)-(4(R)-phenyloxazolidin-2-on-3-yl)-4(S)-(1-(fur-2-yl)ethylen-2-yl)azetidin-2-on-1-yl]acetic acid.

Benzyl Ester Formation Via Alkylation of Carboxylate

To a mixture of 0.146 gm (0.32 mMol) 2(S)-(2,2-dimethyl)propyl-2-[3(R)-(4(R)-phenyloxazolidin-2-on-3-yl)-4(S)-(1-(fur-2-yl)ethylen-2-yl)azetidin-2-on-1-yl]acetic acid prepared in the previous paragraph and 0.022 gm (0.16 mMol) powdered, anhydrous potassium carbonate in 20 mL dimethylsulfoxide was added 0.038 mL (0.32 mMol) benzyl bromide. The reaction mixture was stirred for 18 hours at room temperature, at which time it was partitioned between ethyl acetate and saturated aqueous sodium chloride. The aqueous phase was extracted well with ethyl acetate. The organic phases were combined, dried over sodium sulfate and concentrated under reduced pressure. The residue was subjected to silica gel chromatography, eluting with 1:1 ethyl acetate:hexane. Fractions containing product were combined and concentrated under reduced pressure to provide 0.050 gm (67%) of the title compound as a colorless solid.

m.p.=180° C.; MS(FD): m/e=542 (M$^+$).

EXAMPLE 28

Benzyl 2-(S)-isobutyl-2-[3(S)-(4(S)-phenyloxazolidin-2-on-3-yl)-4(R)-(2-(phenyl)ethyl)azetidin-2-on-1-yl]acetate 2-(S)-isobutyl-2-[3(S)-(4(S)-phenyloxazolidin-2-on-3-yl)-4(R)-(2-(phenyl)ethyl)azetidin-2-on-1-yl]acetic acid A mixture of 1.04 gm (1.93 mMol) benzyl 2-(S)-isobutyl-2-[3(S)-(4(S)-phenyloxazolidin-2-on-3-yl)-4(R)-(2-styryl)-azetidin-2-on-1-yl]acetate (Example 7) and 0.15 gm 5% palladium on carbon in 50 mL 1:1 dichloromethane:ethyl acetate was hydrogenated at room temperature for 4 hours under an initial hydrogen pressure of 50 p.s.i. The reaction mixture was then filtered and the filtrate concentrated under reduced pressure to provide 0.79 gm (91%) of the desired compound as a colorless solid.

Preparation of the Benzyl Ester Via a Mixed Anhydride

A solution of 0.79 gm (1.76 mMol) 2-(S)-isobutyl-2-[3(S)-(4(S)-phenyloxazolidin-2-on-3-yl)-4(R)-(2-(phenyl)-ethyl)azetidin-2-on-1-yl]acetic acid in 20 mL dichloromethane was cooled to −4° C. To this solution were added 0.26 mL (1.85 mMol) triethylamine followed by 0.26 mL (1.85 mMol) benzyl chloroformate. After 5 minutes 0.20 mL (1.93 mMol) benzyl alcohol were added and the reaction mixture was allowed to warm to room temperature over 1 hour. The reaction mixture was then washed sequentially with two portions each of 1 N hydrochloric acid, saturated aqueous sodium bicarbonate and saturated aqueous sodium chloride. The remaining organics were dried over magnesium sulfate and concentrated under reduced pressure. The residue was subjected to silica gel chromatography, eluting with 1:1 hexane: ethyl acetate to provide the title compound as a colorless, crystalline solid.

m.p.=138–140° C.; MS(FD): m/e=540 (M$^+$).

EXAMPLE 29

N-[4-Methoxybenzyl]-2-[(1,1-ethyleneketal)acetyl]-2-[3(S)-(4(S)-phenyloxazolidin-2-on-3-yl)-4(R)-(2-styryl)azetidin-2-on-1-yl]acetamide To a solution of 0.162 gm (0.34 mMol) 2-[(1,1-ethyleneketal)acetyl]-2-[3(S)-(4(S)-phenyloxazolidin-2-on-3-yl)-4(R)-(2-styryl)azetidin-2-on-1-yl]acetic acid (Example 24) and 0.06 mL (0.74 mMol) pyridine in 3 mL tetrahydrofuran at 0° C. was added 0.05 mL (0.041 mMol) isobutylchloroformate. After stirring for 15 minutes, 0.05 mL (0.041 mMol) 4-methoxybenzylamine were added and the reaction mixture was allowed to warm to room temperature over 20 minutes. At this point the reaction mixture was diluted with ethyl acetate and was then washed sequentially with two portions each of 1N hydrochloric acid, saturated aqueous sodium bicarbonate and saturated aqueous sodium chloride. The remaining organics were dried over magnesium sulfate and concentrated under reduced pressure. The residue was crystallized from n-chlorobutane to provide the title compound as a colorless, crystalline solid.

MS(FD): m/e=597 (M+1); EA: Calculated for: $C_{34}H_{35}N_3O_7$. Theory: C, 68.33; H, 5.90; N, 7.03. Found: C, 68.49; H, 5.75; N, 7.12.

The compounds of Examples 30–32 were prepared by the procedure described in Example 29.

EXAMPLE 30

N-[Benzyl]-2-[(1,1-ethyleneketal)acetyl]-2-[3(S)-(4(S)-phenyloxazolidin-2-on-3-yl)-4(R)-(2-styryl)azetidin-2-on-1-yl]acetamide Beginning with 0.46 gm (0.96 mMol) 2-[(1,1-ethyleneketal)acetyl]-2-[3(S)-(4(S)-phenyloxazolidin-2-on-3-yl)-4(R)-(2-styryl)azetidin-2-on-1-yl]acetic acid (Example 24), 0.20 gm (37%) of the title compound was recovered as a colorless solid.

m.p.=150–152° C.; MS(FD): m/e=567 (M$^+$).

EXAMPLE 31

N-[benzyl]-2-[(1,1-ethyleneketal)propionyl]-2-[3(S)-(4(S)-phenyloxazolidin-2-on-3-yl)-4(R)-(2-styryl)azetidin-2-on-1-yl]acetamide Beginning with 0.10 gm (0.20 mMol) 2-[(1,1-ethyleneketal)propionyl]-2-[3(S)-(4(S)-phenyloxazolidin-2-on-3-yl)-4(R)-(2-styryl)azetidin-2-on-1-yl]acetic acid (Example 23), 0.040 gm (34%) of the title compound was recovered as a colorless, crystalline solid.

MS(FD): m/e=581 (M$^+$).

EXAMPLE 32

N-[benzyl]-2-[3(S)-(4(S)-phenyloxazolidin-2-on-3-yl)-4(R)-(2-styryl)azetidin-2-on-1-yl]acetamide Beginning with 2.0 gm (5.1 mMol) 2-[3(S)-(4(S)-phenyloxazolidin-2-on-3-yl)-4(R)-(2-styryl)azetidin-2-on-

EXAMPLE 33

1-{2-[3(S)-(4(S)-phenyloxazolidin-2-on-3-yl)-4(R)-
(2-styryl)azetidin-2-on-1-yl]acetyl}-4-(2-(piperidin-
1-yl)ethyl)piperidine A solution of 1.83 gm (4.7 mMol) 2-[3(S)-(4(S)-phenyloxazolidin-2-on-3-yl)-4(R)-(2-styryl)azetidin-2-on-1-yl]acetic acid (Example 21) in 20 mL dichloromethane was cooled to 0° C. To this solution was added 0.51 mL (5.8 mMol) oxalyl chloride followed by 0.10 mL dimethylformamide. The reaction mixture was allowed to warm to room temperature over 30 minutes. At this point volatiles were removed under reduced pressure to provide 2-[3(S)-(4(S)-phenyloxazolidin-2-on-3-yl)-4(R)-(2-styryl)azetidin-2-on-1-yl]acetyl chloride as an oil.

The acid chloride prepared in this manner was dissolved in 20 mL tetrahydrofuran and to this was added a solution of 4.7 mMol 4-(2-(piperidin-1-yl)ethyl)piperidine in 2 mL tetrahydrofuran. After stirring for 30 minutes, the reaction mixture was partitioned between water and ethyl acetate. The pH of the mixture was adjusted to greater than 7 by the addition of sodium bicarbonate and the phases were separated. The organic phase was washed with saturated aqueous sodium chloride, dried over magnesium sulfate and concentrated under reduced pressure to provide 1.4 gm (52%) of the title compound as a colorless foam.

MS(FD): m/e=570 (M+).

EXAMPLE 34

1-{2-(S)-isobutyl-2-[3(S)-(4(S)-phenyloxazolidin-2-
on-3-yl)-4(R)-(2-styryl)azetidin-2-on-1-yl]acetyl}-4-
(2-(piperidin-1-yl)ethyl)piperidine A mixture of 0.448 gm (1 mMol) 2-(S)-isobutyl-2-[3(S)-(4(S)-phenyloxazolidin-2-on-3-yl)-4(R)-(2-styryl)azetidin-2-on-1-yl]acetic acid (Example 22), 0.27 gm (2 mMol) cyanuric fluoride and 0.163 mL pyridine was heated at reflux for 2 hours. Ice was added to the reaction mixture and the resulting suspension was filtered. The organic phase of the filtrate was washed quickly with cold water, dried over sodium sulfate and concentrated under reduced pressure. The residue was suspended in hexane and filtered to provide 2-(S)-isobutyl-2-[3(S)-(4(S)-phenyloxazolidin-2-on-3-yl)-4(R)-(2-styryl)azetidin-2-on-1-yl]acetyl fluoride.

MS(FD): m/e=451 (M+1).

The acid fluoride was dissolved in dichloromethane and cooled to 0° C. To this solution was then added 1.05 mMol 4-(2-(piperidin-1-yl)ethyl)piperidine and the reaction mixture was allowed to warm to room temperature over 30 minutes. The reaction mixture was washed with saturated aqueous sodium bicarbonate, dried over magnesium sulfate and concentrated under reduced pressure. The residue was subjected to silica gel chromatography, eluting with dichloromethane containing 0 to 10% methanol to provide the title compound as a viscous oil.

MS(FD): m/e=626 (M+).

EXAMPLE 35

1-{2-(S)-(2,2-dimethylpropyl)-2-[3(S)-(4(S)-
phenyloxazolidin-2-on-3-yl)-4(R)-(2-styryl)azetidin-
2-on-1-yl]acetyl}-4-(2-(piperidin-1-yl)ethyl)
piperidine Beginning with 2-(S)-(2,2-dimethylpropyl)-2-[3(S)-(4(S)-phenyloxazolidin-2-on-3-yl)-4(R)-(2-styryl)azetidin-2-on-1-yl]acetic acid (Example 25), the title compound was prepared by the procedure described in Example 34.

MS(FD): m/e=640 (M+).

EXAMPLE 36

N-[2-(S)-isobutyl-2-[3(S)-(4(S)-phenyloxazolidin-2-
on-3-yl)-4(R)-(2-styryl)azetidin-2-on-1-yl]acetyl]-
(L)-phenylglycine allyl ester To a solution of 0.36 gm (0.8 mMol) 2-(S)-isobutyl-2-[3(S)-(4(S)-phenyloxazolidin-2-on-3-yl)-4(R)-(2-styryl)azetidin-2-on-1-yl]acetic acid (Example 22) in 10 mL dichloromethane were added 0.13 gm (0.96 mMol) 1-hydroxybenzotriazole and 0.18 gm (0.96 mMol) 1-(3-dimethylaminopropyl)-3-ethylcarbodiimide hydrochloride. After stirring this mixture for 5 minutes at room temperature, 0.88 mMol (L)-phenylglycine allyl ester was added and the reaction mixture stirred for 2 hours at room temperature. The reaction mixture was diluted with ethyl acetate and then washed sequentially with two portions each of 1N hydrochloric acid, saturated aqueous sodium bicarbonate and saturated aqueous sodium chloride. The remaining organics were dried over magnesium sulfate and concentrated under reduced pressure to provide 0.305 gm (61%) of the title compound as a colorless, crystalline solid.

m.p.=73–76° C.; MS(FD): m/e=622 (M+).

EXAMPLE 37

Methyl 2-(R,S)-[1-hydroxy-2,2-dimethylpropyl]-2-
[3(R)-(4(R)-phenyloxazolidin-2-on-3-yl)-4(S)-(1-
(fur-2-yl)ethylen-2-yl)azetidin-2-on-1-yl]acetate To a solution of 2.38 gm (6.0 mMol) methyl 2-[3(R)-(4(R)-phenyloxazolidin-2-on-3-yl)-4(S)-(1-(fur-2-yl)ethylen-2-yl)azetidin-2-on-1-yl]acetate (Example 15) in 150 mL tetrahydrofuran at −78° C. was added dropwise 6.6 mL (6.6 mMol) lithium hexamethyldisilazane (1.0 M in tetrahydrofuran) at such a rate as to maintain the internal temperature of the reaction mixture at −78° C. After the anion had formed, as distinguished by a characteristic red color of the solution, 0.648 mL (6.0 mMol) pivalaldehyde was added. The color of the anion discharged within 5 minutes. The reaction mixture was treated with saturated aqueous ammonium chloride followed by ethyl acetate. The phases were separated and the organic phase was washed with saturated aqueous sodium bicarbonate followed by saturated aqueous sodium chloride. The remaining organics were dried over sodium sulfate and concentrated under reduced pressure to provide 2.0 gm (69%) of the crude title compound as a tan solid. This material was subjected to silica gel chromatography, eluting with 1:1 hexane:ethyl acetate. Fractions shown to contain product were combined and concentrated under reduced pressure to provide the title compound as a colorless, crystalline mass.

MS(FD): m/e=482 (M+); EA: Calculated for: $C_{26}H_{30}N_2O_7$. Theory: C, 64.72; H, 6.27; N, 5.81. Found: C, 64.90; H, 6.53; N, 5.55.

The compounds of Examples 38–40 were prepared by the procedure described in Example 37.

EXAMPLE 38

Benzyl 2(R,S)-[1-hydroxy-2,2-dimethylpropyl]-2-[3
(S)-(4(S)-phenyloxazolidin-2-on-3-yl)-4(R)-(2-
styryl)azetidin-2-on-1-yl]acetate Beginning with benzyl 2-[3(S)-(4(S)-phenyloxazolidin-2-on-3-yl)-4(R)-(2-styryl)azetidin-2-on-1-yl]acetate (Example 3), the title compound was prepared.

MS(FD): m/e=568 (M⁺); EA: Calculated for: $C_{34}H_{36}N_2O_6$. Theory: C, 71.81; H, 6.38; N, 4.93. Found: C, 71.56; H, 6.33; N, 5.09.

EXAMPLE 39

Methyl 2-(R,S)-[1-hydroxy-1,2-diphenyl-2-oxo-ethyl]-2-[3(R)-(4(R)-phenyloxazolidin-2-on-3-yl)-4(S)-(1-(fur-2-yl)ethylen-2-yl)azetidin-2-on-1-yl] acetate Beginning with methyl 2-[3(R)-(4(R)-phenyloxazolidin-2-on-3-yl)-4(S)-(1-(fur-2-yl)ethylen-2-yl)azetidin-2-on-1-yl]acetate (Example 15) and benzil, the title compound was prepared.

MS(FD): m/e=606 (M⁺).

EXAMPLE 40

1-{2-(R,S)-[1-hydroxy-2,2-dimethylpropyl]-2-[3(S)-(4(S)-phenyloxazolidin-2-on-3-yl)-4(R)-(2-styryl) azetidin-2-on-1-yl]acetyl}-4-(2-(piperidin-1-yl) ethyl)piperidine and 1-{2,2-di-[1-hydroxy-2,2-dimethylpropyl]-2-[3(S)-(4(S)-phenyloxazolidin-2-on-3-yl)-4(R)-(2-styryl) azetidin-2-on-1-yl]acetyl}-4-(2-(piperidin-1-yl) ethyl)piperidine Beginning with 1-{2-[3(S)-(4(S)-phenyloxazolidin-2-on-3-yl)-4(R)-(2-styryl)azetidin-2-on-1-yl]acetyl}-4-(2-(piperidin-1-yl)ethyl)piperidine (Example 33), each of the title compounds was isolated.

1-{2-(R,S)-[1-hydroxy-2,2-dimethylpropyl]-2-[3(S)-(4(S)-phenyloxazolidin-2-on-3-yl)-4(R)-(2-styryl) azetidin-2-on-1-yl]acetyl}-4-(2-(piperidin-1-yl) ethyl)piperidine MS(FD): m/e=656 (M⁺).

1-{2,2-di-[1-hydroxy-2,2-dimethylpropyl]-2-[3(S)-(4(S)-phenyloxazolidin-2-on-3-yl)-4(R)-(2-styryl) azetidin-2-on-1-yl]acetyl}-4-(2-(piperidin-1-yl) ethyl)piperidine MS(FD): m/e=742 (M⁺).

EXAMPLE 41

Benzyl 2-(R,S)-[2-methylpropanoyl]-2-[3(S)-(4(S)-phenyloxazolidin-2-on-3-yl)-4(R)-(2-styryl)azetidin-2-on-1-yl]acetate A solution of 0.52 gm (1.1 mMol) benzyl 2-[3(S)-(4(S)-phenyloxazolidin-2-on-3-yl)-4(R)-(2-styryl)azetidin-2-on-1-yl]acetate (Example 3) in 5 mL tetrahydrofuran was cooled to −78° C. To this solution was then added 2.4 mL (2.4 mMol) lithium bis(trimethylsilyl)amide (1M in hexane) dropwise over about 5 minutes. The reaction mixture was stirred for 2 minutes after the addition was complete and then 0.13 mL (1.21 mMol) isobutyryl chloride was added. The reaction mixture was stirred for 5 minutes at −78° C. and then the reaction was quenched by the addition of saturated aqueous ammonium chloride. The reaction mixture was then partitioned between ethyl acetate and water. The phases were separated and the organic phase was washed sequentially with two portions each of 1N hydrochloric acid, saturated aqueous sodium bicarbonate and saturated aqueous sodium chloride. The remaining organics were dried over magnesium sulfate and concentrated under reduced pressure. The residual foam was subjected to silica gel chromatography, eluting with 3:2 hexane:ethyl acetate. Fractions shown to contain product were combined and concentrated under reduced pressure to provide 0.46 gm (76%) of the title compound as a colorless foam.

MS(FD): m/e=552 (M⁺); EA: Calculated for: $C_{33}H_{32}N_2O_6$. Theory: C, 71.72; H, 5.84; N, 5.07. Found: C, 71.90; H, 5.66; N, 5.21.

The compounds of Examples 42–53 were prepared by the procedure described in Example 41.

EXAMPLE 42

Benzyl 2-(R,S)-[2,2-dimethylpropanoyl]-2-[3(S)-(4(S)-phenyloxazolidin-2-on-3-yl)-4(R)-(2-styryl) azetidin-2-on-1-yl]acetate Beginning with 4.82 gm (10.0 mMol) benzyl 2-[3(S)-(4(S)-phenyloxazolidin-2-on-3-yl)-4(R)-(2-styryl)azetidin-2-on-1-yl]acetate (Example 3) and pivaloyl chloride, 5.0 gm (88%) of the title compound was recovered as a white solid.

m.p.=176–179° C.; MS(FD): m/e 566 (M⁺).

EXAMPLE 43

Benzyl 2(R,S)-[cyclopropylcarbonyl]-2-[3(S)-(4(S)-phenyloxazolidin-2-on-3-yl)-4(R)-(2-styryl)azetidin-2-on-1-yl]acetate Beginning with 1.15 gm (2.38 mMol) benzyl 2-[3(S)-(4(S)-phenyloxazolidin-2-on-3-yl)-4(R)-(2-styryl)azetidin-2-on-1-yl]acetate (Example 3) and cyclopropylcarbonyl chloride, 0.75 gm (57%) of the title compound was recovered.

MS(FD): m/e=550 (M⁺). EA: Calculated for: $C_{33}H_{30}N_2O_6$. Theory: C, 71.98; H, 5.09; N, 5.09. Found: C, 71.69; H, 5.81; N, 5.78.

EXAMPLE 44

Benzyl 2(R,S)-[benzoyl]-2-[3(S)-(4(S)-phenyloxazolidin-2-on-3-yl)-4(R)-(2-styryl)azetidin-2-on-1-yl]acetate Beginning with 1.00 gm (2.07 mMol) benzyl 2-[3(S)-(4(S)-phenyloxazolidin-2-on-3-yl)-4(R)-(2-styryl)azetidin-2-on-1-yl]acetate (Example 3) and benzoyl chloride, 0.54 gm (44%) of the title compound was recovered as a colorless solid.

MS(FD): m/e=587 (M⁺); EA: Calculated for: $C_{36}H_{30}N_2O_6$. Theory: C, 73.71; H, 5.16; N, 4.78. Found: C, 73.52; H, 5.01; N, 4.81.

EXAMPLE 45

4-Nitrobenzyl 2(R,S)-[2,2-dimethylpropanoyl]-2-[3(S)-(4(S)-phenyloxazolidin-2-on-3-yl)-4(R)-(2-styryl)azetidin-2-on-1-yl]acetate Beginning with 2.21 gm (4.19 mMol) 4-nitrobenzyl 2-[3(S)-(4(S)-phenyloxazolidin-2-on-3-yl)-4(R)-(2-styryl) azetidin-2-on-1-yl]acetate (Example 4) and pivaloyl chloride, 1.60 gm (63%) of the title compound was recovered as an off-white foam.

MS(FD): m/e=611 (M⁺); EA: Calculated for: $C_{34}H_{33}N_3O_8$. Theory: C, 63.89; H, 5.19; N, 6.98. Found: C, 63.75; H, 5.37; N, 7.25.

EXAMPLE 46

3-Chlorobenzyl 2(R,S)-[2,2-dimethylpropanoyl]-2-[3(S)-(4(S)-phenyloxazolidin-2-on-3-yl)-4(R)-(2-styryl)azetidin-2-on-1-yl]acetate Preparation of 3-Chlorobenzyl 2-[3(S)-(4(S)-phenyloxazolidin-2-on-3-yl)-4(R)-(2-styryl)azetidin-2-on-1-yl]acetate Beginning with 0.285 gm (0.72 mMol) 2-[3(S)-(4(S)-phenyloxazolidin-2-on-3-yl)-4(R)-(2-styryl)azetidin-2-on- 1-yl]acetic acid (Example 21) and ethyl chloroformate, 0.085 gm (23%) 3-chlorobenzyl 2-[3(S)-(4(S)-phenyloxazolidin-2-on-3-yl)-4(R)-(2-styryl)azetidin-2-on-1-yl]acetate were recovered by the procedure described in Example 29.

Acylation

Beginning with 0.085 gm (0.16 mMol) 3-chlorobenzyl 2-[3(S)-(4(S)-phenyloxazolidin-2-on-3-yl)-4(R)-(2-styryl) azetidin-2-on-1-yl]acetate and pivaloyl chloride, 0.11 gm of the title compound was recovered as an off-white foam.

MS(FD): m/e=601 (M$^+$).

EXAMPLE 47

Methyl 2(R,S)-[2,2-dimethylpropanoyl]-2-[3(S)-(4 (S)-phenyloxazolidin-2-on-3-yl)-4(R)-(2-styryl) azetidin-2-on-1-yl]acetate Beginning with 1.44 gm (3.5 mMol) methyl 2-[3(S)-(4 (S)-phenyloxazolidin-2-on-3-yl)-4(R)-(2-styryl)azetidin-2-on-1-yl]acetate (Example 1) and pivaloyl chloride, 0.30 gm (17%) of the title compound was recovered as a colorless foam.

m.p.=162° C.; MS(FD): m/e=490 (M$^+$).

EXAMPLE 48 tert-Butyl 2(R,S)-[2,2-dimethylpropanoyl]-2-[3(S)-(4(S)-phenyloxazolidin-2-on-3-yl)-4(R)-(2-styryl) azetidin-2-on-1-yl]acetate Beginning with 0.503 gm (1.12 mMol) tert-butyl 2-[3(S)-(4(S)-phenyloxazolidin-2-on-3-yl)-4(R)-(2-styryl)azetidin-2-on-1-yl]acetate (Example 2) and pivaloyl chloride, 0.30 gm (50%) of the title compound was recovered as an off-white solid.

MS (FD): m/e=611 (M$^+$); EA: Calculated for: $C_{31}H_{36}N_2O_6$. Theory: C, 69.91; H, 6.81; N, 5.26. Found: C, 69.87; H, 7.10; N, 5.47.

EXAMPLE 49 tert-Butyl 2(R,S)-[phenoxyacetyl]-2-r3(S)-(4(S)-phenyloxazolidin-2-on-3-yl)-4(R)-(2-styryl)azetidin-2-on-1-yl]acetate Beginning with 0.448 gm (1.0 mMol) tert-butyl 2-[3(S)-(4(S)-phenyloxazolidin-2-on-3-yl)-4(R)-(2-styryl)azetidin-2-on-1-yl]acetate (Example 2), 1.0 mL (1.0 mMol) lithium hexamethyldisilazane, and phenoxyacetyl chloride, 0.10 gm (17%) of the title compound was recovered.

MS(FD): m/e=582 (M$^+$); EA: Calculated for: $C_{34}H_{34}N_2O_7$. Theory: C, 70.09; H, 5.88; N, 4.81. Found: C, 69.84; H, 5.71; N, 4.86.

EXAMPLE 50 tert-Butyl 2(R,S)-[3-(trifluoro)phenylacetyl]-2-[3 (S)-(4(S)-phenyloxazolidin-2-on-3-yl)-4(R)-(2-styryl)azetidin-2-on-1-yl]acetate Beginning with tert-butyl 2-[3(S)-(4(S)-phenyloxazolidin-2-on-3-yl)-4(R)-(2-styryl)azetidin-2-on-1-yl]acetate (Example 2), lithium hexamethyldisilazane, and (3-trifluoromethyl)phenylacetyl chloride, the title compound was prepared.

m.p.=158–160° C.; MS(FD): m/e=634 (M$^+$).

EXAMPLE 51

Benzyl 2-[2,2-dimethylpropanoyl]-2-[3-(N-(phenoxyacetyl)amino)-4-(2-styryl)azetidin-2-on-1-yl]acetate Beginning with 0.57 gm (1.2 mMol) benzyl 2-[3-(N-(phenoxyacetyl)amino)-4-(2-styryl)azetidin-2-on-1-yl] acetate (Example 20) and pivaloyl chloride, 0.20 gm (30%) of the title compound was recovered as a colorless foam.

MS(FD): m/e=555 (M+1); EA: Calculated for: $C_{34}H_{34}N_2O_6$. Theory: C, 71.46; H, 6.18; N, 5.05. Found: C, 71.41; H, 6.43; N, 5.10.

EXAMPLE 52

Benzyl 2-[2,2-dimethylpropanoyl]-2-[3-(4,5-diphenyloxazol-2-on-1-yl)-4-(2-styryl)azetidin-2-on-1-yl]acetate Beginning with 0.32 gm (0.63 mMol) benzyl 2-[3-(4,5-diphenyloxazol-2-on-1-yl)-4-(2-styryl)azetidin-2-on-1-yl]-acetate (Example 19) and pivaloyl chloride, 0.10 gm (25%) of the title compound was recovered as a pale yellow foam.

MS(FD): m/e=640 (M$^+$).

EXAMPLE 53

Benzyl 2-(R,S)-[2,2-dimethylpropanoyl]-2-[3(S)-(4 (S)-phenyloxazolidin-2-on-3-yl)-4(R)-(1-(fur-2-yl) ethylen-2-yl)azetidin-2-on-1-yl]acetate Beginning with 0.50 gm (1.06 mMol) benzyl 2-[3(S)-(4 (S)-phenyloxazolidin-2-on-3-yl)-4(R)-(1-(fur-2-yl)ethylen-2-yl)azetidin-2-on-1-yl]acetate and pivaloyl chloride, 0.31 gm (56%) of the title compound was recovered as a white solid.

MS(FD): m/e=556 (M$^+$); EA: Calculated for: $C_{32}H_{32}N_2O_7$. Theory: C, 68.96; H, 5.80; N, 5.21. Found: C, 69.05; H, 5.79; N, 5.03.

EXAMPLE 54

Benzyl 2-(R)-[2,2-dimethylpropanoyl]-2-[3(S)-(4 (S)-phenyloxazolidin-2-on-3-yl)-4(R)-(1-(fur-2-yl) ethylen-2-yl)azetidin-2-on-1-yl]acetate and Benzyl 2-(S)-[2,2-dimethylpropanoylj-2-[3(S)-(4(S)-phenyloxazolidin-2-on-3-yl)-4(R)-(1-(fur-2-yl) ethylen- 2-yl)azetidin-2-on-1-yl]acetate A mixture of 0.385 gm benzyl 2-(R,S)-[2,2-dimethylpropanoyl]-2-[3(S)-(4(S)-phenyloxazolidin-2-on-1-yl)-4(R)-(1-(fur-2-yl)ethylen-2-yl)azetidin-2-on-1-yl] acetate (Example 53) in 7.0 mL ethyl acetate was heated until the mixture was a solution. To this solution was added 5 mL hexane and the mixture stirred for 1 hour at room temperature. A solid formed which was filtered to provide 0.125 gm of a single diastereomer (95% d.e. as determined by NMR) as a fluffy, colorless solid. The filtrate was concentrated under reduced pressure to provide 0.157 gm of the opposite diastereomer (90% d.e. as determined by NMR) as a tan solid.

EXAMPLE 55

1-[2-oxo-4-(tert-butyl)oxetan-2-yl]-3(S)-(4(S)-phenyloxazolidin-2-on-3-yl)-4(R)-(2-styryl)azetidin-2-one 2-(R,S)-[1-hydroxy-2,2-dimethylpropyl]-2-[3 (S)-(4(S)-phenyloxazolidin-2-on-3-yl)-4(R)-(2-styryl)azetidin-2-on-1-yl]-acetic acid A mixture of 1.5 mL trifluoroacetic acid and 0.75 mL triethylsilane at 0° C. were added to 0.10 gm (0.19 mMol) tert-butyl 2-(R,S)-[1-hydroxy-2,2-dimethylpropyl]-2-[3(S)-(4(S)-phenyloxazolidin-2-on-3-yl)-4(R)-(2-styryl)azetidin-2-on-1-yl]acetate (prepared from tert-butyl 2-[3(S)-(4(S)- phenyloxazolidin-2-on-3-yl)-4(R)-(2-styryl)azetidin-2-on-1-yl]acetate (Example 2) by the procedure described in Example 37). The mixture was allowed to warm to room temperature over 1 hour. The reaction mixture was then concentrated under reduced pressure and the residue crystallized from hexane to provide the desired compound as a crystalline solid.

MS(FD): m/e=478 (M$^+$); EA: Calculated for: $C_{27}H_{30}N_2O_6$. Theory: C, 67.77; H, 6.32; N, 5.85. Found: C, 67.78; H, 6.42; N, 6.03.

Lactonization

To a solution of 0.024 gm (0.05 mMol) 2-(R,S)-[1-hydroxy-2,2-dimethylpropyl]-2-[3(S)-(4(S)-phenyloxazolidin-2-on-3-yl)-4(R)-(2-styryl)azetidin-2-on-1-yl]acetic acid in 3 mL chloroform was added 0.125 mg (0.10 mMol) polystyrene supported 1-(3-dimethylaminopropyl)-3-ethylcarbodiimide. The mixture was agitated for 24 hours at room temperature. The reaction mixture was then filtered and the volatiles removed under reduced pressure to provide the title compound.

IR: 1833.5 cm$^{-1}$ (lactone carbonyl).

EXAMPLE 56

N-[benzyl]-N-[tert-butoxycarbonyl]-2-[3(S)-(4(S)-phenyloxazolidin-2-on-3-yl)-4(R)-(2-styryl)azetidin-2-on-1-yl]acetamide To a solution of 0.41 gm (0.85 mMol) N-[benzyl]-2-[3(S)-(4(S)-phenyloxazolidin-2-on-3-yl)-4(R)-(2-styryl) azetidin-2-on-1-yl]acetamide (Example 32) in 5 mL 1:1 acetonitrile:dichloromethane were added 0.20 gm (0.89 mMol) di-tert-butyl dicarbonate and a catalytic amount of dimethylaminopyridine. The reaction mixture was stirred for 17 hours at room temperature. The volatiles were then removed under reduced pressure and the residue crystallized from 95:5 n-chlorobutane:acetonitrile to provide 0.40 gm (80%) of the title compound as a colorless solid.

MS(FD): m/e=581 (M$^+$); EA: Calculated for: $C_{34}H_{35}N_3O_6$. Theory: C, 70.21; H, 6.07; N, 7.22. Found: C, 70.30; H, 6.13; N, 7.38.

General Procedure for the Preparation of Ureas

A solution of 0.013 gm (0.033 mMol) benzyl 2-isobutyl-2-[2-amino-3-styrylazetidin-2-on-1-yl]acetate (Preparation and 0.071 mMol of an appropriate isocyanate in 2 mL dichloromethane are agitated for 24 hours. To this solution is then added 0.127 gm (0.071 mMol) aminomethylated polystyrene resin and the reaction mixture agitated for an additional 24 hours. The reaction mixture is then filtered, the solid washed with dichloromethane and the combined filtrates concentrated under reduced pressure to provide the corresponding urea. The compounds of Examples 57–62 were prepared by this general procedure.

EXAMPLE 57

N-isopropyl-N'-[1-(1-benzyloxycarbonyl-4-methylbutyl)-4-(styryl)azetidin-2-on-3-yl]urea Using isopropylisocyanate, 9.3 mg (59%) of the title compound was prepared.

MS: m/e=478 (M+1).

EXAMPLE 58

N-hexyl-N'-[1-(1-benzyloxycarbonyl-4-methylbutyl)-4-(styryl)azetidin-2-on-3-yl]urea Using 1-hexylisocyanate, 9.9 mg (58%) of the title compound was prepared.

MS: m/e=520 (M+1).

EXAMPLE 59

N-cyclohexyl-N'-[1-(1-benzyloxycarbonyl-4-methylbutyl)-4-(styryl)azetidin-2-on-3-yl]urea Using cyclohexylisocyanate, 10.4 mg (61%) of the title compound was prepared.

MS: m/e 518 (M+1).

EXAMPLE 60

N-[2-(phenyl)ethyl]-N'-[1-(1-benzyloxycarbonyl-4-methylbutyl)-4-(styryl)azetidin-2-on-3-yl]urea Using 2-phenyl-1-ethylisocyanate, 11.3 mg (63%) of the title compound was prepared.

MS: m/e=540 (M+1).

EXAMPLE 61

N-[1-(ethoxycarbonyl)-2-(phenyl)ethyl]-N'-[1-(1-benzyloxycarbonyl-4-methylbutyl)-4(styryl)azetidin-2-on-3-yl]urea Using 1-ethoxycarbonyl-2-phenyl-1-ethylisocyanate, 14.7 mg (59%) of the title compound was prepared.

MS: m/e=612 (M+1).

EXAMPLE 62

N-phenyl-N'-[1-(1-benzyloxycarbonyl-4-methylbutyl)-4-(styryl)azetidin-2-on-3-yl]urea Using phenylisocyanate, 9.7 mg (57%) of the title compound was prepared.

MS: m/e=512 (M+1).

Solid Phase Reagent Method for the Preparation of Amides

To a solution of 0.05 mMol of a carboxylic acid in 2–3 ML chloroform are added 0.025 mMol of the desired primary or secondary amine and 0.100 mMol of divinylbenzene crosslinked polystyrene supported 1-(3-dimethylaminopropyl)-3-ethylcarbodiimide. The mixture was agitated for at least 18 hours or until complete as determined by thin layer chromatography. The reaction mixture was then filtered, the solid washed with chloroform, and the combined filtrates concentrated under reduced pressure to provide the desired amide.

The amides of Examples 63–80 were prepared by the procedure described above beginning with 2-[(1,1-ethyleneketal)propionyl]-2-[3(S)-(4(S)-phenyloxazolidin-2-on-3-yl)-4(R)-(2-styryl)azetidin-2-on-1-yl]acetic acid (Example 23).

| Example | Amine Radical | Yield (% Yield) | MS (m/e) |
|---|---|---|---|
| 63 | N-[4-(diethylamino)butyl]amino | 12.1 mg/(73%) | 618 (M⁺) |
| 64 | N-[2-(dimethylamino)ethyl]-N-benzylamino | 13.4 mg/(82%) | 653 (M + 1) |
| 65 | N-[3-(diethylamino)propyl]-N-benzylamino | 13.0 mg/(75%) | 695 (M + 1) |
| 66 | N-[(pyridin-3-yl)methyl]-amino | 9.8 mg/(67%) | 583 (M + 1) |
| 67 | N-[3-(trifluoromethyl)-benzyl]-amino | 11.6 mg/(71%) | 650 (M + 1) |
| 68 | N-[2-(indol-2-yl)phenyl]-amino | 16.4 mg/(96%) | 682 (M⁺) |
| 69 | N-[2-(5-nitropyridin-2-yl-amino) ethyl]amino | 12.2 mg/(74%) | 657 (M⁺) |
| 70 | N-[piperidin-1-yl]amino | 10.1 mg/(70%) | 575 (M + 1) |
| 71 | N-[quinuclidin-2-yl]amino | 8.9 mg/(59%) | 601 (M⁺) |
| 72 | N-[1-benzylpiperidin-4-yl]amino | 8.9 mg/(53%) | 665 (M⁺) |
| 73 | 4-hydroxypiperidin-1-yl | 8.4 mg/(58%) | 576 (M⁺) |
| 74 | 3,5-dimethylpiperidin-1-yl | 9.4 mg/(64%) | 588 (M⁺) |
| 75 | 4-(piperidin-1-yl)piperidin-1-yl | 6.5 mg/(40%) | 643 (M + 1) |
| 76 | 4-isopropylpiperazin-l-yl | 11.1 mg/(74%) | 603 (M + 1) |
| 77 | 4-(α-methylbenzyl)piperazin-1-yl | 12.1 mg/(73%) | 665 (M + 1) |
| 78 | 4-phenethylpiperazin-l-yl | 10.2 mg/(61%) | 665 (M + 1) |
| 79 | 4-[2-(N-isopropyl)-acetamido]piperazin-1-yl | 10.9 mg/(66%) | 660 (M + 1) |
| 80 | 4-methylhomopiperazin-1-yl | 5.8 mg/(39%) | 589 (M + 1) |

The amides of Examples 81–156 were prepared by the procedure described above beginning with 2(S)-[isobutyl]-2-[3(S)-4(S)-phenyloxazolidin-2-on-3-yl)-4(R)-(2-styryl)azetidin-2-on-1-yl]acetic acid (Example 22).

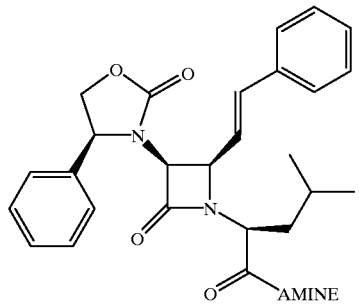

| Example | Amine Radical | Yield (% Yield) | MS (m/e) |
|---|---|---|---|
| 81 | N-[octyl]amino | 15.4 mg/(55%) | 560 (M + 1) |
| 82 | N-[3-(methyl)butyl]amino | 22.0 mg/(85%) | |
| 83 | N-[1-(ethyl)hexyl]amino | 14.2 mg/(51%) | 560 (M + 1) |
| 84 | N,N-[dibutyl]amino | 21.6 mg/(69%) | 628 (M + 1) |
| 85 | N-[3-(isopropoxy)propyl]-amino | 13.2 mg/(48%) | 548 (M + 1) |
| 86 | N-[2-(dimethylamino)ethyl]-amino | 18.7 mg/(72%) | 519 (M⁺) |
| 87 | N-[3-(dimethylamino)propyl]-amino | 14.9 mg/(56%) | 533 (M⁺) |
| 88 | N-[3-(diethylamino)propyl]-amino | 12.2 mg/(86%) | 561 (M + 1) |
| 89 | N-[4-(diethylamino)butyl]-amino | 8.4 mg/(59%) | 575 (M + 1) |
| 90 | N-[2,2-dimethyl-3-(dimethyl-amino)propyl]amino | 19.6 mg/(70%) | 561 (M⁺) |
| 91 | N-[2-(phenylamino)ethyl]-amino | 19.6 mg/(69%) | 567 (M + 1) |
| 92 | N-[2-pyrrolidin-1-yl)ethyl]-amino | 17.5 mg/(64%) | 546 (M + 1) |
| 93 | N-[3-(pyrrolidin-1-yl)-propyl]-amino | 12.8 mg/(92%) | 559 (M + 1) |
| 94 | N-[3-(pyrrolidin-2-yl)-propyl]-amino | 12.0 mg/(86%) | 559 (M + 1) |
| 95 | N-[3-(2-methylpiperidin-1-yl)propyl]amino | 11.6 mg/(68%) | 587 (M + 1) |
| 96 | N-[3-(1-morpholino)propyl]-amino | 14.6 mg/(100%) | 575 (M + 1) |
| 97 | N-[3-(4-methylpiperazin-1-yl)propyl]amino | 16.2 mg/(55%) | 588 (M + 1) |
| 98 | N-[3-(4-(2-hydroxyethyl)-piperazin-1-yl) propyl]amino | 16.8 mg/(100%) | |
| 99 | N-[2-(phenyl)ethyl]amino | 22.3 mg/(81%) | 552 (M⁺) |
| 100 | N-[3-(phenyl)propyl]amino | 8.6 mg/(30%) | 566 (M + 1) |
| 101 | N-[4-(phenyl)butyl]amino | 11.4 mg/(39%) | 580 (M + 1) |
| 102 | N-[α-methylbenzyl]amino | 25.0 mg/(91%) | 551 (M⁺) |
| 103 | N-[2-(phenyl)propyl]amino | 11.4 mg/(40%) | 566 (M + 1) |
| 104 | N-[diphenylmethyl]amino | 21.2 mg/(69%) | 614 (M + 1) |
| 105 | N-[2,2-(diphenyl)ethyl]amino | 18.2 mg/(58%) | 628 (M + 1) |
| 106 | N-[1,2-(diphenyl)ethyl]amino | 15.6 mg/(50%) | 628 (M + 1) |
| 107 | N-[3,3-(diphenyl)propyl]-amino | 11.6 mg/(36%) | 642 (M + 1) |
| 108 | N-[2-chlorobenzyl]amino | 10.4 mg/(36%) | 572 (M + 1) |
| 109 | N-[3-chlorobenzyl]amino | 20.8 mg/(73%) | 572 (M + 1) |
| 110 | N-[4-chlorobenzyl]amino | 24.6 mg/(86%) | 572 (M + 1) |
| 111 | N-[4-fluorobenzyl]amino | 19.7 mg/(71%) | 555 (M⁺) |
| 112 | N-[3-methylbenzyl]amino | 14.4 mg/(100%) | 552 (M + 1) |
| 113 | N-[3-trifluoromethylbenzyl]-amino | 19.8 mg/(100%) | 606 (M + 1) |
| 114 | N-[4-trifluoromethylbenzyl]-amino | 25.1 mg/(83%) | 606 (M + 1) |
| 115 | N-[4-aminobenzyl]amino | 7.8 mg/(28%) | 553 (M + 1) |
| 116 | N-[3,4-dichlorobenzyl]amino | 16.2 mg/(53%) | 606 (M⁺) |
| 117 | N-[3,4-difluorobenzyl]amino | 17.8 mg/(100%) | 574 (M + 1) |
| 118 | N-[2,4-dichlorobenzyl]amino | 13.6 mg/(45%) | 606 (M⁺) |
| 119 | N-[2,3-dimethoxybenzyl]amino | 18.4 mg/(61%) | 598 (M + 1) |
| 120 | N-[2-(4-hydroxyphenyl)-ethyl]amino | 10.4 mg/(37%) | 568 (M + 1) |

-continued

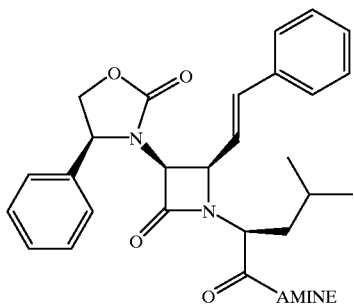

| Example | Amine Radical | Yield (% Yield) | MS (m/e) |
|---|---|---|---|
| 121 | N-[2-(4-methylphenyl)ethyl]-amino | 11.4 mg/(40%) | 566 (M + 1) |
| 122 | N-[2-(4-sulfonamidophenyl)-ethyl]amino | 16.1 mg/(51%) | 631 (M + 1) |
| 123 | N-[methyl]-N-[benzyl]amino | 17.0 mg/(61%) | 552 (M + 1) |
| 124 | N-[hydroxy]-N-[benzyl]amino | 22.4 mg/(81%) | 554 (M + 2) |
| 125 | N-[cyclohexylmethyl]amino | 10.2 mg/(38%) | 544 (M + 1) |
| 126 | N-[1-naphthylmethyl]amino | 21.0 mg/(71%) | 588 (M + 1) |
| 127 | N-[3,4-methylenedioxy-benzyl]-amino | 23.0 mg/(79%) | 582 (M + 1) |
| 128 | N-[2-furylmethyl]amino | 22.4 mg/(85%) | 528 (M+) |
| 129 | N-[2-tetrahydrofurylmethyl]-amino | 18.9 mg/(71%) | 532 (M+) |
| 130 | N-[(pyridin-3-yl)methyl]-amino | 25.6 mg/(95%) | 539 (M + 1) |
| 131 | N-[(pyridin-4-yl)methyl]-amino | 22.9 mg/(85%) | 539 (M + 1) |
| 132 | N-[2-(pyridin-2-yl)ethyl]-amino | 19.3 mg/(70%) | 553 (M+) |
| 133 | N-[2-(1-methylpyrrol-2-yl)ethyl]amino | 23.3 mg/(84%) | 555 (M+) |
| 134 | N-[3-(imidazol-4-yl)propyl]-amino | 19.1 mg/(69%) | 555 (M+) |
| 135 | N-[2-(indol-2-yl)ethyl]amino | 6.4 mg/(21%) | 590 (M + 1) |
| 136 | N-[phenyl]amino | 13.8 mg/(53%) | 524 (M+) |
| 137 | N-[4-hydroxyphenyl)amino | 9.0 mg/(32%) | 554 (M + 1) |
| 138 | N-[4-methoxyphenyl]amino | 11.2 mg/(39%) | 568 (M + 1) |
| 139 | N-[1-benzylpyrrolidin-3-yl)amino | 20.4 mg/(67%) | 607 (M + 1) |
| 140 | N-[4-benzylcyclohexyl]amino | 11.2 mg/(36%) | 621 (M + 1) |
| 141 | N-[indan-1-yl}amino | 23.9 mg/(85%) | 564 (M + 1) |
| 142 | N-[indan-2-yl]amino | 18.4 mg/(65%) | 564 (M+) |
| 143 | N-[1,2,3,4-tetrahydronaphth-5-yl]amino | 15.6 mg/(54%) | 578 (M + 1) |
| 144 | N-[fluoren-9-yl]amino | 17.2 mg/(56%) | 612 (M+) |
| 145 | 4-cyclohexylpiperidin-1-yl | 15.2 mg/(51%) | 599 (M + 1) |
| 146 | 4-benzylpiperidin-1-yl | 19.7 mg/(65%) | 606 (M+) |
| 147 | 4-(pyrrolidin-1-yl)piperidin-1-yl | 5.0 mg/(17%) | 585 (M + 1) |
| 148 | 2-(pyrrolidin-1-ylmethyl)-pyrrolidin-1-yl | 7.8 mg/(27%) | 585 (M + 1) |
| 149 | 4-(piperidin-1-yl)piperidin-1-yl | 24.0 mg/(80%) | 599 (M + 1) |
| 150 | 4-methylpiperazin-1-yl | 10.2 mg/(38%) | 531 (M + 1) |
| 151 | 4-benzylpiperazin-1-yl | 23.7 mg/(78%) | 607 (M+) |
| 152 | 4-phenylpiperazin-1-yl | 20.1 mg/(68%) | 593 (M + 1) |
| 153 | 4-(1-phenyl-1-propen-3-yl)piperazin-1-yl | 20.2 mg/(64%) | 633 (M + 1) |
| 154 | 4-(tert-butoxycarbonyl)piperazin-1-yl | 26.8 mg/(87%) | 617 (M+) |
| 155 | 4-methylhoinopiperazin-1-yl | 10.2 mg/(37%) | 545 (M + 1) |
| 156 | 1,2,3,4-tetrahydroisoquinolin-2-yl | 21.7 mg/(77%) | 564 (M + 1) |

EXAMPLE 157

Benzyl 2(S)-benzyl-2-[3(S)-(4(S)-phenyloxazolidin-2-on-3-yl)-4(R)-(2-styryl)azetidin-2-on-1-yl]acetate Beginning with 8.21 gm (32.2 mMol) (L)-phenylalanine benzyl ester, 10.75 gm (58%) of the title compound was recovered as off-white crystals from n-chlorobutane following the procedure described in detail in Example 1.

m.p.=141–143° C.; MS(FD):m/e=572 (M+).

EXAMPLE 158 tert-Butyl 2(S)-sec-butyl-2-[3(S)-(4(S)-phenyloxazolidin-2-on-3-yl)-4(R)-(2-styryl)azetidin-2-on-1-yl]acetate Beginning with 3.0 gm (16.0 mMol) (L)-isoleucine tert-butyl ester, 3.2 gm (40%) of the title compound was recovered as colorless crystals from n-chlorobutane following the procedure described in detail in Example 1.

m.p.=172–174° C.; MS(FD): m/e=504 (M+).

EXAMPLE 159

Benzyl 2(S)-tert-butyl-2-[3(S)-(4(S)-phenyloxazolidin-2-on-3-yl)-4(R)-(2-styryl)azetidin-2-on-1-yl]acetate Deprotection of Ester To a solution of 1.0 gm (2.0 mMol) tert-butyl 2(S)-sec-butyl-2-[3(S)-(4(S)-phenyloxazolidin-2-on-3-yl)-4(R)-(2-styryl)azetidin-2-on-1-yl]acetate (Example 158) in 10 mL dichloromethane was added 1.0 mL trifluoroacetic acid. The reaction mixture was stirred for 18 hours at room temperature and was then concentrated under reduced pressure. The residue was crystallized from n-chlorobutane to provide 2(S)-sec-butyl-2-[3(S)-(4(S)-phenyloxazolidin-2-on-3-yl)-4(R)-(2-styryl)azetidin-2-on-1-yl]acetic acid as a colorless solid which was used directly in the subsequent step.

Esterification

To a solution of 0.146 gm (0.325 mMol) 2(S)-sec-butyl-2-[3(S)-(4(S)-phenyloxazolidin-2-on-3-yl)-4(R)-(2-styryl) azetidin-2-on-1-yl]acetic acid in 2 mL dichloromethane were added 30 μL oxalyl chloride followed by 1 drop of dimethylformamide. The reaction mixture was stirred for 20 minutes at room temperature and was then concentrated under reduced pressure. The residue was redissolved in 2 mL dichloromethane and to this solution was added 1.4 equivalents of benzyl alcohol. The reaction mixture was stirred for 18 hours at room temperature. The reaction mixture was concentrated under reduced pressure and the residue subjected to radial chromatography. Fractions shown to contain product were combined and concentrated under reduced pressure to provide the title compound as a colorless solid.

m.p.=176–178° C.; MS(FD): m/e 538 (M+).

EXAMPLE 160 tert-Butyl 2(R,S)-(2,2,2-trichloroethoxycarbonyl)-2-[3(S)-(4(S)-phenyloxazolidin-2-on-3-yl)-4(R)-(2-styryl)azetidin-2-on-1-yl]acetate Beginning with 9.0 gm (20 mMol) tert-butyl 2-[3(S)-(4(S)-phenyloxazolidin-2-on-3-yl)-4(R)-(2-styryl)azetidin-2-on-1-yl]acetate (Example 2) and 4.24 gm (20 mMol) trichloroethylchloroformate, 7.0 gm (56%) of the title compound was recovered by the procedure described in detail in Example 41.

m.p.=176–178° C.; MS(FD): m/e=611 (M+).

EXAMPLE 161 tert-Butyl 2(R,S)-carboxy-2-[3(S)-(4(S)-phenyloxazolidin-2-on-3-yl)-4(R)-(2-styryl)azetidin-2-on-1-yl]acetate A solution of 0.53 gm (0.85 mMol) tert-butyl 2(R,S)-(2,2-trichloroethoxycarbonyl)-2-[3(S)-(4(S)-phenyloxazolidin-2-on-3-yl)-4(R)-(2-styryl)azetidin-2-on-1-yl]acetate (Example 160) in 20 mL dimethylformamide was cooled to 0° C. To this solution was added 2.0 mL 5N hydrochloric acid followed by 0.33 gm zinc dust. The reaction mixture was stirred at 0° C. for 90 minutes and was then allowed to warm to room temperature over 30 minutes. The reaction mixture was filtered and the filtrate was concentrated under reduced pressure at room temperature over night. The resulting residue was partitioned between ethyl acetate and water. The phases were separated and the organic phase was washed several times with water. The remaining organic phase was dried over sodium sulfate and concentrated under reduced pressure to provide 0.40 gm (96%) of the title compound as a crystalline solid.

m.p.=179–180° C.

EXAMPLE 162 tert-Butyl 2(R,S)-[N-(3-trifluoromethylbenzyl)carboxamido]-2-[3(S)-(4(S)-phenyloxazolidin-2-on-3-yl)-4(R)-(2-styryl)azetidin-2-on-1-yl]acetate To a slurry of 0.56 gm (1.14 mMol) tert-butyl 2(R,S)-carboxy-2-[3(S)-(4(S)-phenyloxazolidin-2-on-3-yl)-4(R)-(2-styryl)azetidin-2-on-1-yl]acetate (Example 161) in 50 mL dichloromethane were added 1.25 equivalents of oxalyl chloride followed by 1 drop of dimethylformamide. Vigorous gas evolution occurs and the reaction becomes homogeneous after 10 minutes. An additional drop of dimethylformamide was added and the reaction stirred an additional 10 minutes at room temperature. The reaction mixture was concentrated under reduced pressure and the resulting residue redissolved in 50 mL dichloromethane. To the reaction mixture was then added dropwise a solution of 1.1 equivalents 3-trifluoromethylbenzylamine and 1.1 equivalents triethylamine in 2 mL dichloromethane. Once the addition was complete, the reaction mixture was stirred one hour at room temperature. The reaction mixture was then washed with water and concentrated under reduced pressure. The residue was crystallized from n-chlorobutane containing a small amount of acetonitrile to provide 0.39 gm (53%) of the title compound as and off-white solid.

m.p.=182–184° C.; MS(FD): m/e=649 (M$^+$).

EXAMPLE 163

Resolution of 2-(Trimethylsilyl)ethyl 2(R,S)-[(1,1-ethyleneketal)propionyl]-2-[3(S)-(4(S)-phenyloxazolidin-2-on-3-yl)-4(R)-(2-styryl)azetidin-2-on-1-yl]acetate A. 2-(Trimethylsilyl)ethyl 2(R)-[(1,1-ethyleneketal)propionyl]-2-[3(S)-(4(S)-(4-(S)-phenyloxazolidin-2-on-3-yl)-4(R)-(2-styryl)azetidin-2-on-1-yl]acetate 2-(Trimethylsilyl)ethyl 2(R,S)-[(1,1-ethyleneketal)propionyl]-2-[3(S)-(4(S)-phenyloxazolidin-2-on-3-yl)-4(R)-(2-styryl)azetidin-2-on-1-yl]acetate, prepared as described in Example 13, was recovered as a thick slurry. Subjecting a sample of the slurry to silica gel thin layer chromatography (1:1 hexane:ethyl acetate) demonstrated that the slurry comprised two major components. The slurry was filtered and the solid subjected to flash silica gel chromatography, eluting with ethyl acetate. Fractions containing product were combined and concentrated under reduced pressure to provide 28 gm 2-(trimethylsilyl)ethyl 2(R)-((1,1-ethyleneketal)propionyl]-2-[3(S)-(4(S)-phenyloxazolidin-2-on-3-yl)-4(R)-(2-styryl)azetidin-2-on-1-yl]acetate as a fluffy solid. This solid represented the faster moving component by silica gel thin layer chromatography analysis.

MS(FD): m/e=592 (M$^+$).

A portion of this solid was recrystallized from ethyl acetate/hexane and the resultant crystals were analyzed by X-ray crystallography to determine the absolute configuration at the 2-carbon of the acetate moiety. The absolute configuration at this carbon was demonstrated to be "R".

B. 2-(Trimethylsilyl)ethyl 2(S)-[(1,1-ethyleneketal)propionyl]-2-[3(S)-(4(S)-phenyloxazolidin-2-on-3-yl)-4(R)-(2-styryl)azetidin-2-on-1-yl]acetate The filtrate resulting from the filtration of the original slurry in section A was concentrated under reduced pressure. The residue, which was substantially comprised of the slower eluting component of the original slurry, was subjected to silica gel chromatography, eluting with a gradient of hexane containing from 0 to 100% ethyl acetate. Fractions containing product were combined and concentrated under reduced pressure to provide a syrup. The residue became a slurry upon standing and the solid component of the slurry was collected by filtration to provide 40.0 gm 2-(trimethylsilyl)ethyl 2(S)-[(1,1-ethyleneketal)propionyl]-2-[3(S)-(4(S)-phenyloxazolidin-2-on-3-yl)-4(R)-(2-styryl)azetidin-2-on-1-yl]acetate.

MS(FD): m/e=592 (M$^+$).

EXAMPLE 164

2(R)-[(1,1-ethyleneketal)propionyl]-2-[3(S)-(4(S)-phenyloxazolidin-2-on-3-yl)-4(R)-(2-styryl)azetidin-2-on-1-yl]acetic acid A mixture of 12.6 gm (21.3 mMol) 2-(trimethylsilyl)ethyl 2(R)-[(1,1-ethyleneketal)propionyl]-2-[3(S)-(4(S)-phenyloxazolidin-2-on-3-yl)-4(R)-(2-styryl)azetidin-2-on-1-yl]acetate (Example 163A) and 63.8 mL (63.8 mMol) tetrabutylammonium fluoride (1M in tetrahydrofuran) in 42 mL dimethylformamide was stirred at room temperature for 15 minutes under a nitrogen atmosphere. The reaction mixture was diluted with 300 mL ethyl acetate and the resulting mixture stirred vigorously as the pH was adjusted to 1.8 by the gradual addition of 1N hydrochloric acid. The phases were separated and the aqueous phase was washed with several 125 mL aliquots of water. The remaining suspension was concentrated under reduced pressure to provide a crystalline mass. The mass was recrystallized from n-butyl chloride and acetonitrile to provide 9 gm (86%) of the title compound as a crystalline solid.

MS(FD): m/e=492 (M$^+$).

EXAMPLE 165

2(S)-[(1,1-ethyleneketal)propionyl]-2-[3(S)-(4(S)-phenyloxazolidin-2-on-3-yl)-4(R)-(2-styryl)azetidin-2-on-1-yl]acetic acid Beginning with 24 gm (40.5 mMol) 2-(trimethylsilyl)ethyl 2(S)-[(1,1-ethyleneketal)propionyl]-2-[3(S)-(4(S)- phenyloxazolidin-2-on-3-yl)-4(R)-(2-styryl)azetidin-2-on-1-yl]acetate (Example 163B), 10.0 gm (50%) of the title compound were recovered as a crystalline solid.

MS(FD): m/e=493 (M+1).

EXAMPLE 166

1-[2(R)-[(1,1-ethyleneketal)propionyl]-2-[3(S)-(4(S)-phenyloxazolidin-2-on-3-yl)-4(R)-(2-styryl)azetidin-2-on-1-yl]acetyl]-4-[2-phenyleth-1-yl]piperazine A mixture of 1.5 gm (3 mMol) 2(R)-[(1,1-ethyleneketal)-propionyl]-2-[3(S)-(4(S)-phenyloxazolidin-2-on-3-yl)-4(R)-(2-styryl)azetidin-2-on-1-yl]acetic acid (Example 164), 0.285 gm (1.5 mMol) 1-(2-phenyleth-1-yl)piperazine, and 6 gm (6 mMol) divinylbenzene crosslinked polystyrene supported 1-(3-dimethylaminopropyl)-3-ethylcarbodiimide in 100 mL chloroform was stirred at room temperature for 18 hours. The reaction mixture was filtered and the filtrate concentrated under reduced pressure. The residue was subjected to silica gel chromatography, eluting with a gradient of chloroform containing 0 to 5% methanol. Fractions containing product were combined and concentrated under reduced pressure to provide 0.59 gm (60%) of the title compound as a foam.

MS(FD): m/e=664 (M$^+$).

EXAMPLE 167

1-[2(S)-[(1,1-ethyleneketal)propionyl]-2-[3(S)-(4(S)-phenyloxazolidin-2-on-3-yl)-4(R)-(2-styryl)azetidin-2-on-1-yl]acetyl]-4-[2-phenyleth-1-yl]piperazine Beginning with 1.5 gm (3 mMol) 2(S)-[(1,1-ethyleneketal)propionyl]-2-[3(S)-(4(S)-phenyloxazolidin-2-on-3-yl)-4(R)-(2-styryl)azetidin-2-on-1-yl]acetic acid (Example 165), 0.95 gm (95%) of the title compound was recovered as a foam by the procedure described in Example 166.

MS(FD): m/e=664 (M$^+$).

The human vasopressin $V_{1a}$ receptor has been cloned and expressed (Thibonnier et al., *Journal of Biological Chemistry*, 269, 3304–3310 (1994)). The nucleotide sequence has been deposited in the EMBL Databank under accession number Z11690. To demonstrate the affinity of the compounds of the present invention for the human vasopressin $V_{1a}$ receptor, binding studies were performed using a cell line expressing the human $V_{1a}$ receptor in Chinese hamster ovary (CHO) cells (henceforth referred to as the h$V_{1a}$ cell line) substantially by the procedure described by Thibonnier (*Journal of Biological Chemistry*, 269, 3304–3310 (1994)).

The h$V_{1a}$ cell line was grown in alpha-MEM (alpha modification of Minimum essential medium Eagle, Sigma, St. Louis, Mo., USA) with 10% fetal bovine serum and 250 μg/ml G418 (Gibco, Grand Island, N.Y., USA). To prepare membranes, h$V_{1a}$ cells were grown to confluency in 20 roller bottles. Cells were dissociated with enzyme-free cell dissociation medium (Specialty Media, Lavallette, N.J., USA) and centrifuged at 2500 rpm for 10 minutes. The pellet was resuspended in 40 mL of Tris-HCl (tris[hydroxymethyl]aminomethane hydrochloride) buffer (50 mM, pH 7.4) and homogenized for 1 minute with a Tekmar Tissumizer (Cincinnatti, Ohio USA). The suspension was centrifuged at 40,000×g for 10 minutes. The pellet was resuspended and centrifuged as above. The final pellet was suspended in 80 mL of Tris 7.4 buffer and stored in 4 mL aliquots at −80° C.

For assay, aliquots were resuspended in assay buffer and diluted to 125 μg protein per mL. Protein concentration was determined by BCA assay (Pierce, Rockford, Ill., USA).

Assay buffer was prepared by adjusting the pH of a solution of 50 mMol HEPES (N-2-Hydroxyethylpiperazine-N'-2-ethanesulfonic acid, Sigma, St. Louis, Mo., USA), 5 mMol MgCl$_2$, and 1 mMol dithiothreitol pH 7.4 with NaOH, after which 40 μg/mL bacitracin and 10 μg/mL aprotinin were added. The radioligand for binding assays was [$^3$H] PMP-AVP (Manning vasopressin antagonist, 56 Ci/mMol, DuPont NEN, Boston, Mass., USA). The order of additions was 195 μL assay buffer, 200 μL h$V_{1a}$ membranes (25 μg protein) in assay buffer, 5 μL of test agent in dimethylsulfoxide (DMSO) or DMSO alone, and 100 μL [$^3$H]PMP-AVP in assay buffer (final concentration 0.2 nM). Incubations were for one hour at room temperature. Bound radioligand was separated from free by filtration on a Brandel cell harvester (Gaithersburg, Md., USA) through Whatman GF/B glass-fiber filters that had been soaked for 2 hours in Tris-HCl pH 7.7 containing 200 μg/mL bovine serum albumin and 0.2% polyethylenimine. The filters were washed with ice-cold 50 mM Tris-HCl (pH 7.7 at 25° C.) and the filter circles were placed in scintillation vials, to which were then added 5 mL Ready Protein Plus scintillation fluid, and counted in a liquid scintillation counter. All incubations were in triplicate, and dose-inhibition curves consisted of total binding, nonspecific binding (100 mM PMP-AVP, Peninsula Labs, Belmont, Calif., USA), and 6 or 7 concentrations of test agent encompassing the IC$_{50}$. Total binding was typically about 2,000 cpm and nonspecific binding about 250 cpm. IC$_{50}$ values were calculated by nonlinear least-squares curve-fitting to a 4-parameter logistic model.

All of the esters and amides exemplified were tested in this assay and were found to exhibit an affinity at the vasopressin $V_{1a}$ receptor of at least 100 μM. Binding affinities for certain of the preferred compounds are summarized in the following table.

| EXAMPLE | BINDING AFFINITY (IC$_{50}$ (nM)) |
| --- | --- |
| 7 | 39 |
| 27 | 28 |
| 30 | 43 |
| 31 | 23 |
| 34 | 78 |
| 38 | 10 |
| 39 | 13 |
| 40 | 40 |
| 42 | 5 |
| 46 | 11 |
| 50 | 64 |
| 54A | 2 |
| 54B | 9 |
| 64 | (98%)* |
| 65 | (98%)* |
| 67 | 5 |
| 69 | (96%)* |
| 71 | (92%)* |
| 73 | (86%)* |
| 78 | 16 |
| 80 | (96%)* |
| 97 | 42 |
| 109 | 40 |
| 112 | 25 |
| 113 | 41 |

*% displacement at 10 μM

The physiological effects of vasopressin are mediated through specified G-protein coupled receptors. The vasopressin $V_{1a}$ receptor is coupled to the $G_q/G_{11}$ family of G proteins and mediates phosphatidylinositol turnover. The agonist or antagonist character of the compounds of the invention may be determined by their ability to inhibit vasopressing mediated turnover of phosphatidylinositol by the procedure described in the following paragraphs. A representative compound of the invention, the compound of Example 70, was tested in this assay and found to be a vasopressing $V_{1a}$ antagonist.

Cell Culture and Labeling of Cells.

Clone 9 rat hepatoma cells (American Type Culture Collection, Rockville, Md., U.S.A.; ATCC CRL-1439, Permanent Collection; *Cancer Research*, 35, 253–263 (1975)) were grown in F-12K (Gibco) with 10% fetal bovine serum. Three days prior to the assay, near-confluent cultures were dissociated and seeded in 6-well tissue culture plates, about 100 wells being seeded from each 75 cm$^2$ flask (equivalent to 12:1 split ratio). Each well contained 1 mL of growth medium with 2 $\mu$Ci of [$^3$H]myo-inositol (American Radiolabeled Chemicals, St. Louis, Mo., USA).

Incubations

All assays were in triplicate except for basal and 10 nM AVP (both n=6). AVP ((arginine vasopressin), Peninsula Labs, Belmont, Calif., USA (#8103)) was dissolved in 0.1N acetic acid. Test agents were dissolved in DMSO and diluted in DMSO to 200 times the final test concentration. Test agents and AVP (or corresponding volumes of DMSO) were added separately as 5 $\mu$L in DMSO to 12×75 mm glass tubes containing 1 mL of assay buffer (Tyrode's balanced salt solution containing 50 mM glucose, 10 mM LiCl, 15 mM HEPES pH 7.4, 10 $\mu$M phosphoramidon, and 100 $\mu$M bacitracin). The order of incubations was randomized. Incubations were initiated by removing the prelabeling medium, washing the monolayer once with 1 mL of 0.9% NaCl, and adding the contents of the assay tubes. The plates were incubated for 1 hour at 37° C. Incubations were terminated by removing the incubation medium and adding 500 $\mu$L of ice cold 5% (w/v) trichloroacetic acid and allowing the wells to stand for 15 min.

Measurement of [$^3$H]Inositol Phosphates

BioRad Poly-Prep Econo-Columns were packed with 0.3 mL of AG 1 X-8 100–200 formate form resin. Resin was mixed 1:1 with water and 0.6 mL added to each column. Columns were then washed with 10 mL water. Scintillation vials (20 mL) were placed under each column. For each well, the contents were transferred to a minicolumn, after which the well was washed with 0.5 mL distilled water, which was also added to the minicolumn. The columns were then washed twice with 5 mL of 5 mM myo-inositol to elute free inositol. Aliquots (1 mL) were transferred to 20 mL scintillation vials and 10 mL of Beckman Ready Protein Plus added. After the myo-inositol wash was complete, empty scintillation vials were placed under the columns, and [$^3$H] inositol phosphates were eluted with three additions of 1 mL 0.5 M ammonium formate containing 0.1 N formic acid. Elution conditions were optimized to recover inositol mono-, bis-, and trisphosphates, without eluting the more metabolically inert tetrakis-, pentakis-, and hexakis-phosphates. To each sample was added 10 mL of a high salt capacity scintillation fluid such as Tru-Count High Salt Capacity or Packard Hionic-Fluor. Inositol lipids were measured by adding 1 mL of 2% sodium dodecyl sulfate (SDS) to each well, allowing the wells to stand for at least 30 min., and transferring the solution to 20 mL scintillation vials, to which 10 mL Beckman Ready Protein Plus scintillation fluid was then added. Samples were counted in a Beckman LS 3801 liquid scintillation counter for 10 min. Total inositol incorporation for each well was calculated as the sum of free inositol, inositol phosphates, and inositol lipids. Inositol phosphates were expressed as dpm per 10$^6$ dpm of total inositol incorporation.

Data Analysis—Concentration-inhibition Experiments

Concentration-response curves for AVP and concentration-inhibition curves for test agents versus 10 nM AVP were analyzed by nonlinear least-squares curve-fitting to a 4-parameter logistic function. Parameters for basal and maximal inositol phosphates, EC$_{50}$ or IC$_{50}$, and Hill coefficient were varied to achieve the best fit. The curve-fitting was weighted under the assumption that the standard deviation was proportional to dpm of radioactivity. Full concentration-response curves for AVP were run in each experiment, and IC$_{50}$ values were converted to K$_i$ values by application of the Cheng-Prusoff equation, based on the EC$_{50}$ for AVP in the same experiment.

Data Analysis—Competitivity Experiments

Experiments to test for competitivity of test agents consisted of concentration-response curves for AVP in the absence and presence of two or more concentrations of test agent. Data were fit to a competitive logistic equation $$Y = B + \frac{M \cdot \{A/[E+(D/K)]\}^Q}{1+\{A/[E+(D/K)]\}^Q}$$

where Y is dpm of inositol phosphates, B is concentration of basal inositol phosphates, M is the maximal increase in concentration of inositol phosphates, A is the concentration of agonist (AVP), E is the EC50 for agonist, D is the concentration of antagonist (test agent), K is the K$_i$ for antagonist, and Q is the cooperativity (Hill coefficient).

Vasopressin $V_{1a}$ receptors are also known to mediate platelet aggregation. Vasopressin $V_{1a}$ receptor agonists cause platelet aggregation, while vasopressin $V_{1a}$ receptor antagonists inhibit the platelet aggregation precipitated by vasopressin or vasopressin $V_{1a}$ agonists. The degree of antagonist activity of the compounds of the invention may be determined by the assay described in the following paragraphs.

Blood from healthy, human volunteers was collected by venipuncture and mixed with heparin (60 mL of blood added to 0.4 mL of heparanized saline solution (4 mg heparin/mL saline)). Platelet-rich plasma (PRP) was prepared by centrifuging whole blood (150×g), and indomethacin (3 $\mu$M) was added to PRP to block the thromboxane-mediated release reaction. PRP was continuously stirred at 37° C. and change in optical density was followed after the addition of arginine vasopressin (AVP) (30 mM) to initiate aggregation. Compounds were dissolved in 50% dimethylsulfoxide (DMSO) and added (10 $\mu$L/415 $\mu$L PRP) before the addition of AVP. The percent inhibition of AVP-induced aggregation was measured and an IC$_{50}$ calculated. The compound of Example 30 was tested in this assay and found to be an antagonist of the vasopressin $V_{1a}$ receptor with an IC$_{50}$ of 630 nM.

In studies using washed platelets, 50 mL of whole blood was mixed with 10 mL of citrate/heparin solution (85 mM sodium citrate, 64 mM citric acid, 111 mM glucose, 5 units/mL heparin) and PRP isolated as described above. PRP was then centrifuged (150×g) and the pellet resuspended in a physiologic buffer solution (10 mM HEPES, 135 mM sodium chloride, 5 mM potassium chloride, and 1 mM magnesium chloride) containing 10 $\mu$M indomethicin. Human fibrinogen (0.2 mg/mL) and calcium chloride (1 mM) were added to stirred platelets before initiating aggregation with AVP (30 nM) as previously described. The compounds of Examples 30 and 42 were tested in this assay and found to be antagonists of the vasopressin $V_{1a}$ receptor with $IC_{50}$ values of 48 and 28 nM, respectively.

The activity of compounds of Formula I in the antagonism of the vasopressin $V_{1a}$ receptor provides a method of antagonizing the vasopressin $V_{1a}$ receptor comprising administering to a subject in need of such treatment an effective amount of a compound of that formula. It is known that numerous physiological and therapeutic benefits are obtained through the administration of drugs which antagonize the vasopressin $V_{1a}$ receptor. These activities may be categorized as peripheral and central. Peripheral utilities include administration of vasopressin $V_{1a}$ antagonists of Formula I as adjuncts in heart failure or as antithrombotic agents. Central effects include administration of vasopressin $V_{1a}$ antagonists of Formula I in the treatment of obsessive-compulsive disorder, aggressive disorders, depression and anxiety.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted subject may be unable to do anything but carry out the rituals required by the disease. Obsessive-compulsive disease, in all its variations, is a preferred target of treatment with the present adjunctive therapy method and compositions. The utility of the compounds of Formula I in the treatment of obsessive-compulsive disorder was demonstrated as described in the following assay.

In golden hamsters, a particular stereotypy, flank marking behavior, can be induced by micro-injections of vasopressin (10–100 nL, 1–100 μM) into the anterior hypothalamus (Ferris, et al., *Science*, 224, 521–523 (1984); Albers and Ferris, *Regulatory Peptides*, 12, 257–260 (1985); Ferris et al., *European Journal of Pharmacology*, 154, 153–159 (1988)). Following the releasing stimulus, the behavior is initiated by grooming, licking and combing of the large sebaceous glands on the dorsolateral flanks. Bouts of flank gland grooming may be so intense that the flank region is left matted and soaked in saliva. After grooming, the hamsters display flank marking behavior, a type of scent marking involved in olfactory communication (Johnston, *Physio. Behav.*, 51, 437–448 (1985); Ferris, et al., *Physio. Behav.*, 40, 661–664 (1987)), by arching the back and rubbing the flank glands vigorously against any vertical surface. Vasopressin-induced flank marking is usually induced within a minute after the micro-injection (Ferris, et al., *Science*, 224, 521–523 (1984)). The behavior is specific to vasopressin, as micro-injections of other neuropeptides, excitatory amino acids, and catecholamines do not elicit flank marking (Ferris, et al., *Science*, 224, 521–523 (1984); Albers and Ferris, *Regulatory Peptides*, 12, 257–260 (1985)). Furthermore, flank marking is specific to the vasopressin $V_1$ receptor, as the behavior is selectively inhibited by $V_1$ receptor antagonists and activated by $V_1$ receptor agonists (Ferris, et al., *Neuroscience Letters*, 55, 239–243 (1985); Albers, et al., *Journal of Neuroscience*, 6, 2085–2089 (1986); Ferris et al., *European Journal of Pharmacology*, 154, 153–159 (1988)).

All animals were adult male golden hamsters (*Mesocricetus auratus*) weighing approximately 160 gm. The animals underwent stereotaxic surgery, and were allowed to recover before behavioral testing. The hamsters were kept on a reverse light cycle (14 hr light, 10 hr dark, lights on at 19:00) in Plexiglas™ cages, and received food and water ad libitum.

Stereotaxic surgery was performed under pentobarbital anesthesia. The stereotaxic coordinates were: 1.1 mm anterior to the bregma, 1.8 mm lateral to the midsagittal suture at an 8° angle from the verticle line, and 4.5 mm below the dura. The nose bar was placed at the level of the interaural line. An unilateral 26-gauge guide cannula was lowered to the site and secured to the skull with dental cement. The guide cannulae was closed with a 33-gauge obturator extending 1 mm beyond the guide. The innercanulae used for the micro-injections extended 3.0 mm beyond the guide to reach the anterior hypothalamus.

The hamsters were microinjected with 1 μM vasopressin in a volume of 150 nL. The vasopressin was given as a cocktail with 200 mM, 20 mM, 2 mM of the test compound or alone, in the vehicle, dimethylsulfoxide. Both the vasopressin and the test compound were dissolved in 100% dimethylsulfoxide. All injections were aimed at the anterior hypothalamus. Animals were scored for flank marking for a period of 10 minutes in a clean cage. A representative compound, the compound of Example 42, inhibited vasopressin-induced flank marking in a dose dependent manner.

Another aspect of this invention is the use of compounds of Formula I in combination with a serotonin reuptake inhibitor for use in the treatment of obsessive-compulsive disease, aggressive disorder, or depression. Compounds useful as serotonin reuptake inhibitors include but are not limited to:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson et al., *J. Med. Chem.*, 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers;

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule;

Venlafaxine is known in the literature, and its method of synthesis and its activity as an inhibitor of serotonin and norepinephrine uptake are taught by U.S. Pat. No. 4,761,501. Venlafaxine is identified as compound A in that patent;

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret et al., *Neuropharmacology*, 24, 1211–19 (1985), describe its pharmacological activities as an inhibitor of serotonin and norepinephrine reuptake;

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen et al., *Eur. J. Pharmacol.*, 41, 153 (1977), and reports of its clinical effectiveness in depression may be found in Dufour et al., *Int. Clin. Psychopharmacol.*, 2, 225 (1987), and Timmerman et al., ibid., 239;

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen et al., *Brit. J. Pharmacol.*, 60, 505 (1977); and De Wilde et al., *J. Affective Disord.*, 4, 249 (1982); and Benfield et al., *Drugs*, 32, 313 (1986);

Paroxetine, trans-(−)-3-[(1,3-benzodioxol-5-yloxy) methyl]-4-(4-fluorophenyl)piperidine, may be found in U.S. Pat. Nos. 3,912,743 and 4,007,196. Reports of the drug's activity are in Lassen, *Eur. J. Pharmacol.*, 47, 351 (1978); Hassan et al., *Brit. J. Clin. Pharmacol.*, 19, 705 (1985); Laursen et al., *Acta Psychiat. Scand.*, 71, 249 (1985); and Battegay et al., *Neuropsychobiology*, 13, 31 (1985); and Sertraline, (1S-cis)-4-(3,4-dichlorophenyl)-1,2,3,4-tetrahydro-N-methyl-1-naphthylamine hydrochloride, is a serotonin reuptake inhibitor which is marketed as an antidepressant. It is disclosed by U.S. Pat. No. 4,536,518. All of the above-referenced patents are hereby incorporated by reference.

The adjunctive therapy of this aspect of the present invention is carried out by administering a vasopressin $V_{1a}$ antagonist together with a serotonin reuptake inhibitor in any manner which provides effective levels of the compounds in the body at the same time. All of the compounds concerned are orally available and are normally administered orally, and so oral administration of the adjunctive combination is preferred. They may be administered together, in a single dosage form, or may be administered separately.

This aspect of the present invention provides a potentiation of the decrease in the concentration of vasopressin observed as an effect of administration of a vasopressin $V_{1a}$ antagonist by administration of a serotonin reuptake inhibitor. This aspect of the present invention is particularly suited for use in the treatment of depression and obsessive compulsive disorder. Such disorders may often be resistant to treatment with a serotonin reuptake inhibitor alone.

OXYTOCIC ACTIVITY

Compounds of the present invention are believed to be oxytocin agents. Oxytocin preparations and a number of oxytocin agonists are commercially available for therapeutic use. In recent years, oxytocin antagonists with antiuterotonic activity have been developed and evaluated for their potential use in the treatment of preterm labor and dysmenorrhyea (Pavo, et al., *J. Med. Chem.*, 37, 255–259 (1994); Akerlund, et al., *Br. J. Obstet. Gynaecol.*, 94, 1040–1044 (1987); Akerlund, et al., *Br. J. Obstet. Gynaecol.*, 86, 484–487 (1979)). The oxytocin antagonist atosiban has been studied clinically and resulted in a more significant inhibition of preterm contractions than did placebo (Goodwin, et al., *Am. J. Obstet. Gynecol.*, 170, 474 (1994)).

The human oxytocin receptor has been cloned and expressed (Kimura et al., *Nature*, 356, 526–529 (1992)), it is identified under the accession number X64878. To demonstrate the affinity of the compounds of the present invention for the human oxytocin receptor, binding studies were performed using a cell line expressing the human oxytocin receptor in 293 cells (henceforth referred to as the OTR cell line) substantially by the procedure described by Morel et al. (*Nature*, 356, 523–526 (1992)). The 293 cell line is a permanent line of primary human embryonal kidney cells transformed by sheared human adenovirus type 5 DNA. It is identified as ATCC CRL-1533.

The OTR cell line was grown in DMEM (Delbecco's Modified Essential Medium, Sigma, St. Louis, Mo., USA) with 10% fetal bovine serum, 2 mM L-glutamine, 200 µg hygromycin (Sigma, St. Louis, Mo., USA) and 250 µg/ml G418 (Gibco, Grand Island, N.Y., USA). To prepare membranes, OTR cells were grown to confluency in 20 roller bottles. Cells were dissociated with enzyme-free cell dissociation medium (Specialty Media, Lavallette, N.J., USA) and centrifuged at 3200 rpm for 15 minutes. The pellet was resuspended in 40 mL of Tris-HCl (tris[hydroxymethyl] aminomethane hydrochloride) buffer (50 mM, pH 7.4) and homogenized for 1 minute with a Tekmar Tissumizer (Cincinnatti, Ohio USA). The suspension was centrifuged at 40,000×g for 10 minutes. The pellet was resuspended and centrifuged as above. The final pellet was suspended in 80 mL of Tris 7.4 buffer and stored in 4 mL aliquots at −80° C. For assay, aliquots were resuspended in assay buffer and diluted to 375 µg protein per mL. Protein concentration was determined by BCA assay (Pierce, Rockford, Ill., USA).

Assay buffer was 50 mM Tris-HCl (tris[hydroxymethyl]-aminomethane hydrochloride), 5 mM $MgCl_2$, and 0.1% bovine serum albumin at pH 7.4. The radioligand for binding assays was [$^3$H]oxytocin ([tyrosyl-2,6-$^3$H]oxytocin, 48.5 Ci/mMol, DuPont NEN, Boston, Mass., USA). The order of additions was 195 µL assay buffer, 200 µL OTR membranes (75 µg protein) in assay buffer, 5 µL of test agent in dimethylsulfoxide (DMSO) or DMSO alone, and 100 µL [$^3$H]oxytocin in assay buffer (final concentration 1.0 nM). Incubations were for one hour at room temperature. Bound radioligand was separated from free by filtration on a Brandel cell harvester (Gaithersburg, Md., USA) through Whatman GF/B glass-fiber filters that had been soaked for 2 hours in 0.3% polyethylenimine. The filters were washed with ice-cold 50 mM Tris-HCl (pH 7.7 at 25° C.) and the filter circles were placed in scintillation vials, to which were then added 5 mL Ready Protein Plus™ scintillation fluid, and counted in a liquid scintillation counter. All incubations were in triplicate, and dose-inhibition curves consisted of total binding, nonspecific binding (100 µM oxytocin, Sigma, St. Louis, Mo., USA), and 6 or 7 concentrations of test agent encompassing the $IC_{50}$. Total binding was typically about 1,000 cpm and nonspecific binding about 200 cpm. $IC_{50}$ values were calculated by nonlinear least-squares curve-fitting to a 4-parameter logistic model. Certain compounds of Formula I have shown affinity for the oxytocin receptor.

Several bioassays are available to determine the agonist or antagonist character of compounds exhibiting affinity at the oxytocin receptor. One such assay is described in U.S. Pat. No. 5,373,089, hereby incorporated by reference. Said bioassay is derived from procedures described in a paper by Sawyer, et al. (*Endocrinology*, 106, 81 (1980)), which in turn was based on a report of Holton (*Brit. J. Pharmacol.*, 3, 328 (1948)). The assay calculations for $pA_2$ estimates are described by Schild (*Brit. J. Pharmacol.*, 2, 189 (1947)).

Method

1. Animals-a 1.5 cm piece of uterus from a virgin rat (Holtzman) in natural estrus is used for the assay.

2. Buffer/Assay Bath-The buffer used is Munsicks. This buffer contains 0.5 mM $Mg^{++}$. The buffer is gassed continuously with 95% oxygen/5% carbon dioxide giving a pH of 7.4. The temperature of the assay bath is 37° C. A 10 mL assay bath is used that contains a water jacket for maintaining the temperature and inlet and outlet spikets for adding and removing buffer.

3. Polygraph/transducer-The piece of uterine tissue used for the assay is anchored at one end and connected to a Statham Strain Gauge Force Transducer at the other end which in turn is attached to a Grass Polygraph Model 79 for monitoring the contractions.

4. Assay Protocol (a) The tissue is equilibrated in the assay bath for one hour with washing with new buffer every 15 minutes. One gram of tension is kept on the tissue at all times.

(b) The tissue is stimulated initially with oxytocin at 10 nM to acclimate the tissue and with 4 mM potassium chloride (KCl) to determine the maximum contractile response.

(c) A cumulative dose response curve is then done with oxytocin and a concentration of oxytocin equivalent to approximately 80% of the maximum is used for estimating the $pA_2$ of the antagonist.

(d) The tissue is exposed to oxytocin (Calbiochemical, San Diego, Calif.) for one minute and washed out. There is a three minute interval before addition of the next dose of agonist or antagonist. When the antagonist is tested, it is given five minutes before the agonist. The agonist is given for one minute. All responses are integrated using a 7P10 Grass Integrator. A single concentration of oxytocin, equal to 80% of the maximum response, is used to test the antagonist. Three different concentrations of antagonists are used, two that will reduce the response to the agonist by less than 50% and one that will reduce the response greater than 50% (ideally this relation would be 25%, 50% and 75%). This is repeated three times for each dose of antagonist for a three point assay.

(e) Calculations for $pA_2$-The dose-response (DR) ratios are calculated for antagonist and a Schild's Plot is performed by plotting the Log (DR-1) vs. Log of antagonist concentration. The line plotted is calculated by least-squares regression analysis. The $pA_2$ is the concentration of antagonist at the point where the regression line crosses the 0 point of the Log (DR-1) ordinate. The $pA_2$ is the negative Log of the concentration of antagonist that will reduce the response to the agonist by one-half.

Oxytocin is well known for its hormonal role in parturition and lactation. Oxytocin agonists are useful clinically to induce lactation; induce or augment labor; control postpartum uterine atony and hemmorhage; cause uterine contraction after cesarean section or during other uterine surgery; and to induce therapeutic abortion. Oxytocin, acting as a neurotransmitter in the central nervous system, also plays an important role in the expression of central functions such as maternal behavior, sexual behavior (including penile erection, lordosis and copulatory behavior), yawning, tolerance and dependance mechanisms, feeding, grooming, cardiovascular regulation and thermoregulation (Argiolas and Gessa, *Neuroscience and Biobehavioral Reviews*, 15, 217–231 (1991)). Oxytocin antagonists find therapeutic utility as agents for the delay or prevention of premature labor; or to slow or arrest delivery for brief periods in order to undertake other therapeutic measures.

TACHYKININ ACTIVITY

Compounds of the present invention are believed to be tachykinin agents. Tachykinins are a family of peptides which share a common amidated carboxy terminal sequence. Substance P was the first peptide of this family to be isolated, although its purification and the determination of its primary sequence did not occur until the early 1970's. Between 1983 and 1984 several groups reported the isolation of two novel mammalian tachykinins, now termed neurokinin A (also known as substance K, neuromedin 1, and neurokinin α), and neurokinin B (also known as neuromedin K and neurokinin β). See, J. E. Maggio, *Peptides*, 6 (Supplement 3), 237–243 (1985) for a review of these discoveries.

Tachykinins are widely distributed in both the central and peripheral nervous systems. When released from nerves, they exert a variety of biological actions, which, in most cases, depend upon activation of specific receptors expressed on the membrane of target cells. Tachykinins are also produced by a number of non-neural tissues. The mammalian tachykinins substance P, neurokinin A, and neurokinin B act through three major receptor subtypes, denoted as NK-1, NK-2, and NK-3, respectively. These receptors are present in a variety of organs.

Substance P is believed inter alia to be involved in the neurotransmission of pain sensations, including the pain associated with migraine headaches and with arthritis. These peptides have also been implicated in gastrointestinal disorders and diseases of the gastrointestinal tract such as inflammatory bowel disease. Tachykinins have also been implicated as playing a role in numerous other maladies, as discussed infra.

In view of the wide number of clinical maladies associated with an excess of tachykinins, the development of tachykinin receptor antagonists will serve to control these clinical conditions. The earliest tachykinin receptor antagonists were peptide derivatives. These antagonists proved to be of limited pharmaceutical utility because of their metabolic instability. Recent publications have described novel classes of non-peptidyl tachykinin receptor antagonists which generally have greater oral bioavailability and metabolic stability than the earlier classes of tachykinin receptor antagonists. Examples of such newer non-peptidyl tachykinin receptor antagonists are found in European Patent Publication 591,040 A1, published Apr. 6, 1994; Patent Cooperation Treaty publication WO 94/01402, published Jan. 20, 1994; Patent Cooperation Treaty publication WO 94/04494, published Mar. 3, 1994; Patent Cooperation Treaty publication WO 93/011609, published Jan. 21, 1993, Patent Cooperation Treaty publication WO 94/26735, published Nov. 24, 1994. Assays useful for evaluating tachykinin receptor antagonists are well known in the art. See. e.g., J. Jukic, et al., *Life Sciences*, 49, 1463–1469 (1991); N. Kucharczyk, et al., *Journal of Medicinal Chemistry*, 36, 1654–1661 (1993); N. Rouissi, et al., *Biochemical and Biophysical Research Communications*, 176, 894–901 (1991).

NK-1 Receptor Binding Assay

Radioreceptor binding assays were performed using a derivative of a previously published protocol. D. G. Payan, et al., *Journal of Immunology*, 133,3260–3265 (1984). In this assay an aliquot of IM9 cells ($1 \times 10^6$ cells/tube in RPMI 1604 medium supplemented with 10% fetal calf serum) was incubated with 20 μM $^{125}$I-labeled substance P in the presence of increasing competitor concentrations for 45 minutes at 4° C.

The IM9 cell line is a well-characterized cell line which is readily available to the public. See, e.g., *Annals of the New York Academy of Science*, 190, 221–234 (1972); *Nature (London)*, 251, 443–444 (1974); *Proceedings of the National Academy of Sciences (USA)*, 71, 84–88 (1974). These cells were routinely cultured in RPMI 1640 supplemented with 50 μg/mL gentamicin sulfate and 10% fetal calf serum.

The reaction was terminated by filtration through a glass fiber filter harvesting system using filters previously soaked for 20 minutes in 0.1% polyethylenimine. Specific binding of labeled substance P was determined in the presence of 20 nM unlabeled ligand.

NK-2 Receptor Binding Assay

The CHO-hNK-2R cells, a CHO-derived cell line transformed with the human NK-2 receptor, expressing about 400,000 such receptors per cell, were grown in 75 cm² flasks or roller bottles in minimal essential medium (alpha modification) with 10% fetal bovine serum. The gene sequence of the human NK-2 receptor is given in N. P. Gerard, et al., *Journal of Biological Chemistry*, 265, 20455–20462 (1990).

For preparation of membranes, 30 confluent roller bottle cultures were dissociated by washing each roller bottle with 10 ml of Dulbecco's phosphate buffered saline (PBS) without calcium and magnesium, followed by addition of 10 ml of enzyme-free cell dissociation solution (PBS-based, from Specialty Media, Inc.). After an additional 15 minutes, the dissociated cells were pooled and centrifuged at 1,000 RPM for 10 minutes in a clinical centrifuge. Membranes were prepared by homogenization of the cell pellets in 300 mL 50 mM Tris buffer, pH 7.4 with a Tekmar® homogenizer for 10–15 seconds, followed by centrifugation at 12,000 RPM (20,000×g) for 30 minutes using a Beckman JA-14® rotor. The pellets were washed once using the above procedure and the final pellets were resuspended in 100–120 mL 50 mM Tris buffer, pH 7.4, and 4 ml aliquots stored frozen at −70° C. The protein concentration of this preparation was 2 mg/mL.

For the receptor binding assay, one 4-mL aliquot of the CHO-hNK-2R membrane preparation was suspended in 40 mL of assay buffer containing 50 mM Tris, pH 7.4, 3 mM manganese chloride, 0.02% bovine serum albumin (BSA) and 4 $\mu$g/mL chymostatin. A 200 $\mu$L volume of the homogenate (40 $\mu$g protein) was used per sample. The radioactive ligand was [$^{125}$I]iodohistidyl-neurokinin A (New England Nuclear, NEX-252), 2200 Ci/mMol. The ligand was prepared in assay buffer at 20 nCi per 100 $\mu$L; the final concentration in the assay was 20 pM. Non-specific binding was determined using 1 $\mu$M eledoisin. Ten concentrations of eledoisin from 0.1 to 1000 nM were used for a standard concentration-response curve.

All samples and standards were added to the incubation in 10 $\mu$L dimethylsulfoxide (DMSO) for screening (single dose) or in 5 $\mu$L DMSO for IC$_{50}$ determinations. The order of additions for incubation was 190 or 195 $\mu$L assay buffer, 200 $\mu$L homogenate, 10 or 5 $\mu$L sample in DMSO, 100 $\mu$L radioactive ligand. The samples were incubated 1 hr at room temperature and then filtered on a cell harvester through filters which had been presoaked for two hours in 50 mM Tris buffer, pH 7.7, containing 0.5% BSA. The filter was washed 3 times with approximately 3 mL of cold 50 mM Tris buffer, pH 7.7. The filter circles were then punched into 12×75 mm polystyrene tubes and counted in a gamma counter.

Tachykinin receptor antagonists are of value in the treatment of a wide variety of clinical conditions which are characterized by the presence of an excess of tachykinin. These clinical conditions may include disorders of the central nervous system such as anxiety, depression, psychosis, and schizophrenia; neurodegenerative disorders such as dementia, including senile dementia of the Alzheimer's type, Alzheimer's disease, AIDS-associated dementia, and Down's syndrome; demyelinating diseases such as multiple sclerosis and amyotrophic lateral sclerosis and other neuropathological disorders such as peripheral neuropathy, such as diabetic and chemotherapy-induced neuropathy, and post-herpetic and other neuralgias; acute and chronic obstructive airway diseases such as adult respiratory distress syndrome, bronchopneumonia, bronchospasm, chronic bronchitis, drivercough, and asthma; inflammatory diseases such as inflammatory bowel disease, psoriasis, fibrositis, osteoarthritis, and rheumatoid arthritis; disorders of the musculo-skeletal system, such as osteoporosis; allergies such as eczema and rhinitis; hypersensitivity disorders such as poison ivy; ophthalmic diseases such as conjunctivitis, vernal conjunctivitis, and the like; cutaneous diseases such as contact dermatitis, atopic dermatitis, urticaria, and other eczematoid dermatites; addiction disorders such as alcoholism; stress-related somatic disorders; reflex sympathetic dystrophy such as shoulder/hand syndrome; dysthymic disorders; adverse immunological reactions such as rejection of transplanted tissues and disorders related to immune enhancement or suppression such as systemic lupus erythematosis; gastrointestinal disorders or diseases associated with the neuronal control of viscera such as ulcerative colitis, Crohn's disease, emesis, and irritable bowel syndrome; disorders of bladder function such as bladder detrusor hyper-reflexia and incontinence; artherosclerosis; fibrosing and collagen diseases such as scleroderma and eosinophilic fascioliasis; irritative symptoms of benign prostatic hypertrophy; disorders of blood flow caused by vasodilation and vasospastic diseases such as angina, migraine, and Raynaud's disease; and pain or nociception, for example, that attributable to or associated with any of the foregoing conditions, especially the transmission of pain in migraine.

NK-1 antagonists are useful in the treatment of pain, especially chronic pain, such as neuropathic pain, post-operative pain, and migraines, pain associated with arthritis, cancer-associated pain, chronic lower back pain, cluster headaches, herpes neuralgia, phantom limb pain, central pain, dental pain, neuropathic pain, opioid-resistant pain, visceral pain, surgical pain, bone injury pain, pain during labor and delivery, pain resulting from burns, including sunburn, post partum pain, angina pain, and genitourinary tract-related pain including cystitis.

In addition to pain, NK-1 antagonists are especially useful in the treatment and prevention of urinary incontinence; irritative symptoms of benign prostatic hypertrophy; motility disorders of the gastrointestinal tract, such as irritable bowel syndrome; acute and chronic obstructive airway diseases, such as bronchospasm, bronchopneumonia, asthma, and adult respiratory distress syndrome; artherosclerosis; inflammatory conditions, such as inflammatory bowel disease, ulcerative colitis, Crohn's disease, rheumatoid arthritis, osteoarthritis, neurogenic inflammation, allergies, rhinitis, cough, dermatitis, urticaria, psoriasis, conjunctivitis, emesis, irritation-induced miosis; tissue transplant rejection; plasma extravasation resulting from cytokine chemotherapy and the like; spinal cord trauma; stroke; cerebral stroke (ischemia); Alzheimer's disease; Parkinson's disease; multiple sclerosis; amyotrophic lateral sclerosis; schizophrenia; anxiety; and depression.

NK-2 antagonists are useful in the treatment of urinary incontinence, bronchospasm, asthma, adult respiratory distress syndrome, motility disorders of the gastrointestinal tract, such as irritable bowel syndrome, and pain.

In addition to the above indications the compounds of the invention may be useful in the treatment of emesis, including acute, delayed, or anticipatory emesis, such as emesis induced by chemotherapy, radiation, toxins, pregnancy, vestibular disorders, motion, surgery, migraine, and variations in intercranial pressure. Most especially, the compounds of Formula I are of use in the treatment of emesis induced by antineoplastic (cytotoxic) agents including those routinely used in cancer chemotherapy.

Examples of such chemotherapeutic agents include alkylating agents, for example, nitrogen mustards, ethyleneimine compounds, alkyl sulfonates, and other compounds with an alkylating action, such as nitrosoureas, cisplatin, and dacarbazine; antimetabolites, for example, folic acid, purine, or pyrimidine antagonists; mitotic inhibitors, for example vinca alkaloids and derivatives of podophyllotoxin; and cytotoxic antibiotics.

Particular examples of chemotherapeutic agents are described, for instance, by D. J. Stewart in NAUSEA AND VOMITING: RECENT RESEARCH AND CLINICAL ADVANCES, (J. Kucharczyk, et al., eds., 1991), at pages 177–203. Commonly used chemotherapeutic agents include cisplatin, dacarbazine (DTIC), dactinomycin, mechlorethamine (nitrogen mustard), streptozocin, cyclophosphanide, carmustine (BCNU), lomustine (CCNU), doxorubicin, daunorubicin, procarbazine, mitomycin, cytarabine, etoposide, methotrexate, 5-fluorouracil, vinblastine, vincristine, bleomycin, and chlorambucil. R. J. Gralla, et al., *Cancer Treatment Reports*, 68, 163–172 (1984).

The compounds of Formula I may also be of use in the treatment of emesis induced by radiation, including radiation therapy such as in the treatment of cancer, or radiation sickness; and in the treatment of post-operative nausea and vomiting.

While it is possible to administer a compound employed in the methods of this invention directly without any formulation, the compounds are usually administered in the form of pharmaceutical compositions comprising a pharmaceutically acceptable excipient and at least one active ingredient. These compositions can be administered by a variety of routes including oral, rectal, transdermal, subcutaneous, intravenous, intramuscular, and intranasal. Many of the compounds employed in the methods of this invention are effective as both injectable and oral compositions. Such compositions are prepared in a manner well known in the pharmaceutical art and comprise at least one active compound. See, e.g., REMINGTON'S PHARMACEUTICAL SCIENCES, (16th ed. 1980).

In making the compositions employed in the present invention the active ingredient is usually mixed with an excipient, diluted by an excipient or enclosed within such a carrier which can be in the form of a capsule, sachet, paper or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing for example up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxybenzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 0.05 to about 100 mg, more usually about 1.0 to about 30 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical excipient.

The active compounds are generally effective over a wide dosage range. For examples, dosages per day normally fall within the range of about 0.01 to about 30 mg/kg of body weight. In the treatment of adult humans, the range of about 0.1 to about 15 mg/kg/day, in single or divided dose, is especially preferred. However, it will be understood that the amount of the compound actually administered will be determined by a physician, in the light of the relevant circumstances, including the condition to be treated, the chosen route of administration, the actual compound or compounds administered, the age, weight, and response of the individual patient, and the severity of the patient's symptoms, and therefore the above dosage ranges are not intended to limit the scope of the invention in any way. In some instances dosage levels below the lower limit of the aforesaid range may be more than adequate, while in other cases still larger doses may be employed without causing any harmful side effect, provided that such larger doses are first divided into several smaller doses for administration throughout the day.

Formulation Example 1

Hard gelatin capsules containing the following ingredients are prepared:

| Ingredient | Quantity (mg/capsule) |
| --- | --- |
| Compound of Example 42 | 30.0 |
| Starch | 305.0 |
| Magnesium stearate | 5.0 |

The above ingredients are mixed and filled into hard gelatin capsules in 340 mg quantities.

Formulation Example 2

A tablet formula is prepared using the ingredients below:

| Ingredient | Quantity (mg/tablet) |
| --- | --- |
| Compound of Example 54 | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

Formulation Example 3

A dry powder inhaler formulation is prepared containing the following components:

| Ingredient | Weight % |
| --- | --- |
| Compound of Example 67 | 5 |
| Lactose | 95 |

The active mixture is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
| --- | --- |
| Compound of Example 80 | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50–60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

Formulation Example 5

Capsules, each containing 40 mg of medicament are made as follows:

| Ingredient | Quantity (mg/capsule) |
| --- | --- |
| Compound of Example 27 | 40.0 mg |
| Starch | 109.0 mg |
| Magnesium stearate | 1.0 mg |
| Total | 150.0 mg |

The active ingredient, cellulose, starch, and magnesium stearate are blended, passed through a No. 20 mesh U.S. sieve, and filled into hard gelatin capsules in 150 mg quantities.

Formulation Example 6

Suppositories, each containing 25 mg of active ingredient are made as follows:

| Ingredient | Amount |
| --- | --- |
| Compound of Example 109 | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 7

Suspensions, each containing 50 mg of medicament per 5.0 ml dose are made as follows:

| Ingredient | Amount |
| --- | --- |
| Compound of Example 112 | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 ml |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation Example 8

Capsules, each containing 15 mg of medicament, are made as follows:

| Ingredient | Quantity (mg/capsule) |
| --- | --- |
| Compound of Example 31 | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

Formulation Example 9

An intravenous formulation may be prepared as follows:

| Ingredient | Quantity |
| --- | --- |
| Compound of Example 64 | 250.0 mg |
| Isotonic saline | 1000 ml |

Formulation Example 10

A topical formulation may be prepared as follows:

| Ingredient | Quantity |
| --- | --- |
| Compound of Example 46 | 1–10 g |
| Emulsifying Wax | 30 g |
| Liquid Paraffin | 20 g |
| White Soft Paraffin to | 100 g |

The white soft paraffin is heated until molten. The liquid paraffin and emulsifying wax are incorporated and stirred until dissolved. The active ingredient is added and stirring is continued until dispersed. The mixture is then cooled until solid.

Formulation Example 11

Sublingual or buccal tablets, each containing 10 mg of active ingredient, may be prepared as follows:

| Ingredient | Quantity Per Tablet |
| --- | --- |
| Compound of Example 64 | 10.0 mg |
| Glycerol | 210.5 mg |
| Water | 143.0 mg |
| Sodium Citrate | 4.5 mg |
| Polyvinyl Alcohol | 26.5 mg |
| Polyvinylpyrrolidone | 15.5 mg |
| Total | 410.0 mg |

The glycerol, water, sodium citrate, polyvinyl alcohol, and polyvinylpyrrolidone are admixed together by continuous stirring and maintaining the temperature at about 90° C. When the polymers have gone into solution, the solution is cooled to about 50–55° C. and the medicament is slowly admixed. The homogenous mixture is poured into forms made of an inert material to produce a drug-containing diffusion matrix having a thickness of about 2–4 mm. This diffusion matrix is then cut to form individual tablets having the appropriate size.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Frequently, it will be desirable or necessary to introduce the pharmaceutical composition to the brain, either directly or indirectly. Direct techniques usually involve placement of a drug delivery catheter into the host's ventricular system to bypass the blood-brain barrier. One such implantable delivery system, used for the transport of biological factors to specific anatomical regions of the body, is described in U.S. Pat. No. 5,011,472, issued Apr. 30, 1991, which is herein incorporated by reference.

Indirect techniques, which are generally preferred, usually involve formulating the compositions to provide for drug latentiation by the conversion of hydrophilic drugs into lipid-soluble drugs or prodrugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intra-arterial infusion of hypertonic solutions which can transiently open the blood-brain barrier.

The type of formulation employed for the administration of the compounds employed in the methods of the present invention may be dictated by the particular compounds employed, the type of pharmacokinetic profile desired from the route of administration and the compound(s), and the state of the patient.

We claim:

1. A method for the antagonism of the vasopressin $V_{1a}$ receptor comprising administering to a mammal in need of such antagonism a pharmaceutically effective amount of a 2-(azetidin-2-on-1-yl)acetic acid derivative of Formula I

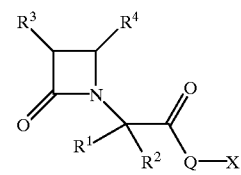

where $R^1$ is hydrogen, $C_1$–$C_5$ alkyl, —C(O)NR$^5$X', ($C_1$–$C_4$ alkylene)C(O)NR$^5$X', hydroxy substituted $C_1$–$C_5$ alkyl, $C_1$–$C_5$ acyl optionally substituted as the ethylene glycol ketal, $C_3$–$C_6$ cycloalkylcarbonyl, benzoyl, phenyl, phenyl($C^1$–$C^4$ alkylene), phenoxyacetyl, phenylacetyl where the phenyl is optionally substituted with halo, $C_1$–$C_4$ alkyl, $C_1$–$C_4$ alkoxy, or trifluoromethyl, or α-hydroxy-α-benzoylbenzyl;

$R^2$ is hydrogen, or hydroxy substituted $C_1$–$C_5$ alkyl;

$R^3$ is phthalimido, azido, phenoxyacetamido, 4,5-diphenyloxazol-2-on-3-yl, or a structure selected from the group consisting of (a)

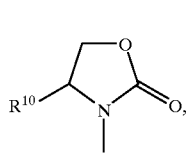

-continued

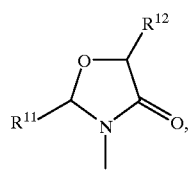
(b)

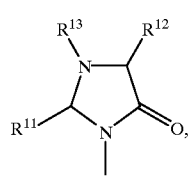
(c)

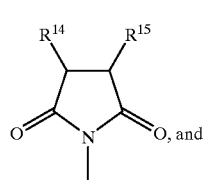
(d)

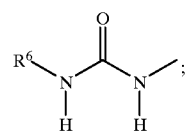
(e)

$R^4$ is:
  phenethyl, or 2-arylethen-1-yl where aryl is selected from the group consisting of furyl, pyrrolyl, pyridyl, thiazolyl, oxazolyl, isoxazolyl, imidazolyl, pyrazolyl, pyrimidinyl, thiadiazolyl, oxadiazolyl, quinolyl, isoquinolyl, naphthyl, and phenyl optionally substituted with 1 to 3 substituents selected from the group consisting of $C_1$–$C_6$ alkyl, $C_1$–$C_6$ alkoxy, $C_1$–$C_6$ alkylthio, nitro, halo, carboxy, and amido;

Q is —O—, —S—, or —NR$^5$—;

$R^5$ is hydrogen, hydroxy, $C_1$–$C_4$ alkoxycarbonyl, benzyl, or $C_1$–$C_4$ alkyl;

$R^6$ is $C_1$–$C_8$ alkyl, $C_3$–$C_8$ cycloalkyl, phenyl, or phenyl ($C_1$–$C_4$ alkylene) optionally substituted on the alkylene chain with $C_1$–$C_4$ alkoxycarbonyl;

X and X' are independently hydrogen, $C_1$–$C_6$ alkyl, 2-(trimethylsilyl)ethyl, $C_1$–$C_4$ alkyl ω-substituted with $C_1$–$C_4$ alkoxy, Y, (optionally substituted $C_1$–$C_4$ alkylene)-Y, or (optionally substituted $C_2$–$C_4$ alkylene)-NR$^7$R$^8$;

Y is phenyl, optionally substituted phenyl, diphenylmethyl, $C_3$–$C_6$ cycloalkyl, naphthyl, tetrahydronaphthyl, indanyl, fluorenyl, pyrrolyl, 1-($C_1$–$C_4$ alkyl)pyrrolyl, imidazolyl, pyrazolyl, pyridinyl, furyl, benzodioxanyl, tetrahydrofuryl, pyrrolidinyl, 1-($C_1$–$C_4$ alkyl)pyrrolidinyl, 1-benzylpyrrolidinyl, piperidinyl, 1-benzylpiperidin-4-yl, or quinuclidinyl;

$R^7$ is hydrogen, or $C_1$–$C_4$ alkyl;

$R^8$ is $C_1$–$C_4$ alkyl, phenyl, or pyridinyl optionally substituted with nitro;

$R^7$ and $R^8$ taken together with the nitrogen atom to which they are attached form morpholinyl, optionally substituted piperazinyl, or pyrrolidinyl;

$R^5$ and X' taken together with the nitrogen to which they are attached form:
  2-(pyrrolidin-1-ylmethyl)pyrrolidin-1-yl;
  piperidinyl optionally substituted at the 4-position with hydroxy, pyrrolidin-1-yl, piperidin-1-yl, benzyl, or piperidin-1-yl($C_1$–$C_4$ alkylene);
  piperidinyl mono- or disubstituted with methyl;
  piperazinyl optionally substituted at the 4-position with $C_1$–$C_4$ alkyl, $C_3$–$C_6$ cycloalkyl, phenyl, phenyl ($C_1$–$C_4$ alkylene), α-methylbenzyl, N-($C_1$–$C_4$ alkyl) acetamid-2-yl, or $C_1$–$C_4$ alkoxycarbonyl;
  1,2,3,4-tetrahydroisoquinolin-2-yl; or
  homopiperazinyl substituted in the 4-position with $C_1$–$C_4$ alkyl;

$R^2$, Q, and X taken together with the bridging carbon atoms to which they are attached form the lactone

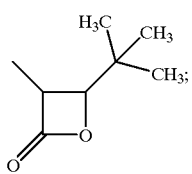

$R^{10}$ is $C_1$–$C_6$ alkyl, $C_3$–$C_6$ cycloalkyl, phenyl($C_1$–$C_4$ alkylene) where the phenyl is optionally substituted with $C_1$–$C_4$ alkyl, $C_1$–$C_4$ alkoxy or halo, naphthyl, thienyl, furyl, benzothienyl, benzofuryl, or phenyl optionally monosubstituted with $C_1$–$C_4$ alkyl, $C_1$–$C_4$ alkoxy or halo;

$R^{11}$ is $C_1$–$C_4$ alkyl, $C_3$–$C_7$ cycloalkyl, phenyl optionally substituted with one or two substituents independently selected from the group consisting of $C_1$–$C_4$ alkyl, $C_1$–$C_4$ alkoxy, halogen, hydroxy, cyano, carbamoyl, amino, mono($C_1$–$C_4$ alkyl)amino, di($C_1$–$C_4$ alkyl)amino, $C_1$–$C_4$ alkylsulfonylamino, and nitro, naphthyl optionally substituted with one or two substituents independently selected from the group consisting of $C_1$–$C_4$ alkyl, $C_1$–$C_4$ alkoxy, halogen, hydroxy, cyano, carbamoyl, amino, mono($C_1$–$C_4$ alkyl)amino, di($C_1$–$C_4$ alkyl)amino, and nitro, or $C_1$–$C_4$ alkoxycarbonyl;

$R^{12}$ is:
  $C_1$–$C_4$ alkyl optionally monosubstituted with a substituent selected from the group consisting of hydroxy, protected carboxy, carbamoyl, thiobenzyl and $C_1$–$C_4$ thioalkyl;
  phenyl optionally substituted with one or two substituents independently selected from the group consisting of $C_1$–$C_4$ alkyl, $C_1$–$C_4$ alkoxy, halogen, hydroxy, cyano, carbamoyl, amino, mono($C_1$–$C_4$ alkyl)amino, di($C_1$–$C_4$ alkyl)amino, $C_1$–$C_4$ alkylsulfonylamino, and nitro;
  naphthyl optionally substituted with one or two substituents independently selected from the group consisting of $C_1$–$C_4$ alkyl, $C_1$–$C_4$ alkoxy, halogen, hydroxy, cyano, carbamoyl, amino, mono($C_1$–$C_4$ alkyl)amino, di($C_1$–$C_4$ alkyl)amino, and nitro; or
  $C_1$–$C_4$ alkoxycarbonyl;

$R^{13}$ is:
  $C_1$–$C_4$ alkoxycarbonyl;
  benzyloxycarbonyl where the phenyl group is optionally substituted with one or two substituents independently selected from the group consisting of $C_1$–$C_4$ alkyl, $C_1$–$C_4$ alkoxy, halogen, cyano, nitro, amino, carbamoyl, hydroxy, mono($C_1$–$C_4$ alkyl) amino, and di($C_1$–$C_4$ alkyl)amino;

benzoyl where the phenyl group is optionally substituted with one or two substituents selected from the group consisting of $C_1$–$C_4$ alkyl, $C_1$–$C_4$ alkoxy, halogen, hydroxy, cyano, carbamoyl, amino, mono ($C_1$–$C_4$ alkyl)amino, di($C_1$–$C_4$ alkyl)amino, $C_1$–$C_4$ alkylsulfonylamino, and nitro; and $R^{14}$ and $R^{15}$ are:
  $C_1$–$C_5$ alkanoyloxy;
  benzoyloxy optionally substituted with one or two substituents independently selected from the group consisting of $C_1$–$C_4$ alkyl, $C_1$–$C_4$ alkoxy, halogen, cyano, nitro, amino and $C_1$–$C_4$ alkoxycarbonyl;
  benzyloxy;
  diphenylmethoxy; or
  triphenylmethoxy; or one of $R^{14}$ and $R^{15}$ is hydrogen and the other is:
  $C_1$–$C_5$ alkanoyloxy;
  benzoyloxy optionally substituted with one or two substituents independently selected from the group consisting of $C_1$–$C_4$ alkyl, $C_1$–$C_4$ alkoxy, halogen, cyano, nitro, amino and $C_1$–$C_4$ alkoxycarbonyl;
  benzyloxy;
  diphenylmethoxy; or
  triphenylmethoxy;

providing that $R^2$ may be other than hydrogen only when $R^1$ is hydroxy substituted $C_1$–$C_5$ alkyl; and hydrates, solvates and pharmaceutically acceptable acid addition salts thereof.

2. A method of claim 1 where the mammal is a human.

3. A method of claim 1 where $R^1$ is selected from the group consisting of $C_1$–$C_4$ alkyl, —C(O)$NR^5X'$, —($C_1$–$C_4$ alkylene) C(O)$NR^5X'$, hydroxy substituted $C_1$–$C_5$ alkyl, $C_1$–$C_5$ acyl optionally substituted as the ethylene glycol ketal, and α—hydroxy— α—benzoylbenzyl.

4. A method of claim 3 where X or X' is (optionally substituted $C_1$–$C_4$ alkylene)—Y; or (optionally substituted $C_2$–$C_4$ alkylene)—$NR^7R^8$.

5. A method of claim 4 where Y is optionally substituted phenyl.

6. A method of claim 5 where $R^2$ is hydrogen.

7. A method for the treatment of obsessive-compulsive disorder comprising administering to a mammal in need of such treatment a 2-(azetidin-2-on-1-yl)acetic acid derivative of Formula I

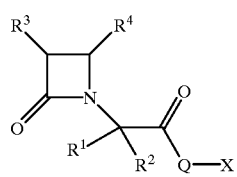

I where $r^1$ is hydrogen, $C_1$–$C_5$ alkyl, —C(O)$NR^5X'$, ($C_1$–$C_4$ alkylene)- C(O)$NR^5X'$, hydroxy substituted $C_1$–$C_5$ alkyl, $C_1$–$C_5$ acyl optionally substituted as the ethylene glycol ketal, $C_3$–$C_6$ cycloalkylcarbonyl, benzoyl, phenyl, phenyl($C_1$–$C_4$ alkylene), phenoxyacetyl, phenylacetyl where the phenyl is optionally substituted with halo, $C_1$–$C_4$ alkyl, $C_1$–$C_4$ alkoxy, or trifluoromethyl, or α-hydroxy-α-benzoylbenzyl;

$R^2$ is hydrogen, or hydroxy substituted $C_1$–$C_5$ alkyl;

$R^3$ is phthalimido, azido, phenoxyacetamido, 4,5-diphenyloxazol-2-on-3-yl, or a structure selected from the group consisting of

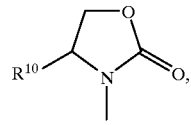

(a)

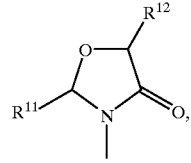

(b)

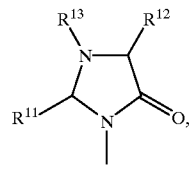

(c)

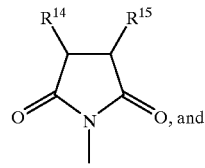

(d)

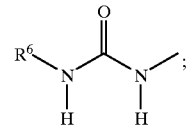

(e)

$R^4$ is:
  phenethyl, or 2-arylethen-1-yl where aryl is selected from the group consisting of furyl, pyrrolyl, pyridyl, thiazolyl, oxazolyl, isoxazolyl, imidazolyl, pyrazolyl, pyrimidinyl, thiadiazolyl, oxadiazolyl, quinolyl, isoquinolyl, naphthyl, and phenyl optionally substituted with 1 to 3 substituents selected from the group consisting of $C_1$–$C_6$ alkoxy, $C_1$–$C_6$ alkylthio, nitro, halo, carboxy, and amido;

Q is —O—, —S—, or —$NR^5$—;

$R^5$ is hydrogen, hydroxy, $C_1$–$C_4$ alkoxycarbonyl, benzyl, or $C_{1-C4}$ alkyl;

$R^6$ is $C_1$–$C_8$ alkyl, $C_3$–$C_8$ cycloalkyl, phenyl, or phenyl ($C_1$–$C_4$ alkylene) optionally substituted on the alkylene chain with $C_1$–$C_4$ alkoxycarbonyl;

X and X' are independently hydrogen, $C_1$–$C_6$ alkyl, 2-(trimethylsilyl)ethyl, $C_1$–$C_4$ alkyl ω-substituted with $C_1$–$C_4$ alkoxy, Y, (optionally substituted $C_1$–$C_4$ alkylene)-Y, or (optionally substituted $C_2$–$C_4$ alkylene)—$NR^7R^8$;

Y is phenyl, optionally substituted phenyl, diphenylmethyl, $C_3$–$C_6$ cycloalkyl, naphthyl, tetrahydronaphthyl, indanyl, fluorenyl, pyrrolyl, 1-($C_1$–$C_4$ alkyl)pyrrolyl, imidazolyl, pyrazolyl, pyridinyl, furyl, benzodioxanyl, tetrahydrofuryl, pyrrolidinyl, 1-($C_1$-$C_4$ alkyl)pyrrolidinyl, 1-benzylpyrrolidinyl, piperidinyl, 1-benzylpiperidin-4yl, or quinuclidinyl;

$R^7$ is hydrogen, or $C_1$-$C_4$ alkyl;

$R^8$ is $C_1$-$C_4$ alkyl, phenyl, or pyridinyl optionally substituted with nitro;

$R^7$ and $R^8$ taken together with the nitrogen atom to which they are attached form morpholinyl, optionally substituted piperazinyl, or pyrrolidinyl;

$R^5$ and X' taken together with the nitrogen to which they are attached form:
2-(pyrrolidin-1-ylmethyl)pyrrolidin-1-yl;
piperidinyl optionally substituted at the 4-position with hydroxy, pyrrolidin-1-yl, piperidin-1-yl, benzyl, or piperidin-1-yl($C_1$-$C_4$ alkylene);
piperidinyl mono- or disubstituted with methyl;
piperazinyl optionally substituted at the 4-position with $C_1$-$C_4$ alkyl, $C_3$-$C_6$ cycloalkyl, phenyl, phenyl ($C_1$-$C_4$ alkylene, α-methylbenzyl, N—($C_1$-$C_4$ alkyl)acetamid-2-yl, or $C_1$-$C_4$ alkoxycarbonyl;
1,2,3,4-tetrahydroisoquinolin-2yl; or homopiperazinyl substituted in the 4-position with $C_1$-$C_4$ alkyl;

$R^2$, Q, and X taken together with the bridging carbon atoms to which they are attached form the lactone

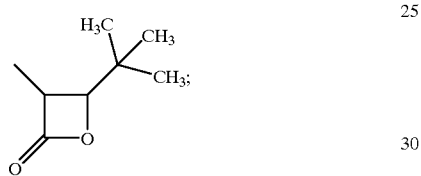

$R^{10}$ is $C_1$-$C_6$ alkyl, $C_3$-$C_6$ cycloalkyl, phenyl($C_1$-$C_4$ alkylene) where the phenyl is optionally substituted with $C_1$-$C_4$ alkyl, $C_1$-$C_4$ alkoxy or halo, naphthyl, thienyl, furyl, benzothienyl, benzofuryl, or phenyl optionally monosubstituted with $C_1$-$C_4$ alkyl, $C_1$-$C_4$ alkoxy or halo;

$R^{11}$ is $C_1$-$C_4$ alkyl, $C_3$-$C_7$ cycloalkyl, phenyl optionally susbstituted with one or two substituents independently selected from the group consisting of $C_1$-$C_4$ alkyl, $C_1$-$C_4$ alkoxy, halogen, hydroxy, cyano, carbamoyl, amino, mono($C_1$-$C_4$ alkyl)amino, $C_1$-$C_4$ alkylsulfonylamino, and nitro, naphthyl optionally substituted with one or two substituents independently selected from the group consisting of $C_1$-$C_4$ alkyl, $C_1$-$C_4$ alkoxy, halogen, hydroxy, cyano, carbamoyl, amino, mono($C_1$-$C_4$ alkyl)amino, di($C_1$-$C_4$ alkyl)amino, and nitro, or $C_1$-$C_4$ alkoxycarbonyl;

$R^{12}$ is:
$C_1$-$C_4$ alkyl optionally monosubstituted with a substituent selected from the group consisting of hydroxy, protected carboxy, carbamoyl, thiobenzyl and $C_1$-$C_4$ thioalkyl;
phenyl optionally substituted with one or two substituents independently selected from the group consisting of $C_1$-$C_4$ alkyl, $C_1$-$C_4$ alkoxy, halogen, hydroxy, cyano, carbamoyl, amino, mono($C_1$-$C_4$ alkyl)amino, di($C_1$-$C_4$ alkyl)amino, $C_1$-$C_4$ alkylsulfonyl-amino, and nitro;
naphthyl optionally substituted with one or two substituents independently seslected from the group consisting of $C_1$-$C_4$ alkyl, $C_1$14 $C_4$ alkoxy, halogen, hydroxy, cyano, carbamoyl, amino, mono($C_1$-$C_4$ alkyl)amino, di($C_1$-$C_4$ alkyl)amino, and nitro; or
$C_1$-$C_4$ alkoxycarbonyl;

$R^{13}$ is:
$C_1$-$C_4$ alkoxycarbonyl;
benzyloxycarbonyl where the phenyl group is optionally substituted with one or two substituents independently selected from the group consisting of $C_1$-$C_4$ alkyl, $C_1$-$C_4$ alkoxy, halogen, cyano, nitro, amino, carbamoyl, hydroxy, mono($C_1$-$C_4$ alkyl)amino, and di($C_1$-$C_4$ alkyl)amino;
benzoyl where the phenyl group is optionally substituted with one or two substituents selected from the group consisting of $C_1$-$C_4$ alkyl, $C_1$-$C_4$ alkoxy, halogen, hydroxy, cyano, carbamoyl, amino, mono ($C_1$-$C_4$ alkyl)amino, di($C_1$-$C_4$ alkyl)amino, $C_1$-$C_4$ alkylsulfonylamino, and nitro; and $R^{14}$ and $R^{15}$ are:
$C_1$-$C_5$ alkanoyloxy;
benzoyloxy optionally substituted with one or two substituents independently selected from the group consisting of $C_1$-$C_4$ alkyl, $C_1$–Alkoxy, halogen, cyano, nitro, amino and $C_1$-$C_4$ alkoxycarbonyl;
benzyloxy;
diphenylmethoxy; or
triphenylmethoxy; or one of $R^{14}$ and $R^{15}$ is hydrogen and the other is:
$C_1$-$C_5$ alkanoyloxy;
benzoyloxy optionally substituted with one or two substituents independently selected from the group consisting of $C_1$-$C_4$ alkyl, $C_1$-$C_4$ alkoxy, halogen, cyano, nitro, amino and $C_1$-$C_4$ alkoxycarbonyl;
benzyloxy;
diphenylmethoxy; or
triphenylmethoxy;

providing that $R^2$ may be other than hydrogen only when $R^1$ is hydroxy substituted $C_1$-$C_5$ alkyl; and hydrates, solvates and pharmaceutically acceptable acid addition salts thereof.

8. A method of claim 7 where $R^1$ is selected from the group consisiting of $C_1$-$C_4$ alkyl, —C(O)NR$^5$X', 13 ($C_1$-$C_4$ alkylene)C(O)NR$^5$X', hydroxy substituted $C_1$-$C_5$ alkyl, $C_1$-$C_5$ acyl optionally substituted as the ethylene glycol ketal, and α-hydroxy-α-benzoylbenzyl.

9. A method of claim 8 where X or X' is (optionally substituted $C_1$-$C_4$ alkylene)—Y; or (optionally substituted $C_2$-$C_4$ alkylene)—NR$^7$R$^8$.

10. A method of claim 9 where Y is optionally substituted phenyl.

11. A method of claim 10 where $R^2$ is hydrogen.

12. A method of claim 7 where the mammal is a human.

* * * * *